United States Patent [19]

Abood et al.

[11] Patent Number: 5,721,366

[45] Date of Patent: Feb. 24, 1998

[54] PLATELET AGGREGATION INHIBITORS

[75] Inventors: Norman Anthony Abood, Morton Grove; Daniel Lee Flynn, Mundelein; Robert Bruce Garland, Northbrook; Lori Ann Schretzman, Gurnee; Kenneth Williams, Harvey; Jeffery Alan Zablocki, Mt. Prospect; Susan Landis Hockerman, Chicago, all of Ill.

[73] Assignee: G. D. Searle & Co, Chicago, Ill.

[21] Appl. No.: 436,404

[22] PCT Filed: Mar. 30, 1994

[86] PCT No.: PCT/US94/03259

§ 371 Date: May 23, 1995

§ 102(e) Date: May 23, 1995

[87] PCT Pub. No.: WO94/22820

PCT Pub. Date: Oct. 13, 1994

[51] Int. Cl.⁶ .................... C07D 213/71; C07D 207/333
[52] U.S. Cl. ................................ 546/292; 548/550
[58] Field of Search .......................... 548/550; 246/292

[56] References Cited

U.S. PATENT DOCUMENTS 3,474,093  10/1969  McCauly ........................ 260/247.1

Primary Examiner—Johann Richter
Assistant Examiner—Dominic Keating
Attorney, Agent, or Firm—Cynthia S. Kovacevic; Roger A. Williams

[57] ABSTRACT

This invention relates to compounds having the following formula

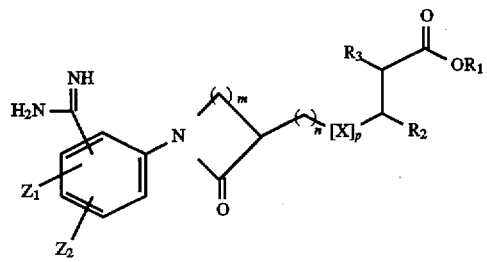

or a pharmaceutically acceptable salt thereof which are useful in the inhibition of platelet aggregation, to pharmaceutical compositions of such phenylamidines derivatives, and to a method of inhibiting platelet aggregation in mammals by administering such compounds and compositions.

18 Claims, No Drawings ns
PLATELET AGGREGATION INHIBITORS

This application is a 371 of PCT/US94/03259 filed on Mar. 30, 1994, published as WO94/22820 Oct. 13, 1994.

FIELD OF THE INVENTION

The present invention relates to pharmaceutical agents (compounds) which inhibit platelet aggregation in mammals.

BACKGROUND OF THE INVENTION

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as GP IIb/IIIa; this is an important feature of the platelet function. Inhibitors of this interaction are useful in modulating platelet thrombus formation.

It is also known that another large glycoprotein named fibronectin, which is a major extracellular matrix protein, interacts with platelets. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., Biochem. 23, 1767–1774 (1984); Plow et al., Proc. Natl. Acad. Sci. 82, 8057–8061 (1985); Ruggeri et al., Ibid. 83, 5708–5712 (1986); Ginsberg et al., J. Biol. Chem. 260 (7), 3931–3936 (1985); Haverstick et al., Blood 66 (4), 946–952 (1985); and Ruoslahti and Pierschbacher, Science 238, 491–497 (1987). Still other such inhibitory peptides are disclosed in European Patent Applications 275,748 and 298,820.

European Patent Application 512,831 discloses piperidinylalkylazacycloalkanones which inhibit the binding of fibrinogen to blood platelets and therefore are useful for inhibiting the aggregation of blood platelets.

European Patent Application 503,548 discloses cyclic urea derivatives (imidazolones and triazolones) useful in inhibiting cellular interactions thereby useful for treating or preventing, thrombosis, embolisms and metastases.

European Patent Application 496,378 discloses amidinobiphenyl compounds which inhibit cell-cell and cell-matrix interaction and are thus useful for treating thrombosis, cerebrovascular diseases, pulmonary embolisms, myocardial infarction, arteriosclerosis, osteoporosis and tumour metastases.

European Patent Application 445,796 discloses acetic acid derivatives which have inhibitory action on the bonding of adhesive proteins to blood platelets as well as on blood-platelet aggregation and cell-cell adhesion.

European Patent Application 372,486 discloses N-acyl beta amino acid derivatives and their salts. Said compounds are useful for inhibiting platelet aggregation in the treatment of thrombosis, stroke, myocardial infarction, inflammation and arteriosclerosis, and for inhibiting metastasis.

European Patent Application 381,033 discloses amidino or guanidincaryl substituted alkanoic acid derivatives useful for the treatment of thrombosis, apoplexy, cardiac infarction, inflammation, arteriosclerosis and tumors.

U.S. Ser. Nos. 07/847,260; 07/777,811; and 07/777,875 disclose amidinobenzenaminosuccinyl acid derivatives useful as platelet aggregation inhibitors.

U.S. Ser. No. 07/904,257 discloses phenylamidine alkanoic acids and lactones useful as platelet aggregation inhibitors.

The EP-A 0 567 968 and EP-A 0 567 966 claiming a priority earlier than the present one, but having been published thereafter disclose cyclic imino derivatives which are useful as platelet aggregation inhibiting agent.

EP-A 0 539 343 claiming an earlier priority than the present one but published thereafter describes aliphatic amino derivatives exhibiting a terminal phenyl-amidino group, but no lactam ring. These compounds are useful to modulate and/or inhibit platelet aggregation.

EP-A 0 483 667 discloses among many others amidinophenyl pyrrolidinones which also are useful as platelet aggregation inhibitors.

SUMMARY OF THE INVENTION

The present invention relates to a class of compounds represented by the formula:

or a pharmaceutically acceptable salt thereof, wherein $Z_1$ and $Z_2$ are independently selected from the group consisting of hydrogen, alkyl of 1 to 6 carbon atoms, hydroxy, halo and alkoxy of 1 to 6 carbon atoms;

$R_1$ is selected from the group consisting of hydrogen, lower alkyl of 1 to 6 carbon atoms, lower alkenyl of 2 to 6 carbon atoms, lower alkynyl of 2 to 6 carbon atoms, alkyloxycarbonyloxyalkyl, alicyclic. hydrocarbon radicals and aromatic hydrocarbon radicals optionally substituted by hydroxy, lower alkoxy of 1 to 6 carbon atoms, lower alkyl of 1 to 6 carbon atoms, halo, nitro, amino, acyloxy, phenyl or naphthyl;

$R_2$ is selected from the group consisting of hydrogen, lower alkyl of 1 to 6 carbon atoms, lower alkenyl of 2 to 6 carbon atoms, lower alkynyl of 2 to 6 carbon atoms, cycloalkyl, aryl, monocyclic, bicyclic, or tricyclic heterocyclic radicals in which are present 1 to 3 heteroatoms independently selected from oxygen, nitrogen, or sulfur, wherein said groups are optionally substituted by one or more radicals selected from the group consisting of hydroxy, lower alkoxy of 1 to 6 carbon atoms, lower alkyl of 1 to 6 carbon atoms, halo, nitro, cyano, azido, ureido, ureylene, carboxyl, carbonyl derivatives, trifluoromethyl, acyloxy, alkylthio, arylthio, alkylsulfinyl, arylsulfinyl, alkylsulfonyl, arylsulfonyl, amino, alkylamino, trialkylsilyl, aminosulfonyl, dialkylamino, alkanoylamino, aroylamino, phenyl and naphthyl;

$R_3$ is selected from the group consisting of hydrogen, alkyl of 1 to 6 carbon atoms, alkoxy of 1 to 6 carbon atoms, fluoro, amino, monoalkylamino, dialkylamino, acylamino, alkylsulfonylamino, arenesulfonylamino, hydroxyl, alkoxycarbonyl and alkoxycarbonylalkyl;

X is selected from the group consisting of

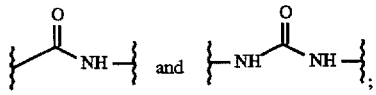

m is an integer from 1 to 4;

n is an integer from 0 to 4; and p is 0 or 1 wherein n and p are not both 0.

It is another object of the invention to provide pharmaceutical compositions comprising compounds of the formula I. Such compounds and compositions have usefulness as modulators and/or inhibitors of platelet aggregation. The invention also relates to a method of therapeutically inhibiting or modulating platelet aggregation in a mammal in need of such treatment.

DETAILED DESCRIPTION OF THE INVENTION

The present invention relates to a class of compounds represented by the formula I, described above.

A preferred embodiment of the present invention is a compound of the formula I or a pharmaceutically acceptable salt thereof, wherein $R_1$ is selected from the group consisting of hydrogen or lower alkyl of 1 to 6 carbon atoms;

$R_2$ is selected from the group consisting of hydrogen, lower alkyl of 1 to 6 carbon atoms, lower alkenyl of 2 to 6 carbon atoms, lower alkynyl of 2 to 6 carbon atoms and phenyl all optionally substituted by phenyl or trialkylsilyl;

$Z_1$ and $Z_2$ are hydrogen;

n is an integer 0 or 1; and m is an integer 2 or 3.

Embodiments exemplifying the invention are the following compounds:

ethyl 3S-[[[1-[4-(aminoiminomethyl)phenyl]-2-oxo-3-pyrrolidinyl]acetyl]amino]-4-pentenoate;

3S-[[[1-[4-(aminoiminomethyl)phenyl]-2-oxo-3-pyrrolidinyl]acetyl]amino]-4-pentenoic acid, monohydrochloride;

ethyl 3S-[[[1-[4-(aminoiminomethyl)phenyl]-2-oxo-3-pyrrolidinyl]acetyl]amino]-4-pentenoate, enantiomerically enriched isomer A;

3S-[[[1-[4-(aminoiminomethyl)phenyl]-2-oxo-3-pyrrolidinyl]acetyl]amino]-4-pentenoic acid, monohydrochloride enantiomerically enriched isomer A;

ethyl 3S-[[[1-[4-(aminoiminomethyl)phenyl]-2-oxo-3-pyrrolidinyl]acetyl]amino]-4-pentenoate, enantiomerically enriched isomer B;

3S-[[[1-[4-(aminoiminomethyl)phenyl]-2-oxo-3-pyrrolidinyl]acetyl]amino]-4-pentenoic acid, enantiomerically enriched isomer B;

ethyl 3-[[[1-[4-(aminoiminomethyl)phenyl]-2-oxo-3-pyrrolidinyl]acetyl]amino]propionate;

3-[[[1-[4-(aminoiminomethyl)phenyl]-2-oxo-3-pyrrolidinyl]acetyl]amino]propionic acid;

ethyl 3-[[[1-[4-(aminoiminomethyl)phenyl]-2-oxo-3-pyrrolidinyl]acetyl]amino]butanoate;

3-[[[1-[4-(aminoiminomethyl)phenyl]-2-oxo-3-pyrrolidinyl]acetyl]amino]butanoic acid;

ethyl 3-[[[1-[4-(aminoiminomethyl)phenyl]-2-oxo-3-pyrrolidinyl]acetyl]amino]-3-phenylpropionate;

3-[[[1-[4-(aminoiminomethyl)phenyl]-2-oxo-3-pyrrolidinyl]acetyl]amino]-3-phenylpropionic acid;

ethyl 3(S)-[[[1-[4-(aminoiminomethyl)phenyl]-2-oxo-3-pyrrolidinyl]acetyl]amino]-4-pentynoate;

3(S)-[[[1-[4-(aminoiminomethyl)phenyl]-2-oxo-3-pyrrolidinyl]acetyl]amino]-4-pentynoic acid;

3-[[[1-[4-(aminoiminomethyl)phenyl]-2-oxo-3-pyrrolidinyl]acetyl]amino]-N-[(phenylmethoxy)carbonyl]-L-alanine, ethyl ester;

3-[[[1-[4-(aminoiminomethyl)phenyl]-2-oxo-3-pyrrolidinyl]acetyl]amino]-N-[(phenylmethoxy)carbonyl]-L-alanine;

ethyl 3(S)-[[[[1-[4-(aminoiminomethyl)phenyl]-2-oxo-3-pyrrolidinyl]amino]carbonyl]amino]-4-pentenoate;

(S)-[[[1-[4-(aminoiminomethyl)phenyl]-2-oxo-3-pyrrolidinyl]amino]carbonyl]amino]-4-pentenoic acid;

1-[4-(aminoiminomethyl)phenyl]-βS-methyl-2-oxo-3-pyrrolidinehexanoic acid, monohydrochloride;

ethyl 1-[4-(aminoiminomethyl)phenyl]-βS-methyl-2-oxo-3-pyrrolidinehexanoate, trifluoroacetate;

ethyl 3-[[[1-[4-(aminoiminomethyl)phenyl]-2-oxo-3-piperidinyl]acetyl]amino]-5-(trimethylsilyl)-4-pentynoate;

3-[[[1-[4-(aminoiminomethyl)phenyl]-2-oxo-3-piperidinyl]acetyl]amino]-5-(trimethylsilyl)-4-pentynoic acid;

ethyl 3-[[[1-[4-(aminoiminomethyl)phenyl]-2-oxo-3-piperidinyl]acetyl]amino]-4-pentynoate;

3-[[[1-[4-(aminoiminomethyl)phenyl]-2-oxo-3-piperidinyl]acetyl]amino]-4-pentynoic acid;

ethyl 3-[[[1-[4-(aminoiminomethyl)phenyl]-2-oxo-3-piperidinyl]acetyl]amino]-6,6-dimethyl-4-heptynoate;

3-[[[1-[4-(aminoiminomethyl)phenyl]-2-oxo-3-piperidinyl]acetyl]amino]-6,6-dimethyl-4-heptynoic acid;

ethyl 3-[[[1-[4-(aminoiminomethyl)phenyl]-2-oxo-3-piperidinyl]acetyl]amino]-5-phenyl-4-pentynoate;

3-[[[1-[4-(aminoiminomethyl)phenyl]-2-oxo-3-piperidinyl]acetyl]amino]-5-phenyl-4-pentynoic acid;

ethyl 3-[[[1-[4-(aminoiminomethyl)phenyl]-2-oxo-3-piperidinyl]acetyl]amino]-butanoate;

3-[[[1-[4-(aminoiminomethyl)phenyl]-2-oxo-3-piperidinyl]acetyl]amino]butanoic acid;

ethyl 3-[[[1-[4-(aminoiminomethyl)phenyl]-2-oxo-3-piperidinyl]acetyl]amino]-3-phenylpropanoate;

3-[[[1-[4-(aminoiminomethyl)phenyl]-2-oxo-3-piperidinyl]acetyl]amino]-3-phenylpropanoic acid;

ethyl 3(S)-[[[1-[4-(aminoiminomethyl)phenyl]-2-oxo-3-piperidinyl]acetyl]amino]-4-pentenoate;

3(S)-[[[1-[4-(aminoiminomethyl)phenyl]-2-oxo-3-piperidinyl]acetyl]amino]-4-pentenoic acid;

ethyl 3-[[[1-[4-(aminoiminomethyl)phenyl]-2-oxo-3-pyrrolidinyl]acetyl]amino]propanoate, trifluoroacetate, enantiomerically enriched isomer B;

3-[[[1-[4-(aminoiminomethyl)phenyl]-2-oxo-3-pyrrolidinyl]acetyl]amino]propanoic acid, trifluoroacetate, enantiomerically enriched isomer B;

ethyl 3-[[[[1-[4-(aminoiminomethyl)phenyl]-2-oxo-3-pyrrolidinyl]amino]carbonyl]amino]propanoate, trifluoroacetate;

3-[[[[1-[4-(aminoiminomethyl)phenyl]-2-oxo-3-pyrrolidinyl]amino]carbonyl]amino]propanoic acid, trifluoroacetate;

ethyl 3-[[[1-[4-(aminoiminomethyl)phenyl]-2-oxo-3-piperidinyl]acetyl]amino]propanoate;

3-[[[1-[4-(aminoiminomethyl)phenyl]-2-oxo-3-piperidinyl] acetyl]amino]propanoic acid;

3-[[[1-[4-(aminoiminomethyl)phenyl]-2-oxo-3-piperidinyl] acetyl]amino]-3-(3-thienyl)propanoic acid;

ethyl 3(S)-[[[1-[4-(aminoiminomethyl)phenyl]-2-oxo-3-piperidinyl]acetyl]amino]-3-(3-furanyl) propanoate;

3(S)-[[[1-[4-aminoiminomethyl)phenyl]-2-oxo-3-piperidinyl]acetyl]amino]-3-(3-furanyl)propanoic acid;

ethyl 3-[[[1-[4-(aminoiminomethyl)phenyl]-2-oxo-3-piperidinyl]acetyl]amino]-3-(2-furanyl)propanoate;

3-[[[1-[4-(aminoiminomethyl)phenyl]2-oxo-3-piperidinyl] acetyl]amino]-3-(2-furanyl)propanoic acid;

ethyl 3-[[[1-[4-(aminoiminomethyl)phenyl]-2-oxo-3-piperidinyl]acetyl]amino]-3-(4-methoxyphenyl) propanoate;

3-[[[1-[4-(aminoiminomethyl)phenyl]-2-oxo-3-piperidinyl] acetyl]amino]-3-(4-methoxyphenyl)propanoic acid;

3(S)-[[[1-[4-(aminoiminomethyl)phenyl]-2-oxo-3-piperidinyl]acetyl]amino]-4-pentenoic;

ethyl 3(S)-[[[-[4-(aminoiminomethyl)phenyl]-2-oxo-3-piperidinyl]acetyl]amino]-4-pentenoate, enantiomerically enriched, isomer B;

3(S)-[[[1-[4-(aminoiminomethyl)phenyl]-2-oxo-3-piperidinyl]acetyl]amino]4-pentenoic enantiomerically enriched, isomer B;

ethyl 3(S)-[[[1-[4-(aminoiminomethyl)phenyl]-2-oxo-3-piperidinyl]acetyl]amino]-4-pentynoate, enantiomerically enriched, isomer B;

3(S)-[[[1-[4-(aminoiminomethyl)phenyl]-2-oxo-3-piperidinyl]acetyl]amino-4-pentynoic acid, enantiomerically enriched, isomer B;

ethyl 3(S)-[[[1-[4-(aminoiminomethyl)phenyl]-2-oxo-3-piperidinyl]acetyl]amino]butyrate;

3S-[[[1-[4-(aminoiminomethyl)phenyl]-2-oxo-3-piperidinyl]acetyl]amino]butyric acid;

ethyl 3S-[[[1-4-(aminoiminomethyl)phenyl]-2-oxo-3-piperidinyl]acetyl]amino]-3-phenylpropionate;

3S-[[[1-[4-(aminoiminomethyl)phenyl]-2-oxo-3-piperidinyl]acetyl]amino]-3-phenylpropionic acid;

ethyl 3-[[[1-[4-(aminoiminomethyl)phenyl]-2-oxo-3-pyrrolidinyl]amino]carbonyl]amino]propionate trifluoroacetate. Enantiomerically Enriched Isomer A;

3-[[[[1-[4-(aminoiminomethyl)phenyl]-2-oxo-3-pyrrolidinyl]amino]carbonyl]amino]propanoic acid trifluoroacetate. Enantiomerically Enriched Isomer A;

ethyl 3-[[[[1-[4(aminoiminomethyl)phenyl]-2-oxo-3-pyrrolidinyl]amino]carbonyl]amino]propionate trifluoroacetate. Enantiomerically Enriched Isomer B;

3-[[[[1-[4-(aminoiminomethyl)phenyl]-2-oxo-3-pyrrolidinyl]amino]carbonyl]amino]propanoic acid trifluoroacetate. Enantiomerically Enriched Isomer B;

ethyl 3(R)-[[[[1-[4-(aminoiminomethyl)phenyl]-2-oxo-3-pyrrolidinyl]amino]carbonyl]amino]butanoate trifluoroacetate. Enantiomerically Enriched Isomer B;

3(R)-[[[[1-[4-(aminoiminomethyl)phenyl]-2-oxo-3-pyrrolidinyl]amino]carbonyl]amino]butanoic acid trifluoroacetate. Enantiomerically Enriched Isomer B;

ethyl 3(S)-[[[[1-[4-(aminoiminomethyl)phenyl]-2-oxo-3-pyrrolidinyl]amino]carbonyl]amino]benzenepropanoate trifluoroacetate. Enantiomerically Enriched Isomer B;

3[S)-[[[[1-[4-(aminoiminomethyl)phenyl]-2-oxo-3-pyrrolidinyl]amino]carbonyl]amino]benzenepropanoic acid trifluoroacetate. Enantiomerically Enriched Isomer B;

ethyl 3-[[[[1-[4-(aminoiminomethyl)phenyl]-2-oxo-3-pyrrolidinyl]amino]carbonyl]amino]-2(S)-[[(phenylmethoxy)carbonyl]amino]propanoate trifluoroacetate. Enantiomerically Enriched Isomer B; and 3-[[[[1-[4-(aminoiminomethyl)phenyl]-2-oxo-3-pyrrolidinyl]amino]carbonyl]amino]-2(S)-[[(phenylmethoxy)carbonyl]amino]propanoic acid trifluoroacetate. Enantiomerically Enriched Isomer B.

As used herein, the term "alkyl" refers to a straight chain or branched chain hydrocarbon radical having from 1 to 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein, the term "alkoxy" includes straight or branched chain oxy containing radicals of the formula —$OR_4$ wherein $R_4$ is an alkyl moiety as defined above. Examples of such groups are methoxy, ethoxy, n-propoxy, n-butoxy, isobutoxy, t-butoxy, sec-butoxy, isopropoxy and the like.

As used herein the terms "halo" or "halogen" refer to a chloro (Cl), fluoro (F), bromo (Br) or iodo (I) radical.

As used herein the term "alkenyl" refers to unsaturated acyclic hydrocarbon radicals containing at least one double bond and 2 to 6 carbon atoms which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the term "alkynyl" refers to acyclic hydrocarbon radicals containing one or more triple bonds and 2 to 6 carbon atoms. Examples of such groups are ethynyl, propynyl, butynyl, pentynyl, hexynyl and the like.

As used herein the term "alkoxycarbonyl" having 1 to 6 carbon atoms refers to the radical

wherein the R represents alkyl having 1 to 6 carbon atoms. Illustrative of such groups are methoxycarbonyl, ethoxycarbonyl, propanoxycarbonyl, pentanoxycarbonyl and the like.

The term "cycloalkyl" as used herein means a saturated cyclic carbon radical containing 3 to 6 carbon atoms. Examples of suitable cycloalkyl radicals include cyclopropyl, cyclopropenyl, cyclobutyl, cyclopentyl, cyclohexyl, 2-cyclohexen-1-yl, and the like.

The term "amino", as used herein, denotes a radical of the formula —$NH_2$. The terms "monoalkylamino" or "alkylamino" as used herein are represented by the radical —$NHR_4$ wherein $R_4$ is an alkyl group as previously described. The term "dialkylamino" as used herein is represented by the radical —$NR_4R_5$ wherein $R_4$ and $R_5$ are the same or different alkyl groups, as defined above.

The term "trialkylsilyl" embraces a radical attached to the nucleus of Formula I through a silicon atom and which silicon atom is substituted by three terminal alkyl groups which are the same or different, as defined above.

The term "alkylthio" embraces radicals containing a linear or branched alkyl group, of one to about six carbon atoms attached to a divalent sulfur atom, which radical is attached to the nucleus of formula I through the sulfur moiety.

The terms "sulfinyl" and "sulfonyl", whether used alone or linked to other terms such as "alkyl", denote —SO— and —$SO_2$—, respectively.

The terms "aryl" and "arene", as used herein denote carbocyclic aromatic ring systems composed of one or more aromatic rings. Preferred aryl groups are those consisting of one, two or three benzene rings. The term "aryl" embraces aromatic radicals such as phenyl, naphthyl and biphenyl. The term "arylthio" as used herein denotes an aryl group attached to a divalent sulfur atom which is attached to the nucleus of formula I through the sulfur atom, exemplified by phenylthio.

As used herein, the term "cyano" is represented by a radical of the formula —CN.

The terms "hydroxy" and "hydroxyl" as used herein are synonomous and are represented by a radical of the formula —OH.

The term "nitro" as used herein is represented by a radical of the formula —NO$_2$.

The term "acyloxy" as used herein is represented by a radical of the formula

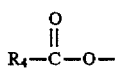

wherein R$_4$ is alkyl as defined above.

The term "alkyloxycarbonyloxyalkyl" as used herein denotes a radical of the formula

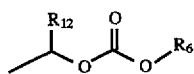

wherein R$_{12}$ is H or alkyl as defined above and R$_6$ is alkyl or cycloalkyl as defined above.

The term "acylamino" as used herein is represented by a radical of the formula

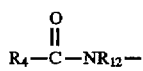

wherein R$_{12}$ is H or alkyl as defined above and R$_4$ is alkyl or alkoxy optionally substituted by aryl as defined above.

The terms "alkylsulfonoylamino" and "arenesulfonylamino" are denoted radicals of the formula R$_7$—SO$_2$—NR$_{12}$— wherein R$_7$ is an alkyl or arene radical as defined above and R$_{12}$ is H or alkyl as defined above.

The term "alkoxycarbonyloxy" as used herein denotes a radical of the formula R$_4$O—C(O)O— wherein R$_4$ is an alkyl radical as defined above.

As used herein the term "heterocyclyl" embraces monocyclic, fused bicyclic and fused tricyclic ring radicals containing from 1 to 3 heteroatoms selected from the group consisting of oxygen, nitrogen and sulfur.

The terms "carboxy" or "carboxyl" denote radicals of the formula —COOH.

As used herein the term "carbonyl derivative" is represented by a radical of the formula

wherein the carbonyl is attached to the nucleus of formula I and R$_8$ represents a radical selected from the group H, alkyl, aryl, cycloalkyl, amino, monoalkylamino, and dialkylamino as defined above.

The term "azido" as used herein is represented by the radical —N$_3$.

The term "ureido" as used herein is a urea derived radical denoted by an (aminocarbonyl)amino radical of the formula

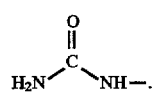

The term "ureylene" as used herein is also a urea derived radical and is represented by the formula

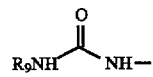

wherein R$_9$ is alkyl, cycloalkyl or aryl.

As used herein "trifluoromethyl" is represented by a radical of the formula —CF$_3$.

The term "alkylsulfinyl" and "arylsulfinyl" are represented by a radical of the formula R$_{13}$—SO—, wherein R$_{13}$ is an alkyl or aryl radical as defined above. The terms "arylsulfonyl", "alkylsulfonyl" and "aminosulfonyl" as used herein are denoted by a radical of formula R$_{10}$—SO$_2$— wherein R$_{10}$ is amino, alkyl or aryl as defined above.

As used herein, the term "alkanoylamino" refers to a radical of the formula

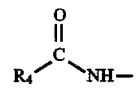

wherein R$_4$ is an alkyl radical as defined above.

The term "aroylamino" is denoted by a radical of the formula

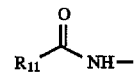

wherein R$_{11}$ is an aryl radical as defined above.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The compounds as shown in Formula I can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of the pharmacologically acceptable salts may be prepared by conventional means. (See Berge et al., *J Pharm. Sci.*, 66(1), 1–19 (1977) for additional examples of pharmaceutically acceptable salts.)

This invention also relates to a method of inhibiting platelet aggregation and more specifically, a method of treatment involving the administration of compounds of Formula I together with pharmaceutically acceptable carriers to achieve such inhibition.

For the inhibition of platelet aggregation, compounds of the present invention may be administered orally, parenterally, or by inhalation spray, rectally, or topically in dosage unit formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus the dosage regimen may vary widely. Dosage levels of the order from about 0.01 mg to about 50 mg per kilogram of body weight per day are useful in the treatment of the above-indicated conditions.

For oral administration, the pharmaceutical composition may be in the form of, for example, a tablet, capsule, suspension or liquid. The pharmaceutical composition is preferably made in the form of a dosage unit containing a particular amount of the active ingredient. These may contain, for example, an amount of active ingredient from about 1 to 500 mg, preferably from about 25 to 350 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 10 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The platelet aggregation inhibitors of the present invention can be prepared by methods analogous to solution phase peptide synthesis [see: The Peptides: Analysis, Synthesis, Biology (E. Gross and J. Meienhofer, eds.), Vol. 1–5, Academic Press, New York] combined with standard synthetic methods. Schemes A–H which follow are illustrative of methods for preparing the compounds of the present invention.

The general synthetic sequence is outlined in Scheme A. The cyano group is converted to the amidine via the thioimidate in nearly quantitative yield. The thioimidate is formed by first treating the cyano compound with hydrogen sulfide ($H_2S$) followed by alkylation with methyl iodide. Next, treatment of the thioimidate with ammonium acetate affords the amidine as the salt (HI). The final compounds for biological testing were obtained by purification by reverse phase high pressure liquid chromatography [High Performance Liquid Chromatography Protein and Peptide Chemistry (F. Lottspeich, A. Henscher, K. P. Hupe, eds.) Walter DeGruyter, New York, 1981].

When X=amide or urea, the corresponding benzonitriles of Scheme A can be prepared as illustrated in Scheme B. Briefly, acylation of the appropriately substituted benzonitrile by reaction with an omega bromoalkanoyl chloride in the presence of base is followed by lactam formation by treatment with sodium hydride. The lactam is then alkylated by deprotonation with lithium bistrimethylsilylamide (LiHMDS) followed by alkylation with a tert-butyl omega bromoalkanoate. The resultant alkyl ester is cleaved to the alkyl acid by treatment with trifluoroacetic acid (TFA) [The Peptides: Analysis, Synthesis, Biology (E. Gross and J. Meienhofer, eds.), Vol. 1–5, Academic Press, New York]. The benzonitrile derivatives of Scheme A where X=amide can be prepared by activation of the acid for peptide coupling (e.g. N,N'-disuccinimidyl carbonate [DSC]) followed by reaction with the appropriately substituted β-amino ester or acid. The benzonitrile derivatives of Scheme A where X=urea can be prepared by reacting the alkylacid with diphenylphosphoryl azide [(PhO)$_2$PON$_3$] [S. Yamada, K. Ninomiya and T. Shioiri *Tetrahedron Lett.* 2343 (1973); P. A. S. Smith *Org. React.* Vol. 3, 337 (1946); J. H. Saunders, R. J. Slocombe *Chem. Rev.*, V. 43, 203 (1948)] followed by trapping of the intermediate isocyanate with the appropriately substituted free β-aminoester. The benzonitrile derivatives of Scheme A where p=0 can be prepared as illustrated in Scheme C wherein the lactam of Scheme B is alkylated by deprotonation with lithium bistrimethylsilylamide followed by reaction with the appropriately substituted omega haloalkanoate.

The beta amino acids can be either purchased or prepared from commercially available starting materials using known methods as illustrated in Scheme D. The racemic beta aryl beta amino acids can be prepared from the appropriate aryl aldehyde, malonic acid, and ammonium acetate as shown in Scheme D—method 1 (Johnson and Livak *J. Am. Chem. Soc.* 299 (1936)]. The racemic beta alkyl beta amino acids can be prepared from the corresponding alkene and chlorosulfonyl isocyanate (CSI) which goes through the beta lactam intermediate as shown in Scheme D—method 2 [W. A. Szabo *Aldrichimica Acta* 23 (1977); R. Graf *Angew. Chem. Internat. Edit.* 172 (1968)]. The beta lactam can be opened to the ethyl ester by treatment with anhydrous hydrochloric acid in ethanol as shown Scheme D. For example, 1,3-butadiene was reacted with CSI to form the corresponding vinyl beta lactam and following subsequent opening with anhydrous HCl in ethanol was used in example 1. An alternative method to form racemic beta amino esters is shown in Scheme D method 3. Nucleophiles can be added to 4-benzoyloxy-2-azetidinone to afford a variety of 3-substituted beta amino esters after treatment with anhydrous HCl in ethanol. For example, 4-benzoyloxy-2-azetidinone can be reacted with allyltrimethylsilane under Lewis acid catalysis [titanium tetrachloride—K., Prasad et al. Vol. 19 Heterocycles 2099 (1982)]. The racemic beta amino acids can be resolved using classical methods described in the literature [E. Fischer, H. Scheibler, R. Groh Ber. 2020 (1910); E. Fischer, H. Scheibler Annalen 337 (1911)].

Chiral beta amino acids can be prepared using many different approaches including the following methods: homologation of the alpha amino acids using an Arndt-Eistert reaction as shown in Scheme D method 4 [Meier and Zeller Angew. Chem. Int. Ed. Eng. 32–43 (1975)] [M. Rodriguez et al. Tetrahedron Lett. 5153 (1990); W. J. Greenlee J. Med. Chem. 434 (1985) and references therein]; through the addition of amines to alpha,beta unsaturated esters bearing a chiral auxilliary as shown in Scheme D, Method 5 [J. d'Angelo and J. Maddaluno J. Am. Chem. Soc. 8112–14 (1986)]; through an enantioselective hydrogenation of a dehydroamino acid as shown in Scheme D, method 6 [see: Asymmetric Synthesis, Vol. 5, (J. D. Morrison, ed.) Academic Press, New York, 1985]; through the addition of enantiomerically pure amines to alpha,beta unsaturated esters as shown in Scheme D, method 7 [see: S. G. Davies and O. Ichihara Tetrahedron:Asymmetry 183–186 (1991)]. A variety of 2-substituted beta amino esters can be prepared by treating the carbobenzyloxy protected β-amino ester with 2.2 equivalents of lithium diisopropylamide (LDA) followed by quenching with an electrophile (alkyl halide, aldehyde, azocompound, or α,β-unsaturated nitro) in the manner of Seebach and coworkers [V. H. Estermann and D. Seebach, Helvetica Chimica Acta, V. 71, 1824, (1988)]as illustrated in Scheme D, method 8. Alternatively, quenching of the enolate with 2-sulfonyloxaziridine affords α-hydroxyesters (Davis, et al., JOC, (1984) 49, 3243–3244). Synthesis of a representative pyrrolidinone containing compound is outlined in Scheme E. The commercially available aminobenzonitrile (Aldrich) was acylated with 4-bromobutyryl chloride to give the amide 1. Treatment of this product with sodium hydride afforded the lactam 2. Alkylation of the lactam (LiHMDS, t-butyl bromoacetate) and hydrolysis of the t-butyl ester gave the pyrrolidinoneacetic acid derivative 4. The acid was converted to the active ester with N,N'-disuccinimidyl carbonate (DSC) and was then coupled with a variety of β-amino acids. In this example, (3S)-ethyl 3-amino-4 pentenoate was used to give the coupled product 5. Transformation of the benzonitrile to the benzamidine 6 was accomplished using a three step sequence (H₂S then MeI then NH₄OAc). Enzymatic hydrolysis of the ethyl ester with porcine liver esterase gave the desired target 7.

The resolution of the pyrrolidinoneacetic acid 4 is illustrated in Scheme F and was accomplished by crystallization of the α-methyl-benzylamine salts from acetonitrile. Twelve recrystallizations were required to enrich the diastereomeric pairs to a 91:9 ratio. The (+) acid and the (−) acid of 4 were each coupled to (3S)-ethyl 3-amine-4-pentenoate and carried through to the final products (e.g. 7a using (+)-4) as previously described in Scheme E.

Synthesis of the pyrrolidone urea series is described in Scheme G. Commercially available α-amino-γ-butyrolactone hydrobromide (Aldrich) was converted to the Boc protected lactone 9 (Boc20, N-methylmorpholine). Treatment of this material and 4-aminobenzonitrile with 2 equivalents of LiHMDS afforded the hydroxyamide 10. Cyclization of 10 to the lactam 11 (Ph₃P, Diethylazodicarboxylate (DEAD)) and treatment of the crude product with dry HCl/EtOAc gave the α-aminolactam hydrochloride 12 in good overall yield. A one pot synthesis of the urea 13 from 12 using sequentially, triphosgene [H. Eckert and B. Forsten, Angew. Chem. Int. Ed. Engl. 894–895 (1987)]and EtN(i-Pr)₂ then (3S)-ethyl 3-amino-4-pentenoate/EtN(i-Pr)₂, was taken on to the final product 15 according to the procedure described in Scheme E.

Scheme H illustrates the method used to synthesize a pyrrolidinone-hexanoic acid derivative. Commercially available (S)-(−)-β-citronellol 16 (Aldrich) was converted to the alcohol 17 by protection of the alcohol (tert-butyldimethylsilylchloride (TBDMSCl), imidazole) followed by ozonolysis with a borohydride workup. Iodide 18 (I₂, imidazole, Ph₃P) was used to alkylate the lithium enolate of 2 (LiHMDS). Cleavage of the silyl ether afforded the alcohol 19 as a mixture of chiral diastereomers. Jones oxidation gave the acid 20 which was converted to the final product 21 according to the procedure described in Scheme E.

The following examples are provided to illustrate the present invention and are not intended to limit the scope thereof. Those skilled in the art will readily understand that known variations of the conditions and processes of the following preparative procedures can be used to prepare the compounds of the present invention.

Scheme A

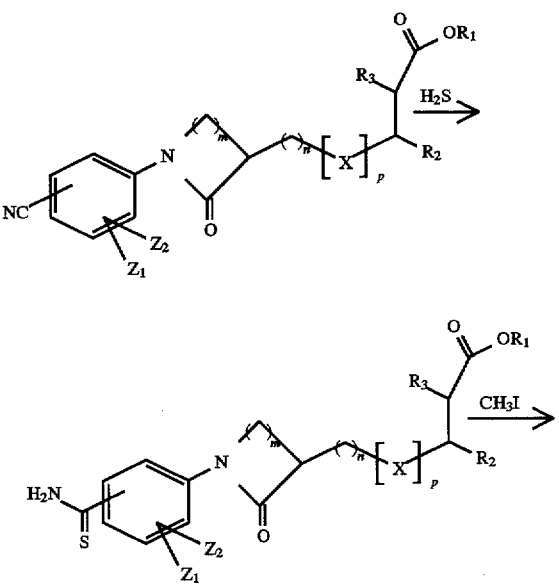

Scheme A
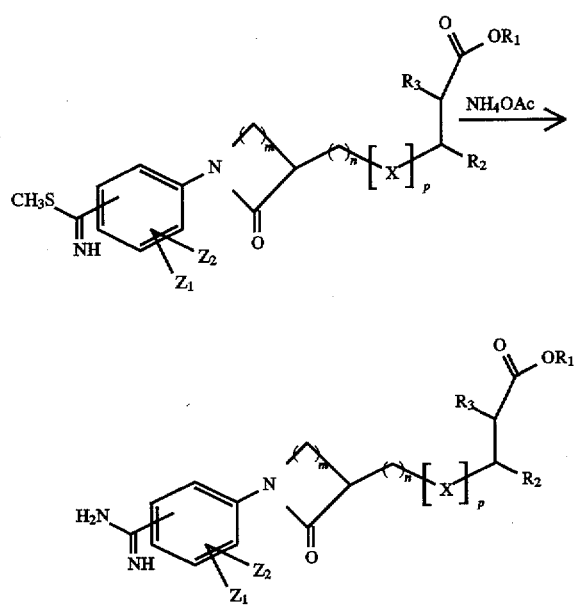
Scheme B
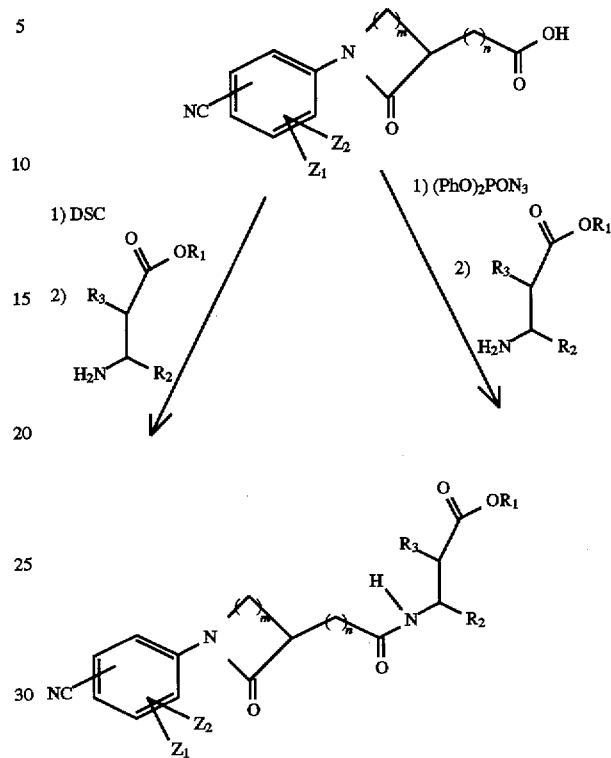
Scheme B
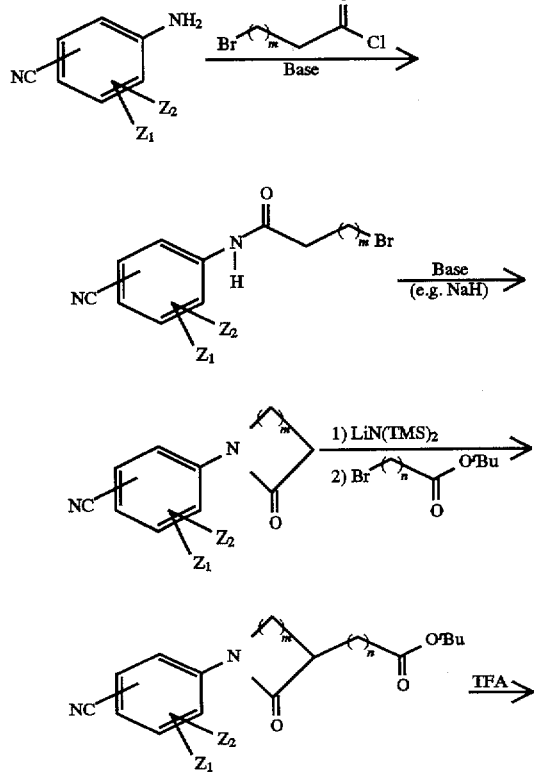
Scheme C
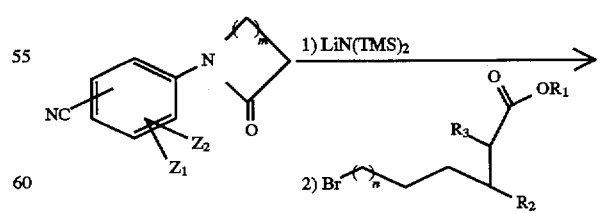

15
-continued
Scheme C
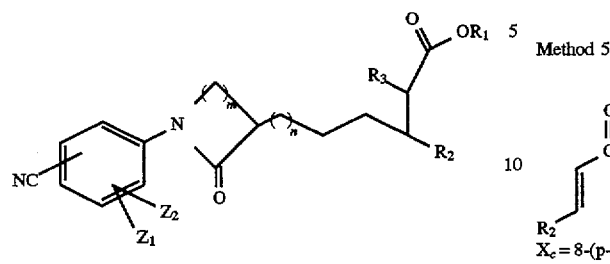
(Compounds of the Formula I wherein p = 0)
Scheme D
Method 1
Method 2
Method 3
Method 4
*Indicates Chiral Center
Retention of Stereochemistry
16
-continued
Scheme D
Method 5
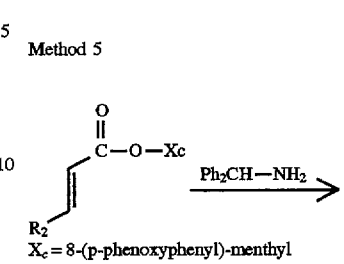
$X_c$ = 8-(p-phenoxyphenyl)-menthyl
Method 6
Method 7
*Indicates Chiral Center

Scheme D
Method 8
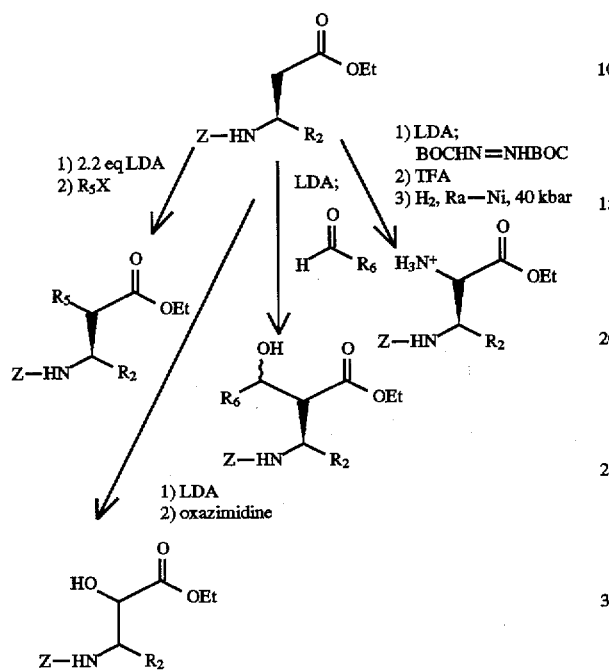
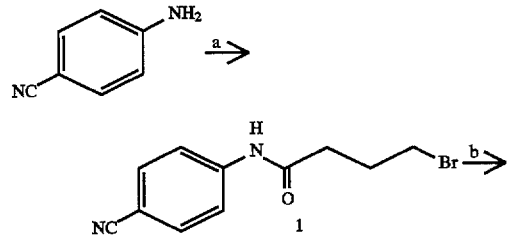
Scheme E
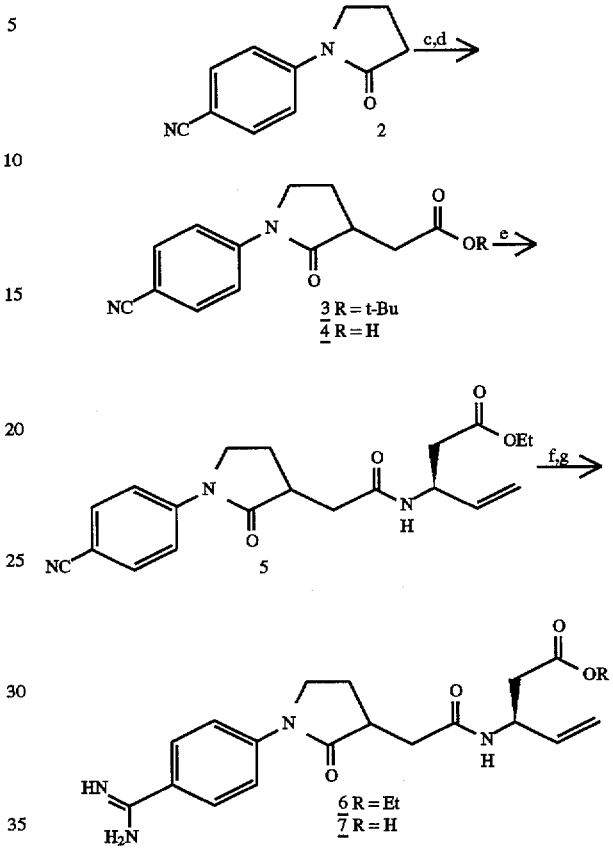
a 4-bromobutyryl chloride, Et₃N;
b NaH;
c LiHMDS, t-butyl bromoacetate;
d TFA;
e DSC, then 3(S)-vinyl-β-alanine HCl, Et₃N;
f 1) H₂S, Et₃N; 2) MeI; 3) NH₄OAc;
g porcine liver esterase.
Scheme F
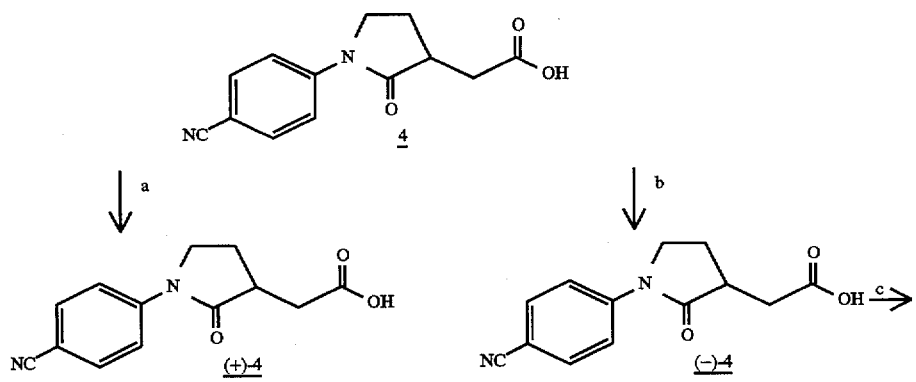

-continued
Scheme F

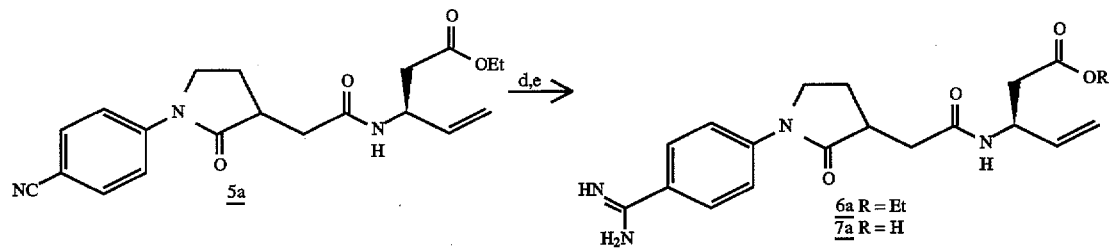

<sup>a</sup>(R)-(+)-α-methylbenzylamine, then HCl;
<sup>b</sup>(S)-(−)-α-methylbenzylamine, then HCl;
<sup>c</sup>DSC, then 3(S)-vinyl-β-alanine HCl, Et₃N;
<sup>d</sup>1) H₂S, Et₃N; 2) MeI; 3) NH₄OAc;
<sup>e</sup>porcine liver esterase.

Scheme G

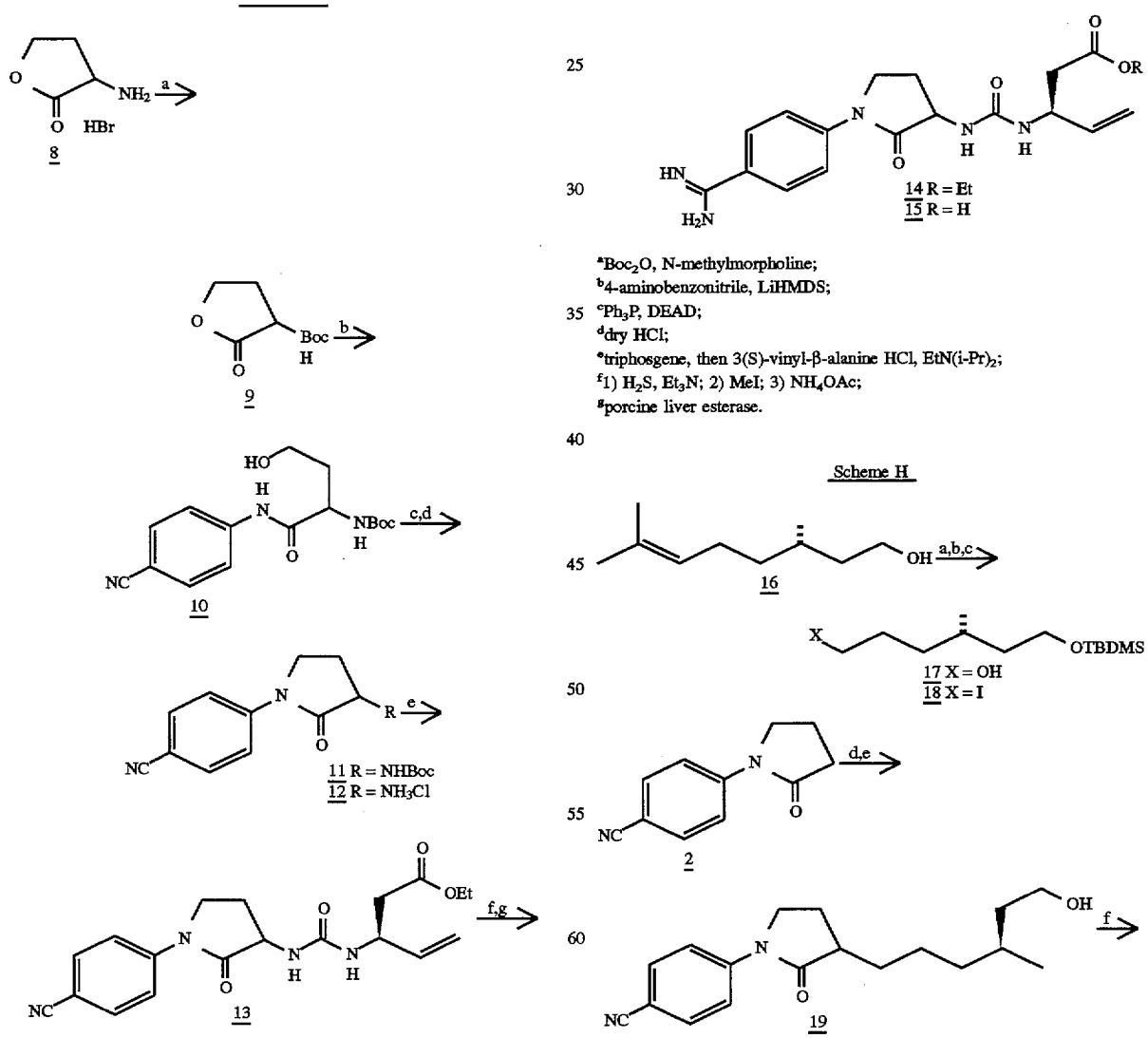

<sup>a</sup>Boc₂O, N-methylmorpholine;
<sup>b</sup>4-aminobenzonitrile, LiHMDS;
<sup>c</sup>Ph₃P, DEAD;
<sup>d</sup>dry HCl;
<sup>e</sup>triphosgene, then 3(S)-vinyl-β-alanine HCl, EtN(i-Pr)₂;
<sup>f</sup>1) H₂S, Et₃N; 2) MeI; 3) NH₄OAc;
<sup>g</sup>porcine liver esterase.

Scheme H

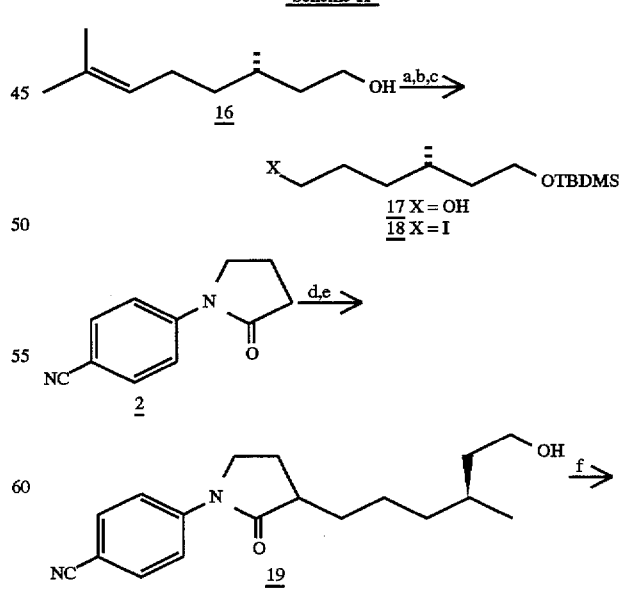

-continued
Scheme H

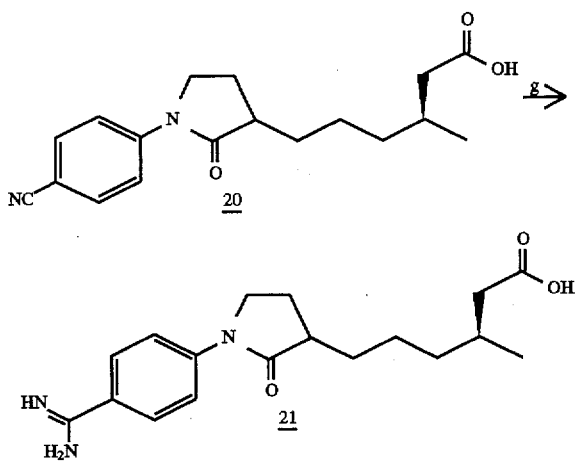

*TBDMSCl, Imidazole;
bO3, then NaBH4;
cPh3P, I2, Imidazole;
dLiHMDS, then 18;
eTBAF;
fJones reagent;
g1) H2S, Et3N; 2) MeI; 3) NH4OAc.

EXAMPLE 1

Ethyl 3S-[[[1-[4-(aminoiminomethyl)phenyl]-2-oxo-3-pyrrolidinyl]acetyl]amino]-4-pentenoate

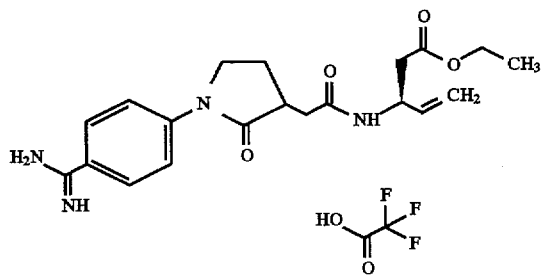

A. Preparation of N-(4-cyanophenyl)-4-bromobutanamide

To a stirred solution of 4-aminobenzonitrile (12.7 g, 108 mmol) and triethylamine (13.1 g, 129 mmol) in 100 mL of $CH_2Cl_2$, cooled in an ice bath under nitrogen, was added neat, via syringe 4-bromobutyryl chloride (24 g, 129 mmol). The reaction mixture was allowed to warm to room temperature. After 2 hours, the mixture was diluted with $CH_2Cl_2$ and washed with 1N $NaHSO_4$, saturated NaCl, dried ($MgSO_4$) and concentrated. Trituration with hexane afforded 27.7 g (96%) of product as a pale yellow solid used directly in the next reaction:H NMR ($d_6$-DMSO) δ2.14 (m, 2H), 2.56 (t, J=7 Hz, 2H), 3.61 (t, J=7 Hz, 2H), 7.75 (d, J=8 Hz, 2H), 7.81 (d, J=8 Hz, 2H).

Anal. calc'd. for $C_{11}H_{11}N_2OBr$: C, 49.46; H, 4.15; N, 10.49 Found: C, 49.73; H, 4.25; N, 10.54

B. Preparation of 1-(4-cyanophenyl)-2-pyrrolidinone

To a stirred solution of the product of step A (27.7 g, 104 mmol) in 150 mL of THF was added NaH (4.77 g, 119 mmol)(60% w/w dispersion on mineral oil). The reaction was stirred at ambient temperature for 3.5 hours, then diluted with EtOAc and washed with dilute HCl. The organic phase was further washed with saturated NaCl, dried ($MgSO_4$) and concentrated. The solid residue was recrystallized from EtOAc/$Et_2O$ affording 12.2 g (63%) of product:H NMR ($CDCl_3$) δ2.22 (m, 2H), 2.66 (m, 2H), 3.88 (m, 2H), 7.65 (d, J=8 Hz, 2H), 7.80 (d, J=8 Hz, 2H).

Anal. Calc'd. for $C_{11}H_{10}N_2O$: C, 70.95; H, 5.41: N, 15.04 Found: C, 70.72; H, 5.67; N, 15.04.

C. Preparation of t-butyl 1-(4-cyanophenyl)-2-oxo-3-pyrrolidinyl-3-acetate.

To a stirred solution of the product of step B (1.86 g, 10 mmol) in 50 mL dry THF at -75° C. under nitrogen was added LiPIMDS (1M in THF 10 mL) dropwise via syringe. After 15 minutes, 4 mL of dry HMPA was added followed by the rapid addition of t-butyl bromoacetate (1.95 g, 10 mmol) via syringe. After an additional 15 minutes at -75° C., the reaction mixture was poured into dilute HCl and extracted (2×) with EtOAc. The organic fractions were combined, washed with water, saturated NaCl, dried ($MgSO_4$) and concentrated. The solid residue was triturated with hot $Et_2O$ then precipitated with diisopropyl ether affording 2.1 g (70%) of product: H NMR ($CDCl_3$) δ1.45 (s, 3H), 1.95 (m, 1H), 2.50 (m, 2H), 2.85 (m, 2H), 3.03 (m, 1H), 3.83 (m, 2H), 7.64 (d, J=8 Hz, 2H), 7.81 (d, J=8 Hz, 2H).

D. Preparation of 1-4-cyanophenyl)-2-oxo-3-pyrrolidinyl-3-acetic acid

The product of step C (1.8 g, 6 mmol) was dissolved in 20 mL of TFA/$H_2O$ (9:1) and stirred at room temperature for 2 hours. The reaction was poured onto crushed ice. The precipitate was filtered, washed with water and dried affording 1.42 g (97%) of product used directly in the next reaction:H NMR ($CDCl_3$) δ1.96 (m, 1H), 2.48–2.63 (m, 2H), 2.95 (m, 1H), 3.07 (m, 1H), 3.85 (m, 2H), 7.66 (d, J=8 Hz, 2H), 7.80 (d, J=8 Hz, 2H).

E. Preparation of [1-(4-cyanophenyl)-2-oxo-3-pyrrolidinyl] acetyl-(3S)-vinyl-β-alanine ethyl ester.

To a stirred solution of the product of step D (500 mg, 2.05 mmol) and DMAP (50 mg) in 4 mL of DMF/pyridine (1:1) was added N,N'-disuccinimidyl carbonate (DSC) (525 mg, 2.05 mmol). After stirring at room temperature for 15 minutes, ethyl (3S)-vinyl-β-alanine hydrochloride (368 mg, 2.05 mmol) was added, followed by triethylamine (207 mg, 2.05 mmol). After an additional 30 minutes of stirring at room temperature, the reaction was poured into saturated $NaHCO_3$ and extracted with EtOAc. The organic layer was washed with dilute HCl, dried ($MgSO_4$) and concentrated affording 760 mg (100%) of product which formed a waxy solid on standing: H NMR ($CDCl_3$) δ1.25 (m, 3H), 1.98 (m, 1H), 2.93–2.57 (m, 2H), 2.63 (m, 2H), 2.81 (m, 1H), 3.10 (m, 1H), 3.83 (m, 2H), 4.14 (q, J=7 Hz, 2H), 4.86 (m, 1H), 5.10–5.27 (m, 2H), 5.84 (m, 1H), 7.65 (d, J=8 Hz, 2H), 7.80 (d, J=8 Hz, 2H).

F. Preparation of Ethyl 3S-[[[1-[4-(aminoiminomethyl) phenyl]-2-oxo-3-pyrrolidinyl]acetyl]amino]-4-pentenoate Hydrogen sulfide was bubbled through a solution of the product of step E (756 mg, 2.05 mmol) and triethylamine (1.24 g, 12.3 mmol) in 10 mL of pyridine at room temperature for 5 minutes. The reaction was stoppered and stirred at room temperature overnight. The reaction was poured into dilute HCl and the yellow precipitate was filtered, washed with water and dried. To the resulting thioamide in acetone (15 mL) was added iodomethane (4.36 g, 31 mmol) and the reaction was stirred at 65° C. under nitrogen for 35 minutes. Removal of the solvent under reduced pressure afforded the crude thioimidate hydroiodide. To this yellow residue was added anhydrous ammonium acetate (315 mg, 4.1 mmol) and MeOH (15 mL). The mixture was stirred at 65° C. under nitrogen for 3.5 hours then concentrated. The residue was purified by reverse phase chromatography on a Water® C-18 Delta Pak column using a 0.05% TFA/water:acetonitrile gradient (95% of 0.05% TFA/water:acetonitrile to 60% of 0.05% TFA/water:acetonitrile over 30 min) affording 280 mg (27%) of the title compound as the TFA salt:

Anal. calc'd. for $C_{22}H_{27}N_4O_6F_3 \cdot 0.33\ H_2O$: C, 52.17; H, 5.51; N, 11.06. Found: C, 52.16; H, 5.36; N, 11.06.

EXAMPLE 2

3(S)-[[[1-[4-(aminoiminomethyl)phenyl]-2-oxo-3-pyrrolidinyl]acetyl]amino]-4-pentenoic acid, monohydrochloride

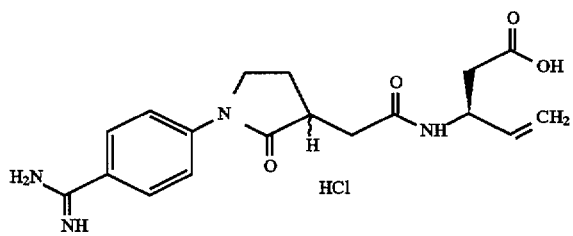

To a suspension of the product of step F Example 1 (503 mg, 1.0 mmol) in 15 mL of 0.1M pH 7.4 phosphate buffer and 0.2 mL of acetonitrile was added a suspension of porcine liver esterase (0.9 mL). The reaction was stirred at room temperature for 2 days. The zwitterion product was filtered, washed with water and dried. The white solid was suspended in MeOH and 2N HCl (0.55 mL) was added. The resulting solution was evaporated to dryness and the residue was triturated with acetonitrile affording 275 mg (70%) of product as the hydrochloride salt: (m.p. 153°–156° C.).

Anal. calc'd. for $C_{18}H_{23}N_4O_4Cl \cdot 1/2H_2O$: C, 53.53; H, 5.99; N, 13.87; Cl, 8.78. Found: C, 53.49; H, 6.05; N, 13.71; Cl, 8.63.

EXAMPLE 3

Ethyl 3S-[[[1-[4-(aminoiminomethyl)phenyl]-2-oxo-3-pyrrolidinyl]acetyl]amino]-4-pentenoate, enantiomerically enriched isomer A

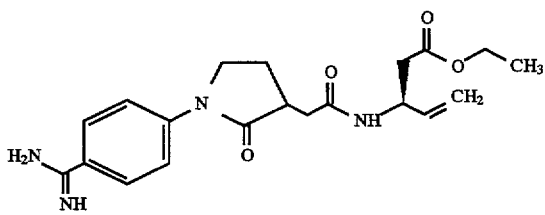

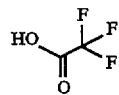

A. Preparation of (−)-1-(4-cyanophenyl)-2-pyrrolidinone-3-acetic acid.

To a solution of the product of example 1, step D (970 mg, 3.97 mmol) in hot acetonitrile (100 mL) was added (S)-(−)-α-methyl-benzylamine (481 mg, 3.97 mmol). After 12 recrystallizations from acetonitrile 320 mg of chiral salt was obtained ($[\alpha]_D^{25}=-40.4°$ MeOH) (m.p. 171°–174° C.). The free acid was liberated upon partitioning between EtOAc and dilute HCl ($[\alpha]_D^{25}=-34.4°$, MeOH) (m.p. 193°–194° C.). The enantiomeric excess (82% e.e.) was determined by chiral HPLC analysis on a chiralpak-OD-R column using 30/70 acetonitrile/0.05M Na perchlorate, 2.5 pH (flow rate=0.5 mL/min).

B. Preparation of [1-(4-cyanophenyl)-2-oxo-3-pyrrolidinyl] acetyl-(3S)-vinyl-β-alanine ethyl ester, enantiomerically enriched isomer A.

The title compound was prepared from the product of step A (240 mg, 0.98 mmol) in a manner similar to example 1, step E affording 360 mg (99%) of product.

Anal. calc'd. for $C_{20}N_3O_4$: C, 65.02; H, 6.28; N, 11.38. Found: C, 64.89; H, 6.29; N, 11.36.

C. Preparation of Ethyl 3S-[[[1-[4-(aminoiminomethyl) phenyl]-2-oxo-3-pyrrolidinyl]acetyl]amino]-4-pentenoate, enantiomerically enriched isomer A The title compound was prepared from the product of step B (350 mg, 0.95 mmol) in a manner similar to example 1, step F affording 260 mg (58%) of product as the TFA salt following reverse phase chromatography [m.p. 232°–233° C. (dec.)].

Anal. calc'd. for $C_{22}H_{27}N_4O_6F_3$: C, 52.80; H, 5.44; N, 11.20. Found: C, 52.64; H, 5.54; N, 11.19.

EXAMPLE 4

3S-[[[1-[4-(aminoiminomethyl)phenyl]-2-oxo-3-pyrrolidinyl]acetyl]amino]-4-pentenoic acid, monohydrochloride, enantiomerically enriched isomer A.

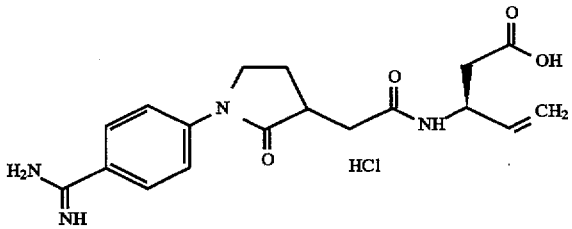

The title compound was prepared from the product of the previous example (250 mg, 0.50 mmol) in a manner similar to example 2 affording 182 mg (92%) of product [m.p. 113°–115° C. (dec.)].

Anal. calc'd. for $C_{18}H_{23}N_4O_4Cl \cdot 1/2H_2O$: C, 53.53, H, 5.99, N, 13.87. Found: C, 53.78; H, 6.22; N, 13.47.

EXAMPLE 5

Ethyl 3S-[[[1-[4-(aminoiminomethyliphenyl]-2-oxo-3-pyrrolidinyl]acetyl]amino]-4-pentenoate, enantiomerically enriched isomer B

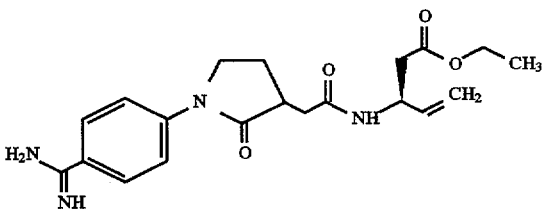

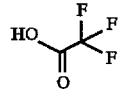

A. Preparation of (+)-1-(4-cyanophenyl)-2-pyrrolidinone-3-acetic acid.

The title compound was prepared from the product of example 1, step D (1.93 g, 7.91 mmol) in a manner similar to example 2, step A, substituting (R)-(+)-α-methylbenzylamine for (S)-(−)-α-methylbenzylamine affording 640 mg of chiral salt ($[\alpha]_D^{25}=+37.3°$, MeOH) (m.p. 171°–174° C.). The free acid was liberated upon partitioning between EtOAc and dilute HCl ($[\alpha]_D^{25}=+29.3°$, MeOH) (m.p 190°–191.5° C.). The enantiomeric excess (82% e.e.) was determined by chiral HPLC analysis on a chiralpak:-OD-R column using 30/70 acetonitrile/0.05M Na perchlorate, 2.5 pH (flow rate=0.5 mL/min).

B. Preparation of [1-(4-cyanophenyl)-2-oxo-3-pyrrolidinyl]acetyl-(3S)vinyl-β-alanine ethyl ester, enantiomerically enriched isomer B The title compound was prepared from the product of step A (365 mg, 1.50 mmol) in a manner similar to example 1, step E affording 450 mg (81%) of product after recrystallization from $CH_2Cl_2$/methyl t-butyl ether (m.p. 130°–131° C.) ($[\alpha]_D^{25}=+46.9°$, $CHCl_3$).

Anal. calc'd. for $C_{20}H_{23}N_3O_4$: C, 65.02; H, 6.28; N, 11.38. Found: C, 65.09; H, 6.31; N, 11.37.

C. Ethyl 3S-[[[1-[4-(aminoiminomethyl)phenyl]-2-oxo-3-pyrrolidinyl]acetyl]amino]-4-pentenoate, enantiomerically enriched isomer B The title compound was prepared from the product of step B (500 mg, 1.22 mmol) in a manner similar to example 1, step F affording 310 mg (51%) of product as the TFA salt following reverse phase chromatography [m.p. 217°–218° C. (dec.)].

Anal. calc'd. for $C_{22}H_{27}N_4O_6F_3$: C, 52.80; H, 5.44; N, 11.20. Found: C, 52.55; H, 5.44; N, 11.06.

EXAMPLE 6

3S-[[[1-[4-(aminoiminomethyl)phenyl]-2-oxo-3-pyrrolidinyl]acetyl]amino]-4-pentenoic acid, enantiomerically enriched isomer B

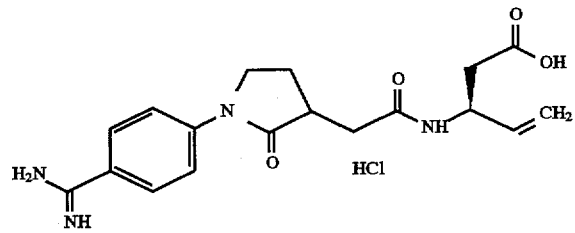

The title compound was prepared from the product of example 5, step C (125 mg, 0.25 mmol) in a manner similar to example 2 affording 72 mg (73%) of product [m.p. 135°–137° C. (dec.)].

Anal. calc'd. for $C_{18}H_{23}N_4O_4Cl.1.33\ H_2O$: C, 51.62, H, 6.18, N, 13.38. Found: C, 51.85; H, 5.83; N, 13.67.

EXAMPLE 7

Ethyl 3-[[[1-[4-(aminoiminomethyl)phenyl]-2-oxo-3-pyrrolidinyl]acetyl]amino]propionate

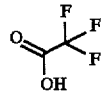

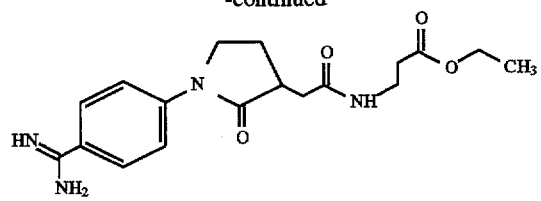

A. Preparation of 1-[4-(thiocarboxamido)phenyl]-2-pyrrolidinone-3-acetic acid.

Hydrogen sulfide was bubbled through a solution of the product of example 1, step D (2.25 g, 9.20 mmol) and triethylamine (5.57 g, 55.2 mmol) in 12 mL of pyridine at room temperature for 5 minutes. The reaction was stoppered and stirred at room temperature overnight. The solution was poured into dilute HCl and the yellow precipitate was filtered, washed with water and dried affording 2.40 g (94%) of yellow product used directly in the next reaction: H NMR ($d_6$-DMSO) δ1.86 (m, 1H), 2.34 (m, 1H), 2.47 (m, 1H), 2.69 (m, 1H), 2.97 (m, 1H), 3.82 (m, 2H), 7.73 (d, J=8 Hz, 2H), 7.98 (d, J=8 Hz, 2H), 9.53 (br. s, 1H), 9.76 (br. s, 1H).

B. Preparation of 3-[[[1-[4-(thiocarboxamido)phenyl]-2-oxo-3-pyrrolidinyl]acetyl]amino]propionic acid The title compound was prepared from the product of step A (500 mg, 1.8 mmol) in a manner similar to example 1, step E, substituting ethyl β-alanine hydrochloride for ethyl (3S)-vinyl-β-alanine hydrochloride affording 440 mg (65%) of product: H NMR ($d_6$-DMSO) δ1.19 (t, J=7 Hz, 3H), 1.78 (m, 1H), 2.25 (m, 2H), 2.46 (t, J=7 Hz, 2H), 2.58 (m, 1H), 2.93 (m, 1H), 3.29 (m, 2H), 3.80 (m, 2H), 4.07 (q, J=7 Hz, 2H), 7.72 (d, J=8 Hz, 2H), 7.97 (d, J=8 Hz, 2H).

C. Preparation of Ethyl 3-[[[1-[4-(aminoiminomethyl)phenyl]-2-oxo-3-pyrrolidinyl]acetyl]amino]propionate The title compound was prepared from the product of step B of this example (400 mg, 1.06 mmol) in a manner similar to example 1, step F affording 260 mg (52%) of product as the TFA salt following reverse phase chromatography:H NMR ($d_6$-DMSO) δ1.19 (t, J=7 Hz, 3H), 1.81 (m, 1H), 2.29 (m, 2H), 2.46 (t, J=7 Hz, 2H), 2.58 (m, 1H), 2.98 (m, 1H), 3.28 (m, 2H), 3.83 (m, 2H), 4.07 (q, J=7 Hz, 2H), 7.87 (d, J=8 Hz, 2H), 7.93 (d, J=8 Hz, 2H).

Anal. calc'd. for $C_{20}H_{25}N_4O_6F_3.0.25\ H_2O$: C, 50.16; H, 5.37; N, 11.70. Found: C, 50.02; H, 5.22; N, 11.51.

EXAMPLE 8

3-[[[1-[4-(aminoiminomethyl)phenyl]-2-oxo-3-pyrrolidinyl]acetyl]amino]propionic acid

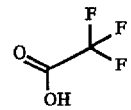

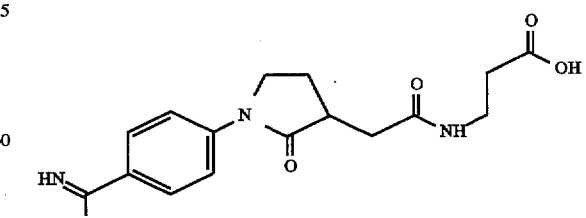

The title compound was prepared from the product of step C of example 7 (100 mg, 0.21 mmol) in a manner similar to example 2 affording 60 mg (64%) of product following reverse phase chromatography: H NMR (d$_6$-DMSO) δ1.81 (m, 1H), 2.28 (m, 2H), 2.39 (t, J=7 Hz, 2H), 2.58 (m, 1H), 2.96 (m, 1H), 3.25 (m, 2H), 3.83 (m, 2H), 7.85 (d, J=8 Hz, 2H), 7.92 (d, J=8 Hz, 2H).

Anal. calc'd. for C$_{18}$H$_{21}$N$_4$O$_6$F$_3$.0.25 H$_2$O: C, 47.95; H, 4.81; N, 12.43. Found: C, 47.82; H, 4.84; N, 12.21.

EXAMPLE 9

Ethyl 3-[[[1-[4-(aminoiminomethyl)phenyl]-2-oxo-3-pyrrolidinyl]acetyl]amino]butanoate

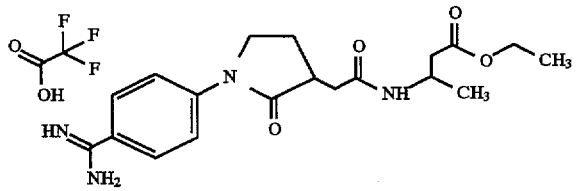

A. Preparation of Ethyl 3-[[[1-[4-(thiocarboxamido)phenyl]-2-oxo-3-pyrrolidinyl]acetyl]amino]butanoate The title compound was prepared from the product of example 7, step A in a manner similar to example 7, step B, substituting 3-methyl-β-alanine ethyl ester hydrochloride (260 mg, 1.54 mmol) for β-alanine ethyl ester hydrochloride affording 410 mg (75%) of product: H NMR (d$_6$-DMSO) δ1.09 (m, 3H), 1.18 (t, J=7 Hz, 3H), 1.78 (m, 1H), 2.15–2.61 (m, 4H), 2.93 (m, 1H), 3.80 (m, 2H), 4.00–4.17 (m, 3H), 7.72 (d, J=8 Hz, 2H), 7.97 (d, J=8 Hz, 2H).

B. Preparation of Ethyl 3-[[[1-[4-(aminoiminomethyl)phenyl]-2-oxo-3-pyrrolidinyl]acetyl]amino]butanoate The title compound was prepared from the product of step A of this example (400 mg, 1.03 mmol) in a manner similar to example 1, step F affording 180 mg (36%) of product as the TFA salt following reverse phase chromatography: H NMR (d$_6$-DMSO) δ1.09 (m, 3H), 1.18 (t, J=7 Hz, 3H), 1.81 (m, 1H), 2.20–2.60 (m, 4H), 2.96 (m, 1H), 3.83 (m, 2H), 4.05 (q, J=7 Hz, 2H), 4.05 (q, J=7 Hz, 2H), 4.10 (m, 1H), 7.85 (d, J=8 Hz, 2H), 7.92 (d, J=8 Hz, 2H).

Anal. calc'd. for C$_{21}$H$_{27}$N$_4$O$_6$F$_3$: C, 51.64; H, 5.57; N, 11.47. Found: C, 51.67; H, 5.65; N, 11.36.

EXAMPLE 10

3-[[[-[4-(aminoiminomethyl)phenyl]-2-oxo-3-pyrrolidinyl]acetyl]amino]butanoic acid

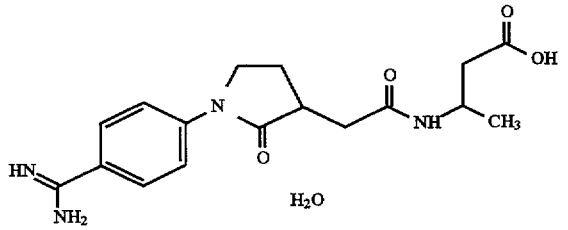

The title compound was prepared from the product of step B of example 9 (100 mg, 0.21 mmol) in a manner similar to example 2 affording 55 mg (58%) of product following reverse phase chromatography: H NMR (d$_6$-DMSO) δ1.09 (m, 3H), 1.72 (m, 1H), 2.20–2.60 (m, 4H), 2.96 (m, 1H), 3.83 (m, 2H), 4.08 (m, 1H), 7.85 (d, J=8 Hz, 2H), 7.92 (d, J=8 Hz, 2H).

Anal. calc'd. for C$_{17}$H$_{22}$N$_4$O$_4$1.2TFA.H$_2$O: C, 46.49; H, 5.07; N, 11.18. Found: C, 46.75; H, 4.81; N, 10.92.

EXAMPLE 11

Ethyl 3-[[[1-[4-(aminoiminomethyl)phenyl]-2-oxo-3-pyrrolidinyl]acetyl]amino]-3-phenylpropionate

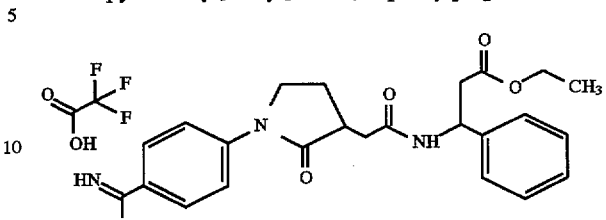

A. Preparation of Ethyl 3-[[[1-[4-(thiocarboxamido)phenyl]-2-oxo-3-pyrrolidinyl]acetyl]amino]-3-phenylpropionate The title compound was prepared from the product of example 7, step A in a manner similar to example 7, step B, substituting 3-phenyl-β-alanine ethyl ester hydrochloride (355 mg, 1.54 mmol) for β-alanine ethyl ester hydrochloride affording 460 mg (73%) of product: H NMR (d$_6$-DMSO) δ1.13 (t, J=7 Hz, 3H), 1.78 (m, 1H), 2.15–2.45 (m, 2H), 2.63 (m, 1H), 2.75 (d, J=8 Hz, 2H), 2.93 (m, 1H), 3.78 (m, 2H), 4.02 (m, 2H), 5.24 (m, 2H), 7.20–7.38 (m, 5H), 7.72 (d, J=8 Hz, 2H), 7.97 (d, J=8 Hz, 2H).

B. Preparation of Ethyl 3-[[[1-[4-(aminoiminomethyl)phenyl]-2-oxo-3-pyrrolidinyl]acetyl]amino]-3-phenylpropionate The title compound was prepared from the product of step A of this example (450 mg, 0.99 mmol) in a manner similar to example 1, step F affording 250 mg (46%) of product as the TFA salt following reverse phase chromatography: H NMR (d$_6$-DMSO) δ1.13 (t, J=7 Hz, 3H), 1.79 (m, 1H), 2.15–2.40 (m, 2H), 2.63 (m, 2.66 (d, J=8 Hz, 2H), 2.95 (m, 1H), 3.80 (m, 2H), 4.03 (q, J$^{=7}$ Hz, 2H), 5.24 (m, 2H), 7.20–7.38 (m, 5H), 7.87 (d, J$^{=8}$ Hz, 2H), 7.90 (d, J=8 Hz, 2H).

Anal. calc'd. for C$_{26}$H$_{29}$N$_4$O$_6$F$_3$.0.5 H$_2$O: C, 55.81; H, 5.40; N, 10.01. Found: C, 56.00; H, 5.33; N, 9.97.

EXAMPLE 12

3-[[[1-[4-(aminoiminomethyl)phenyl]-2-oxo-3-pyrrolidinyl]acetyl]amino]-3-phenylpropionic acid

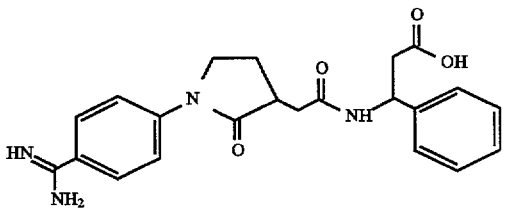

The title compound was prepared from the product of step B of example 11 (100 mg, 0.21 mmol) in a manner similar to example 2 affording 53 mg (56%) of product following reverse phase chromatography: H NMR (400 MHz, d$_6$-DMSO) δ1.80 (m, 1H), 2.15–2.45 (m, 2H), 2.63 (m, 1H), 2.68 (d, J=8 Hz, 2H), 2.95 (m, 1H), 3.80 (m, 2H), 5.22 (m, 2H), 7.20–7.38 (m, 5H), 7.84 (d, J=8 Hz, 2H), 7.91 (d, J=8 Hz, 2H).

Anal. calc'd. for C$_{22}$N$_{24}$N$_4$O$_4$.1.3 TFA.H$_2$O: C, 51.41; H, 4.79; N, 9.75. Found: C, 51.21; H, 4.53; N, 9.49.

EXAMPLE 13

Ethyl 3(S)-[[[1-[4-(aminoiminomethyl)phenyl]-2-oxo-3-pyrrolidinyl]acetyl]amino]-4-pentynoate

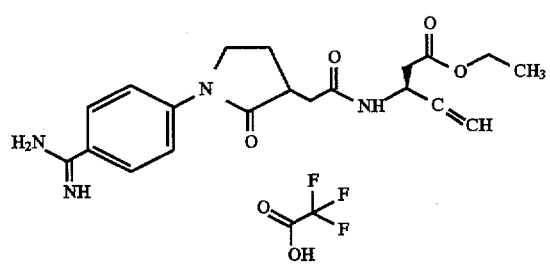

A. Preparation of Ethyl 3(S)-[[[1-[4-(cyanophenyl)]-2-oxo-3-pyrrolidinyl]acetyl]amino]-4-pentynoate The title compound was prepared in a manner similar to example 1, step E substituting [(3S)-ethynyl]-β-alanine ethyl ester hydrochloride (250 mg, 1.41 mmol) for [(3S)-vinyl]-β-alanine ethyl ester hydrochloride affording 450 mg (87%) of product: H NMR (CDCl$_3$) δ1.27 (m, 3H), 1.96 (m, 1H), 2.27 (m, 1H), 2.42–2.58 (m, 2H), 2.63–2.85 (m, 3H), 3.08 (m, 1H), 3.83 (m, 2H), 4.18 (m, 2H), 5.12 (m, 1H), 7.64 (d, J=8 Hz, 2H), 7.80 (d, J=8 Hz, 2H).

Anal. calc'd. for C$_{20}$N$_{21}$N$_3$O$_4$: C, 65.38; H, 5.76; N, 11.41. Found: C, 65.13; H, 6.15; N, 11.34.

B. Preparation of Ethyl 3(S)-[[[1-[4-(aminoiminomethyl)phenyl]-2-oxo-3-pyrrolidinyl]acetyl]amino]-4-pentynoate The title compound was prepared from the product of step A (135 mg, 0.40 mmol) in a manner similar to example 1, step F affording 85 mg (43%) of product as the TFA salt following reverse phase chromatography: H NMR (d$_6$-DMSO) δ1.18 (m, 3H), 1.71 (m, 1H), 2.24–2.38 (m, 2H), 2.53–2.64 (m, 3H), 2.98 (m, 1H), 3.23 (m, 1H), 3.83 (m, 2H), 4.05 (m, 2H), 4.85 (m, 1H), 7.86 (d, J=8 Hz, 2H), 7.93 (d, J=8 Hz, 2H).

EXAMPLE 14

3(S)-[[[1-[4-(aminoiminomethyl)phenyl]-2-oxo-3-pyrrolidinyl]acetyl]amino]-4-pentynoic acid

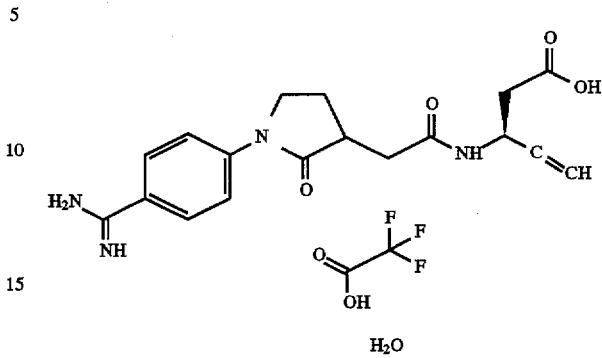

The title compound was prepared from the product of step B (50 mg, 0.10 mmol) in a manner similar to example 2 affording 35 mg (74%) of product following reverse phase chromatography: m.p. 200°–203° (dec.); H NMR (d$_6$-DMSO) δ1.71 (m, 1H), 2.24–2.38 (m, 2H), 2.53–2.64 (m, 3H), 2.98 (m, 1H), 3.23 (m, 1H), 3.83 (m, 2H), 4.85 (m, 1H), 7.86 (d, J=8 Hz, 2H), 7.93 (d, J=8 Hz, 2H).

Anal. calc'd. for C$_{20}$H$_{21}$N$_4$O$_6$F$_3$.1 H$_2$O: C, 50.10; H, 4.63; N, 11.69. Found: C, 50.01; H, 4.53; N, 11.57.

EXAMPLE 15

3-[[[1-[4-(aminoiminomethyl)phenyl]-2-oxo-3-pyrrolidinyl]acetyl]amino-N-[(phenylmethoxy)carbonyl]-L-alanine, ethyl ester

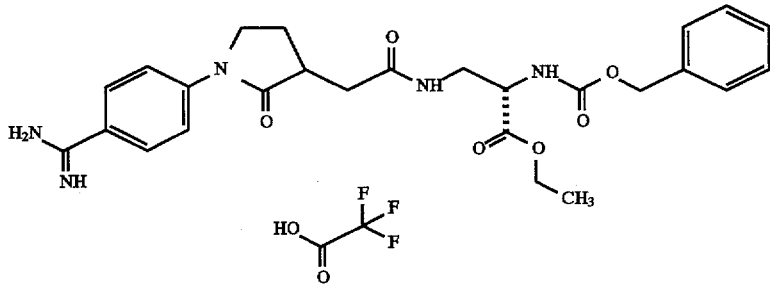

A. Preparation of ethyl 3-amino-(2S)-(phenylmethoxycarbonylamino)propionate hydrochloride.

To a solution of N$_\alpha$-Z-L-2,3-diaminopropionic acid (2.00 g, 8.40 mmol) in 30 mL of saturated HCl/EtOH was stirred at room temperature overnight. The solvent was removed and the residue was triturated with Et$_2$O affording 2.4 g (96%) of product: H NMR (CD$_3$OD) δ1.24 (t, J=7 Hz, 3H), 3.24 (dd, J=8.13 Hz, 1H), 3.45 (dd, J=5.13 Hz, 1H), 4.22 (q, J=8 Hz, 2H), 4.48 (m, 1H), 5.14 (s, 2H), 7.28–7.41 (m, 5H).

B. Preparation of 3(S) -[[[1-[4 -cyanophenyl]-2 -oxo-3-pyrrolidinyl]acetyl]amino]-N-[(phenylmethoxy)carbonyl]-L-alanine, ethyl ester The title compound was prepared from the product of step A (530 mg, 1.76 mmol) in a manner similar to example 1, step E affording 665 mg (85%) of product. H NMR (CDCl$_3$) δ1.28, (t, J=7 HZ, 3H), 1.92 (m, 1H), 2.45 (m, 2H), 2.68 (m, 2H), 3.04 (m, 1H), 3.68 (m, 2H), 3.79 (m, 2H), 4.18 (m, 2H), 4.43 (m, 1H), 5.09 (m, 2H), 7.35 (m, 5H), 7.57 (m, 2H), 7.78 (m, 2H).

C. Preparation of 3(S)-[[[1-[4-(aminoiminomethyl)phenyl]-2-oxo-3-pyrrolidinyl]acetyl]amino]-N-[(phenylmethoxy)carbonyl]-L-alanine, ethyl ester The title compound was prepared from the product of step B of this example (650 mg, 1.32 mmol) in a manner similar to example 1, step F affording 400 mg (48%) of product as the TFA salt following reverse phase chromatography.

Anal. calc'd. for $C_{28}N_{32}N_5O_8F_3 \cdot 1/2H_2O$: C, 53.16; H, 5.26; N, 11.07. Found: C, 53.12; H, 5.09; N, 10.99.

EXAMPLE 16

3-[[[1-[4-(aminoiminomethyl)phenyl]-2-oxo-3-pyrrolidinyl]acetyl]amino]-N-[(phenylmethoxy)carbonyl]-L-alanine

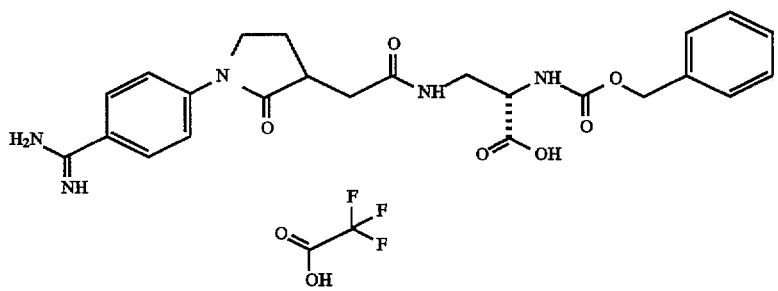

The title compound was prepared from the product of step C of example 14 (100 mg, 0.16 mmol) in a manner similar to example 2 affording 62 mg (64%) of product following reverse phase chromatography H NMR ($d_6$-DMSO) δ1.88 (m, 1H), 2.30–2.45 (m, 2H), 2.73 (m, 1H), 3.03 (m, 1H), 3.47 (m, 1H), 3.73 (m, 1H), 3.83 (m, 2H), 4.38 (m, 1H), 5.09 (m, 2H), 7.20–7.39 (m, 5H), 7.81 (d, J=8 Hz, 2H), 7.93 (d, J=8 Hz, 2H).

Anal. calc'd. for $C_{26}H_{28}N_5O_8F_3 1.5H_2O$: C, 50.16; H, 5.02; N, 11.20. Found: C, 50.18; H, 4.89; N, 10.79.

EXAMPLE 17

Ethyl 3(S)-[[[[1-[4-(aminoiminomethyl)phenyl]-2-oxo-3-pyrrolidinyl]amino]carbonyl]amino]-4-pentenoate

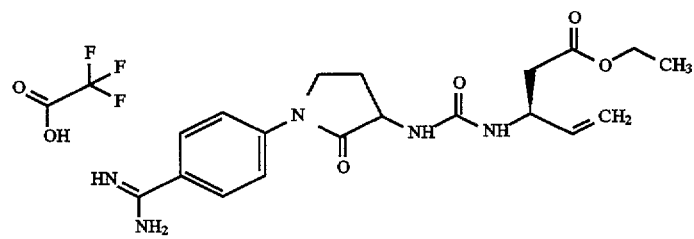

A. Preparation of 3-[(1,1-dimethyl)ethoxycarbonylamino]-tetrahydrofuran-2-one.

To a solution of α-amino-γ-butyrolactone hydrobromide (1.82 g, 10 mmol) in 5 mL of $H_2O$ was added sequentially, $Boc_2O$ (in 10 mL of dioxane) and N-methylmorpholine (1.01 g, 10 mmol). The reaction was stirred at room temperature for 3 hours, acidified with 2N HCl, diluted with saturated NaCl and extracted with EtOAc. The organic layed was dried (MgSO₄) and concentrated. Trituration of the residue with hexane gave 1.85 g (92%) of product (m.p. 113°–114.5° C.).

Anal.calc'd. for $C_9N_{15}NO_4$: C, 53.72; H, 7.51; N, 6.96. Found: C, 53.48; H, 7.70; N, 6.85.

B. Preparation of N-(4-cyanophenyl)-4-hydroxy-2-[(1,1-dimethyl)ethoxycarbonylamino]butanamide To a solution of the product of step A (1.52 g, 7.56 mmol) and aminobenzonitrile (892 mg, 7.56 mmol) in THF (20 mL) was added LiHMDS (15 mL of a 1M soln. in THF, 15 mmol) and stirred at room temperature for 30 minutes. The solution was poured into dilute HCl and extracted (2×) with EtOAc, washed with saturated NaCl, dried (MgSO₄) and concentrated. Silica gel chromatography of the residue (3:1 EtOAc/hexane, then EtOAc) afforded 2.45 g (90%) of product: H NMR (CDCl₃) δ1.47 (s, 9H), 1.87 (m, 1H), 2.16 (m, 1H), 3.86 (m, 2H), 4.54 (m, 1H), 7.61 (d, J=8 Hz, 2H), 7.69 (d, J=8 Hz, 2H).

C. Preparation of 3-amino-1-(4-cyanophenyl)-2-pyrrolidinone hydrochloride.

To a solution of the product of step B (2.36 g, 7.40 mmol) and triphenylphosphine (2.13 g, 8.14 mmol) in dry THF (30 mL) at −40° C. under nitrogen was added diethylazodicarboxylate (1.48 g, 8.51 mmol). The ice bath was removed and the solution was stirred at ambient temperature for 1 hour. The reaction was concentrated and redissolved in EtOAc (70 mL). Dry HCl gas was bubbled through the solution for 5 minutes at room temperature and the solution stirred for an additional 45 minutes. The resulting precipitate was filtered, washed with EtOAc and dried affording 1.50 g (85%) of product: H NMR (CDCl₃/CD₃OD) δ2.33 (m, 1H), 2.81 (m, 1H), 3.97 (m, 2H), 4.23 (m, 1H), 7.73 (d, J=8 Hz, 2H), 7.86 (d, J=8 Hz, 2H).

Anal.calc'd. for $C_{11}H_{12}N_3OCl 0.33 H_2O$: C, 54.23; H, 5.24; N, 17.25. Found: C, 54.65; H, 5.19; N, 17.25.

The product was converted to the free base by partitioning between saturated NaHCO₃ and EtOAc, concentrated and used directly in the next reaction.

D. Preparation of [1-(4-cyanophenyl)-2-pyrrolidinone-3-aminocarbonyl]-[(3S)vinyl]-β-alanine.

To a solution of triphosgene (42 mg, 0.14 mmol) in 1,2-dichloroethane (1 mL) was added a solution of the product of step C (85 mg, 0.42 mmol) and diisopropylethylamine (108 mg, 0.84 mmol) in 1,2-dichloroethane (2 mL). After stirring at ambient temperature for 30 minutes, solid (3S)-vinyl-β-alanine hydrochloride (76 mg, 0.42 mmol) and neat diisopropylethylamine (54 mg, 0.42 mmol) were added sequentially. The reaction was stirred at 65° C. for 2 hours, poured into dilute HCl and extracted with EtOAc. The organic fraction was dried (MgSO$_4$), filtered through a bed of silica gel (EtOAc) and concentrated. Trituration and filtration of the residue from Et$_2$O gave 110 mg (70%) of product (m.p. 113°–115° C.).

Anal.calc'd. for $C_{19}H_{22}N_4O_4$: C, 61.61; H, 5.99; N, 15.13. Found: C, 61.60; H, 5.62; N, 15.21.

E. Preparation of Ethyl 3S-[[[[1-[4-(aminoiminomethyl) phenyl]-2-oxo-3-pyrrolidinyl]amino]carbonyl]amino]-4-pentenoate The title compound was prepared from the product of step D (440 mg, 1.19 mmol) in a manner similar to example 1, step F affording 306 mg (59%) of product [m.p. 203°–205° C. (dec.)]: $^1$H-NMR (300 MHz, d$_6$-DMSO) δ1.18 (t, J=7 Hz, 3H), 1.96 (m, 1H), 2.35–2.55 (m, 3H), 3.80 (m, 2H), 4.06 (q, J=7 Hz, 2H), 4.39–4.56 (m, 2H), 5.03–5.18 (m, 2H), 5.84 (m, 1H), 7.87 (d, J=8 Hz, 2H), 7.92 (d, J=8 Hz, 2H).

EXAMPLE 18

3(S)-[[[[1-[4-(aminoiminomethyl)phenyl]-2-oxo-3-pyrrolidinyl]amino]carbonyl]amino]-4-pentenoic acid

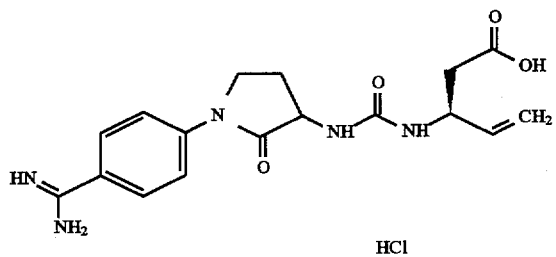

HCl

The title compound was prepared from the product of example 17, step E (280 mg, 0.56 mmol) in a manner similar to example 2 affording 160 mg (72%) of product as the HCl salt [m.p. 185°–187° C. (dec.)].

Anal.calc'd. for $C_{17}H_{22}N_5O_4Cl·1.1H_2O$: C, 49.12; H, 5.87; N, 16.85. Found: C, 49.01; H, 5.76; N, 16.41.

EXAMPLE 19

1-[4-(aminoiminomethyl)phenyl]-βS-methyl-2-oxo-3-pyrrolidinehexanoic acid, monohydrochloride.

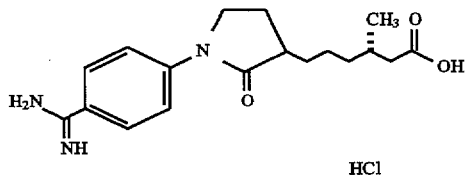

HCl

A. Preparation of [3(S),7-dimethyloct-6-enyloxy](1,1-dimethylethyl)(dimethyl)silane.

Solid TBDMSCl (5.06 g, 33.65 mmol) was added to a stirred solution of (S)-(−)-β-citronellol (5.0 g, 32 mmol) [Aldrich, [α]$_D^{20}$=−5.3° (neat)] and imidazole (4.60 g, 67.31 mmol) in 5 mL of DMF. After stirring at room temperature overnight, the reaction was diluted with water, extracted with hexane, dried (MgSO$_4$), and concentrated affording 9.0 g (104%) of crude product used directly in the next reaction. H—NMR (CDCl$_3$) δ0.06 (s, 6H), 0.90 (m, 12H), 1.17 (m, 1H), 1.31 (m, 2H), 1.56 (m, 2H), 1.61 (s, 3H), 1.69 (s, 3H), 1.99 (m, 2H), 3.65 (m, 2H), 5.11 (m, 1H).

B. Preparation of [6-hydroxy-[3(S)-methylhexyl]oxy](1,1-dimethylethyl) (dimethyl)silane.

Ozone was bubbled through a solution of the product of step A (32 mmol) in 30 mL of CH$_2$Cl$_2$/MeOH (1:1) at −78° C. until a blue color persisted then oxygen was bubbled through until the blue color dissipated. Solid NaBH$_4$ (3.0 g, 80 mmol) was added and the reaction was stirred at 0° C. for 1 hour then at room temperature for 1 hour. The reaction was poured into dilute HCl, extracted with EtOAc, washed with saturated NaCl, dried (MgSO$_4$) and concentrated affording 8.30 g (105%) of crude product used directly in the next reaction: H NMR (CDCl$_3$) δ0.06 (s, 6H), 0.90 (m, 12H), 1.19 (m, 1H), 1.56 (m, 4H), 3.64 (m, 4H).

C. Preparation of [6-iodo-[3(S)-methylhexyl]oxy](1,1-dimethylethyl) (dimethyl)silane.

Solid I$_2$ (2.79 g, 11 mmol) was added portionwise to a stirred solution of the product of step B (2.46 g, 10 mmol), imidazole (748 mg, 11 mmol) and triphenylphosphine (2.75 g, 10.5 mmol) in dry THF (30 mL). After 30 minutes, an additional 0.5 equivalents of each reagent was added in order for the reaction to reach completion. After 30 minutes, the reaction mixture was diluted with hexane (60 mL) and filtered through a bed of silica gel using Et$_2$O/hexane (2:1) as eluent (300 mL). Removal of the solvent afforded 2.70 g (76%) of product. H-NMR (CDCl$_3$) δ0.04 (s, 6H), 0.90 (m, 12H), 1.18–1.45 (m, 3H), 1.58 (m, 2H), 1.86 (m, 2H), 3.64 (m, 2H).

D. Preparation of [1-(4-cyanophenyl)-γS-methyl-2-oxo-3-pyrrolidinehexyloxy](1,1-dimethylethyl)(dimethyl)silane.

To a solution of the product of example 1, step B (500 mg, 2.69 mmol) in 22 mL of THF/HMPA (10:1) was added LiHMDS (2.7 mL of a 1M sol. in THF, 2.7 mmol) at −75° C. under nitrogen. After 5 minutes, the product of step C (982 mg, 2.69 mmol) was added neat via syringe. The reaction was slowly warmed to room temperature over 2 hours, poured into dilute HCl, and extracted with EtOAc. The organic phase was washed with water, saturated NaCl, dried (MgSO$_4$) and concentrated. Silica gel chromatography (35% EtOAc/hexane) afforded 530 mg (48%) of product: H NMR (CDCl$_3$) δ0.04 (s, 6H), 0.89 (m, 12H), 1.18–1.68 (m, 8H), 1.77–2.00 (m, 2H), 2.37 (m, 1H), 2.63 (m, 1H), 3.64 (m, 2H), 3.79 (m, 2H), 7.65 (d, J=8 Hz, 2H), 7.80 (d, J=8 Hz, 2H).

E. Preparation of 1-(4-cyanophenyl)-γS-methyl-2-oxo-3-pyrrolidinehexanol

To a solution of the product of step D (530 mg, 1.28 mmol) in THF (5 mL) was added tetrabutylammonium fluoride (3.8 mL of a 1M soln. in THF 3.80 mmol). After stirring at room temperature for 3 hours, the reaction was diluted with EtOAc and washed successively with water (2×), saturated NaCl, dried (MgSO$_4$) and concentrated. Silica gel chromatography (CH$_2$Cl$_2$, then EtOAc) afforded 310 mg (81%) of product: H NMR (CDCl$_3$) δ0.92 (d, J=7 Hz, 3H), 1.18–1.52 (m, 7H), 1.77–2.00 (m, 2H), 2.37 (m, 1H), 2.63 (m, 1H), 3.68 (m, 2H), 3.79 (m, 2H), 7.65 (d, J=8 Hz, 2H), 7.80 (d, J=8. Hz, 2H).

F. Preparation of 1-(4-cyanophenyl)-βS-methyl-2-oxo-3-pyrrolidinehexanoic acid.

To a solution of Jones reagent (0.57 mL of a 2.67M solution, 1.53 mmol) in 5 mL of acetone was added slowly the product of step E (300 mg, 1 mmol) in 2 mL of acetone. After 30 minutes at ambient temperature, the reaction was diluted with EtOAc and washed with water, saturated NaCl, dried (MgSO$_4$) and concentrated affording 320 mg (100%) of product: H NMR (CDCl$_3$) δ1.00 (d, J=7 Hz, 3H), 1.18–1.55 (m, 5H), 1.77–2.05 (m, 3H), 2.19 (m, 1H), 2.32–2.43 (m, 2H), 2.63 (m, 1H), 3.79 (m, 2H), 7.65 (d, J=8 Hz, 2H), 7.80 (d, J=8 Hz, 2H).

G. Preparation of 1-[4-(aminoiminomethyl)phenyl]-βS-methyl-2-oxo-3-pyrrolidinehexanoic acid, monohydrochloride.

The title compound was prepared from the product of step F (314 mg, 1 mmol) in a manner similar to example 1, step F with the following modification to the workup. Follow removal of the solvent, the residue was treated with 1 mL of water followed by 15 mL of acetone and the zwitterionic product which precipitated was filtered and washed with acetone (80 mg). This material was converted to the HCl salt by suspending in 2 mL of MeOH and treating with 0.13 mL of 2N HCl. The resulting solution was evaporated and solidified upon trituration with acetone affording 50 mg (14%) of product [m.p. 103°–110° C. (dec.)].

Anal. calc'd. for C$_{18}$H$_{26}$N$_3$O$_3$Cl.0.33 H$_2$O: C, 57.83; H, 7.19; N, 11.24. Found: C, 58.07; H, 7.30; N, 10.73.

EXAMPLE 20

Ethyl 1-[4-(aminoiminomethyl)phenyl]-βS-methyl-2-oxo-3-pyrrolidinehexanoate, trifluoroacetate.

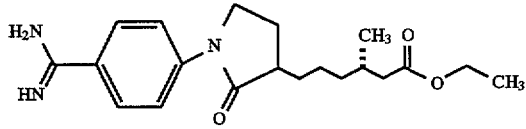

A. Preparation of ethyl 1-(4-cyanophenyl)-βS-methyl-2-oxo-3-pyrrolidinehexanoate.

To a solution of the product of example 19, step F (500 mg, 1.60 mmol) was added Cs$_2$CO$_3$ (779 mg, 2.39 mmol) and ethyl iodide (373 mg, 2.39 mmol) in 3 mL of DMF. After stirring at room temperature overnight the reaction was diluted with EtOAc and washed with water, saturated NaCl, dried (MgSO$_4$) and concentrated affording 510 mg (93%) of product: H NMR (CDCl$_3$) δ0.96 (d, J=7 Hz, 3H), 1.27 (m, 4H), 1.33–1.55 (m, 4H), 1.80–2.05 (m, 3H), 2.13 (m, 1H), 2.25–2.45 (m, 2H), 2.62 (m, 1H), 3.79 (m, 2H), 4.13 (q, J=7 Hz, 2H), 7.65 (d, J=8 Hz, 2H), 7.80 (d, J=8 Hz, 2H).

B. Preparation of ethyl 1-[4-(aminoiminomethyl)phenyl]-βS-methyl-2-oxo-3-pyrrolidinehexanoate, trifluoroacetate.

The title compound was prepared from the product of step A (510 mg, 1.49 mmol) in a manner similar to example 1, step F affording 287 mg (41%) of product as the TFA salt after reverse phase chromatography [m.p. 216°–218° C. (dec.)].

Anal. calc'd. for C$_{22}$H$_{30}$N$_3$O$_5$F$_3$: C, 55.80; H, 6.39; N, 8.87. Found: C, 55.89; H, 6.56; N, 8.87.

EXAMPLE 21

Ethyl 3-[[[1-[4-(aminoiminomethyl)phenyl]-2-oxo-3-piperidinyl]acetyl]amino]-5-(trimethylsilyl)-4-pentynoate

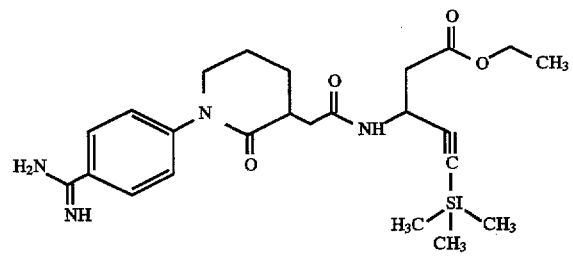

The title compound was prepared in the manner of Example 1 substituting ethyl 3-amino-5-trimethylsilylpent-4-ynoate for ethyl-3(S)-amino-4-pentenoate and 1-(4-cyanophenyl)-2-piperidone-3-acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of example 1 by substituting 5-bromovaleryl chloride for 4-bromobutyryl chloride in step A of example 1. The final product was purified by reverse phase HPLC using the conditions of Example 1 to afford the title compound. The product was verified by C NMR (CD$_3$OD) δ–1.0, 13.8, 22.7, 26.9, 37.6, 39.2, 40.7, 39.6, 51.6, 61.1, 70.6, 77.8, 119.0, 127.3, 128.4, 148.6, 166.6, 171.5, 171.6, 173.3.

EXAMPLE 22

3S-[[[1-[4-(aminoiminomethyl)phenyl]-2-oxo-3-piperidinyl]acetyl]amino]-5-(trimethylsilyl)-4-pentynoic acid

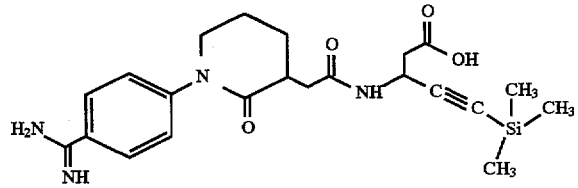

The title compound was prepared by treating the final product of the previous example with porcine liver esterase in the manner of Example 2. The product was purified by reverse phase HPLC using the conditions of Example 1 to afford the title compound. The product was verified by C NMR (CD$_3$OD) δ–1.6, 22.1, 26.2, 37.0, 38.5, 40.7, 39.1, 39.8, 51.0, 70.6, 77.8, 119.0, 126.7, 128.4, 148.5, 166.6, 171.5, 171.6, 173.3.

EXAMPLE 23

Ethyl 3-[[[1-[4-(aminoiminomethyl)phenyl]-2-oxo-3-piperidinyl]acetyl]amino]-4-pentynoate

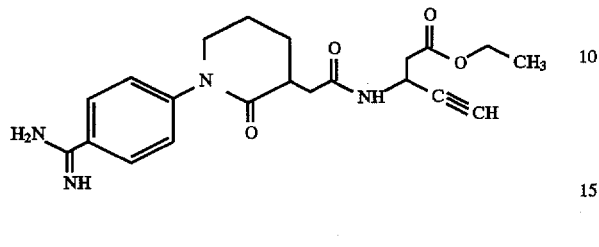

To a THF solution (30 mL) of the final product of example 21 (332 mg, 0.772 mmol) was added 2 equivalents of tetrabutylammonium fluoride (1.544 mmol of a 1M solution in THF) at 23° C. under argon. After 1 hour, the reaction mixture was concentrated in vacuo and purified by reverse phase HPLC as described in example step F to afford the title compound. The product was verified by C NMR (CD$_3$OD) $\delta$12.7, 21.7, 26.0, 36.7, 37.4, 38.7, 39.6, 50.7, 60.2, 70.9, 81.4, 126.1, 126.4, 128.1, 148.2, 166.8, 169.1, 171.0, 172.9.

EXAMPLE 24

3-[[[1-[4-(aminoiminomethyl)phenyl]-2-oxo-3-piperidinyl]acetyl]amino]-4-pentynoic acid.

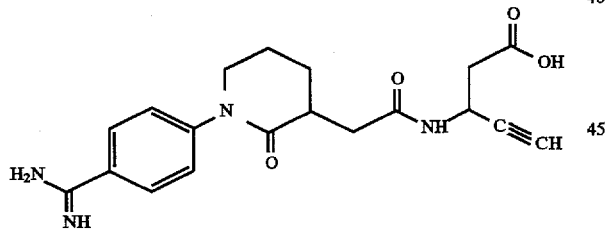

The title compound was prepared by treating the final product of the previous example with porcine liver esterase in the manner of Example 2. The product was purified by reverse phase HPLC using the conditions of Example 1 to afford the title compound. The product was verified by H NMR (CD$_3$OD) $\delta$1.63–1.94 (m, 2-CH$_2$), 2.48–2.78 (m, 2-CH$_2$), 3.52–3.71 (m, CH$_2$), 4.76–4.94 (m, CHN), 7.42–7.72 (m, PhH).

Anal. calc'd. for C$_{19}$N$_{22}$H$_4$O$_4$ plus 1.3 CF$_3$CO$_2$H.1.4 H$_2$O: C, 47.70; H, 4.84; N, 10.30. Found: C, 47.56; H, 4.53; N, 10.42.

EXAMPLE 25

Ethyl 3-[[[1-[4-(aminoiminomethyl)phenyl]-2-oxo-3-piperidinyl]acetyl]amino]-6,6-dimethyl-4-heptynoate

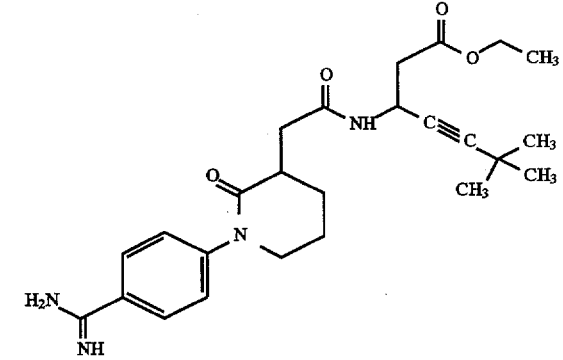

The title compound was prepared in the manner of Example 1 substituting ethyl 3-amino-6,6-dimethyl-4-heptynoate for ethyl (S)-3-amino-4-pentenoate. The product was purified by reverse phase HPLC using the conditions of Example 1 to afford the title compound. The product was verified by C NMR (CD$_3$OD) $\delta$12.4, 21.2, 25.4, 29.1, 36.3, 37.3, 38.3, 39.9, 50.2, 59.6, 75.6, 91.3, 125.3, 125.9, 127.6, 128.2, 166.7, 168.9, 171.6, 172.8.

EXAMPLE 26

3-[[[1-[4-(aminoiminomethyl)phenyl]-2-oxo-3-piperidinyl]acetyl]amino]-6,6-dimethyl-4-heptynoic acid

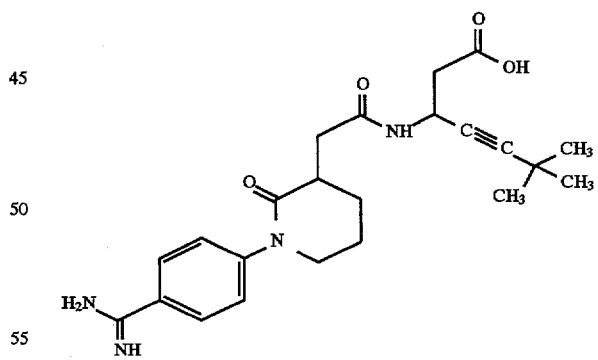

The title compound was prepared by treating the final product of the previous example with porcine liver esterase in the manner of Example 2. The product was purified by reverse phase HPLC using the conditions of Example 1 to afford the title compound. The product was verified by C NMR (CD$_3$OD) $\delta$20.7, 24.8, 28.6, 36.6, 37.6, 37.7, 39.1, 49.7, 75.6, 91.3, 125.1, 125.7, 127.4, 146.7, 166.7, 168.9, 171.6, 172.8.

EXAMPLE 27

Ethyl 3-[[[1-[4-(aminoiminomethyl)phenyl]-2-oxo-3-piperidinyl]acetyl]amino]-5-phenyl-4-pentynoate

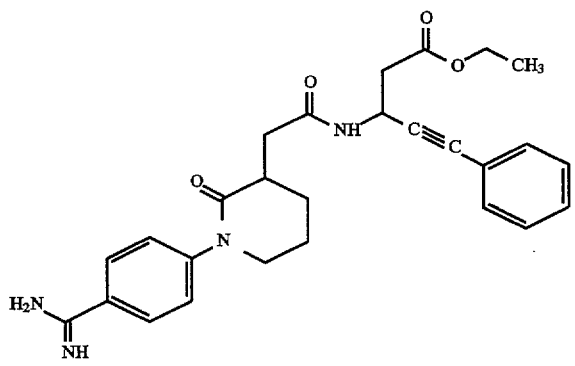

The title compound was prepared in the manner of Example 1 substituting ethyl 3-amino-5-phenyl-4-pentynoate for ethyl (S)-3-amino-4-pentenoate. The product was purified by reverse phase HPLC using the conditions of Example 1 to afford the title compound. The product was verified by C NMR (CD$_3$OD) δ13.8, 22.7, 27.0, 37.7, 39.1, 39.2, 39.7, 39.7, 40.7, 40.8, 51.7, 61.2, 82.8, 87.7, 123.7, 127.1, 127.3, 127.4, 128.7, 128.9, 129.0, 131.9, 149.2, 166.8, 170.4, 172.3, 173.9. FAB Mass Spectrometry (MH+)=475.

Anal. Calcd for $C_{27}H_{30}N_4O_4$ plus 1.2 $CF_3CO_2H$: C, 57.76; H, 5.14; N, 9.16. Found: C, 57.78; H, 4.80; N, 9.18.

EXAMPLE 28

3-[[[1-[4-(aminoiminomethyl)phenyl]-2-oxo-3-piperidinyl]acetyl]amino]-5-phenyl-4-pentynoic acid.

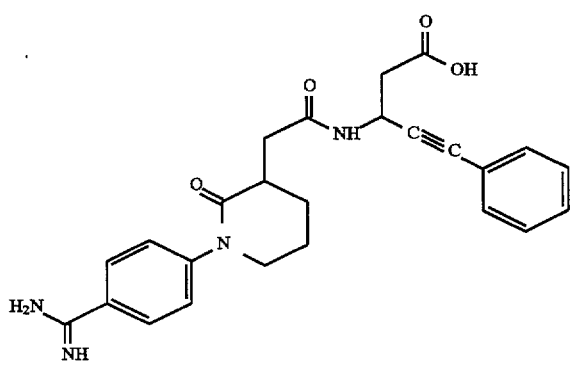

The title compound was prepared by treating the final product of the previous example with porcine liver esterase in the manner of Example 2. The product was purified by reverse phase HPLC using the conditions of Example 1 to afford the title compound. The product was verified by C NMR (CD$_3$OD) δ21.4, 25.6, 29.8, 34.9, 50.4, 81.3, 86.6, 121.8, 125.3, 126.0, 127.3, 127.5, 127.7, 130.6, 148.2, 166.7, 170.9, 171.2, 172.8.

Anal. Calc'd for $C_{25}H_{26}N_4O_4$ plus 1.0 $CF_3CO_2H$: C, 55.36; H, 5.13; N, 9.56. Found: C, 55.32; H, 4.94; N, 9.49.

EXAMPLE 29

Ethyl 3-[[[1-[4-(aminoiminomethyl)phenyl]-2-oxo-3-piperidinyl]acetyl]amino]-butanoate

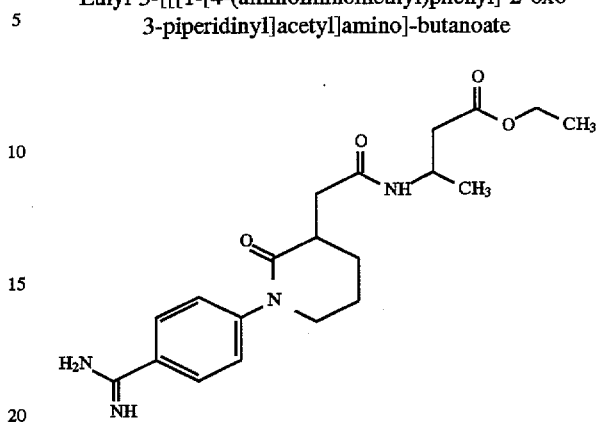

The title compound was prepared in the manner of Example 1 substituting ethyl 3-aminobutanoate for ethyl (S)-3-amino-4-pentenoate. The product was purified by reverse phase HPLC using the conditions of Example 1 to afford the title compound. The product was verified by C NMR (CD$_3$OD) δ13.8, 19.7, 22.7, 27.0, 38.0, 39.8, 41.1, 43.1, 51.7, 60.9, 127.1, 127.4, 129.1, 140.5, 166.8, 170.4, 172.3, 173.9.

Anal. Calc'd for $C_{20}N_{28}N_4O_4$ plus 1 $CF_3CO_2H$: C, 52.59; H, 5.82; N, 11.15. Found: C, 52.38; H, 6.13; N, 11.56.

EXAMPLE 30

3-[[[1-[4-(aminoiminomethyl)phenyl]-2-oxo-3-piperidinyl]acetyl]amino]-butanoic acid

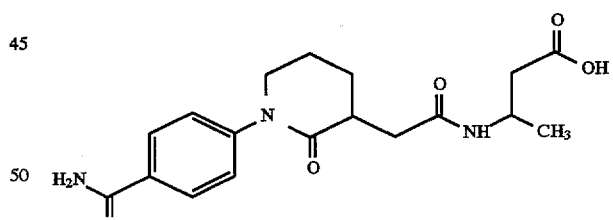

The title compound was prepared by treating the final product of the previous example with porcine liver esterase in the manner of Example 2. The product was purified by reverse phase HPLC using the conditions of Example 1 to afford the title compound. The product was verified by C NMR (CD$_3$OD) δ19.2, 22.2, 26.5, 37.4, 39.2, 40.3, 42.5, 51.2, 126.4, 126.9, 128.6, 140.5, 166.7, 170.9, 171.2, 172.8.

Anal. Calc'd for $C_{18}H_{24}N_4O_4$ plus 1 $CF_3CO_2H$ and 0.5 $H_2O$: C, 49.69; H, 5.42; N, 11.59. Found: C, 49.46; H, 4.95; N, 11.42.

EXAMPLE 31

Ethyl 3-[[[1-[4-(aminoiminomethyl)phenyl]-2-oxo-3-piperidinyl]acetyl]amino]-3-phenylpropanoate

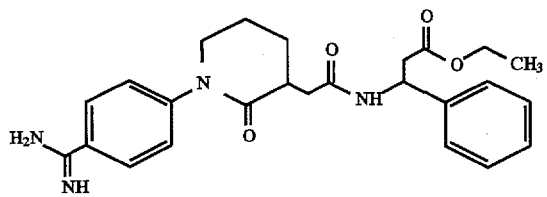

The title compound was prepared in the manner of Example 1 substituting ethyl 3-amino-3-phenylpropanoate for ethyl (S)-3-amino-4-pentenoate. The product was purified by reverse phase HPLC using the conditions of Example 1 to afford the title compound. The product was verified by C NMR (CD$_3$OD) δ12.5, 21.5, 25.8, 36.7, 38.6, 40.0, 49.7, 50.5, 59.9, 125.4, 125.7, 126.2, 126.7, 127.7, 127.9, 140.7, 148.0, 166.8, 170.3, 171.2, 172.4.

Anal. Calc'd for C$_{25}$H$_{30}$N$_4$O$_4$ plus 1 CF$_3$CO$_2$H and 0.5 H$_2$O: C, 56.54; H, 5.62; N, 9.77 Found: C, 56.86; H, 5.25; N, 9.92.

EXAMPLE 32

3-[[[1-[4-(aminoiminomethyl)phenyl]-2-oxo-3-piperidinyl]acetyl]amino]-3-phenylpropanoic acid

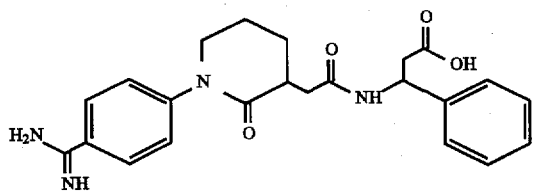

The title compound was prepared by treating the final product of the previous example with porcine liver esterase in the manner of Example 2. The product was purified by reverse phase HPLC using the conditions of Example 1 to afford the title compound. The product was verified by C NMR (CD$_3$OD) δ22.7, 26.8, 37.9, 39.8, 40.9, 50.8, 51.7, 126.5, 126.8, 126.9, 127.3, 127.4, 127.7, 128.8, 129.0, 141.8, 149.2, 166.8, 172.4, 173.0, 173.9.

Anal. Calc'd for C$_{23}$H$_{26}$N$_4$O$_4$ plus 1.1 CF$_3$CO$_2$H and 1.0 H$_2$O: C, 53.48; H, 5.18; N, 9.90 Found: C, 53.75; H, 4.78; N, 9.87.

EXAMPLE 33

Ethyl 3(S)-[[[1-[4-(aminoiminomethyl)phenyl]-2-oxo-3-piperidinyl]acetyl]amino]-4-pentenoate

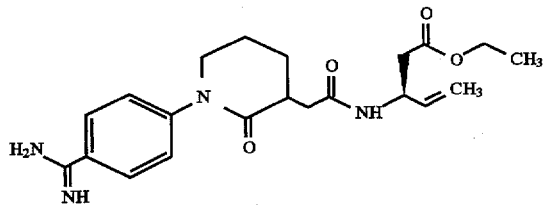

The title compound was prepared in the manner of example 1 substituting 1-(4-cyanophenyl)-2-piperidone-3-acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of example 1 by substituting 5-bromovaleryl chloride for 4-bromobutyryl chloride in step A of example 1. The final product was purified by reverse phase HPLC using the conditions of example 1 to afford the title compound. The product was verified by H NMR (CD$_3$OD, 2 diast.) δ1.11 (overlapping t, J=6 Hz, CH$_3$), 1.59–1.98 (m, 2 CH$_2$), 2.38–2.72 (m, 2-CH$_2$), 3.52–3.73 (m, CH$_2$), 3.96 (overlapping q, J=6 Hz), 4.64–4.74 (m, CHN), 4.95–5.14 (m, CH$_2$=). 5.67–5.80 (m, CH), 7.42 (d, J=8 Hz, PhH), 7.69 (d, J=8 Hz, PhH), 9.08 and 9.28 (2s, NH).

EXAMPLE 34

3(S)-[[[1-[4-(aminoiminomethyl)phenyl]-2-oxo-3-piperidinyl]acetyl]amino]-4-pentenoic acid.

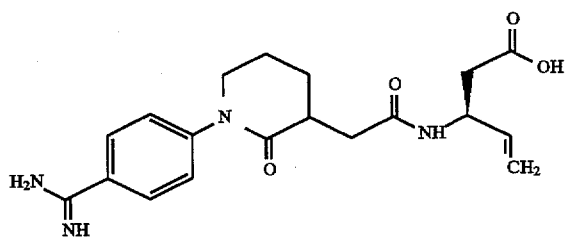

The title compound was prepared by treating the final product of the previous example with porcine liver esterase in the manner of Example 2. The product was purified by reverse phase HPLC using the conditions of Example 1 to afford the title compound. The product was verified by H NMR (CD$_3$OD) δ1.59–1.98 (m, 2 CH$_2$), 2.28–2.85 (m, 2-CH$_2$), 3.62–3.81 (m, CH$_2$), 4.59–4.74 (m, CHN), 5.03–5.19 (m, CH$_2$=). 5.67–5.91 (m, CH), 7.58 (d, J=8 Hz, PhH), 7.84 (d, J=8 Hz, PhH), 9.08 and 9.28 (2s, NH).

EXAMPLE 34A

Ethyl 3-[[[1-[4-(aminoiminomethyl)phenyl]-2-oxo-3-piperidinyl]acetyl]amino]propanoate, enantiomerically enriched isomer B

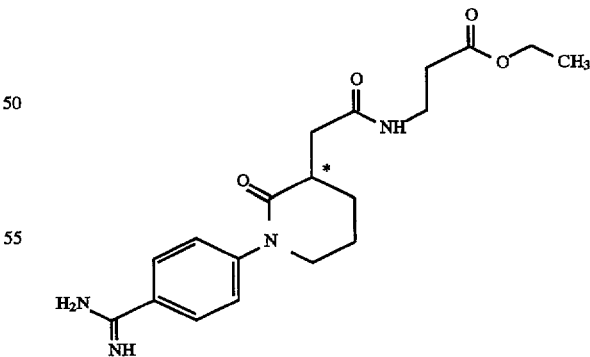

\* indicates single isomer at indicated stereocenter

The title compound was prepared in the manner of Example 1 substituting β-alanine for ethyl 3(S)-amino-4-pentenoate and 1-(4-cyanophenyl)-2-piperidone-3-acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of Example 1 by substituting 5-bromovaleryl chloride for 4-bromobutyryl chloride in step A of Example 1. The 1-(4-cyanophenyl)-2-piperidone-3-acetic acid was resolved in the same manner as the 1-(4-cyanophenyl)-2-pyrrolidinone-3-acetic acid in Example 5 and it had the following rotation ($[\alpha]_D^{25}$=+42.5°, C 0.521, MeOH). The final product was purified by reverse phase HPLC using the conditions of Example 1 to afford the title compound ($[\alpha]_D^{25}$=+30.9°, C 0.110, MeOH). The product was verified by C NMR (CD$_3$OD) δ13.7, 22.7, 26.9, 34.2, 35.6, 37.8, 39.7, 51.6, 60.9, 126.6, 127.3, 129.0, 148.6, 172.5, 173.3, 174.2.

Anal. Calc'd. for $C_{19}H_{26}N_4O_4$ plus 1.1 $CF_3CO_2H$ and 1.5 $H_2O$: C, 48.33; H, 5.76; N, 10.63. Found: C, 48.50; H, 5.40; N, 10.56.

EXAMPLE 34B

3-[[[1-[4-(aminoiminomethyl)phenyl]-2-oxo-3-piperidinyl]acetyl]amino]propanoic acid, enantiomerically enriched isomer B

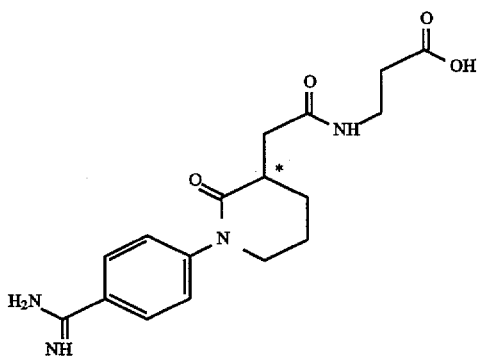

The title compound was prepared by treating the final product of the previous example with porcine liver esterase in the manner of Example 2. The product was purified by reverse phase HPLC using the conditions of Example 1 to afford the title compound ($[\alpha]_D^{25}$=+35.1°, c 0.163 MeOH) The product was verified by C NMR (CD$_3$OD) δ22.6, 26.9, 33.9, 35.6, 37.8, 39.7, 51.6, 126.3, 127.3, 129.0, 166.7, 173.3, 173.9, 174.2.

Anal. Calc'd. for $C_{17}H_{22}N_4O_4$ plus 1.2 $CF_3CO_2H$ and 1 $H_2O$: C, 46.49; H, 5.07; N, 11.18. Found: C, 46.61; H, 4.70; N, 11.16.

EXAMPLE 34C

3-[[[1-[4-(aminoiminomethyl)phenyl]-2-oxo-3-piperidinyl]acetyl]amino]-3-(3-thienyl)propanoic acid, enantiomerically enriched isomer B

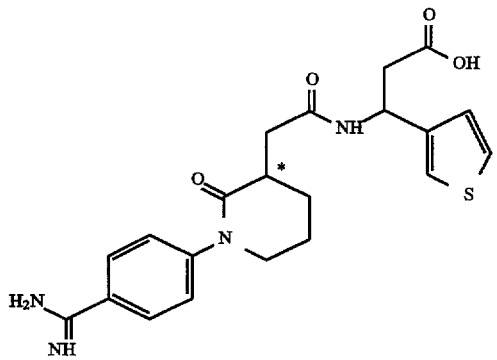

The title compound was prepared in the manner of Example 1 substituting ethyl 3-amino-3-(3-thienyl) propanoic for ethyl-3(S)-amino-4-pentenoate and 1-(4-cyanophenyl)-2-piperidone-3-acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of Example 1 by substituting 5-bromovaleryl chloride for 4-bromobutyryl chloride in step A of Example 1. The 1-(4-cyanophenyl)-2-piperidone-3-acetic acid was resolved in the same manner as the 1-(4-cyanophenyl)-2-pyrrolidinone-3-acetic acid in Example 5. The final product was purified by reverse phase HPLC using the conditions of Example 1 to afford the title compound. The product was verified by H NMR (CD$_3$OD) δ1.52–1.63 (m, 2 c$_2$), 2.04–2.46 (m, 2-CH$_2$), 3.14–3.38 (m, CH$_2$), 4.95–5.08 (m, CHN), 6.61–6.82 (m, 3H, ArH), 7.05–7.14 (m, 2H, ArH), 7.31–7.46 (m, 2H, ArH).

Anal. Calc'd for $C_{21}H_{24}N_4O_4S$ plus 1.3 $CF_3CO_2H$ and 1.5 $H_2O$: C, 46.95; H, 4.72; N, 9.28. Found: C, 47.00; H, 4.33; N, 9.49.

EXAMPLE 34D

Ethyl 3(S)-[[[1-[4-(aminoiminomethyl)phenyl]-2-oxo-3-piperidinyl]acetyl]amino]-3-(3-furanyl) propanoate, enantiomerically enriched isomer B

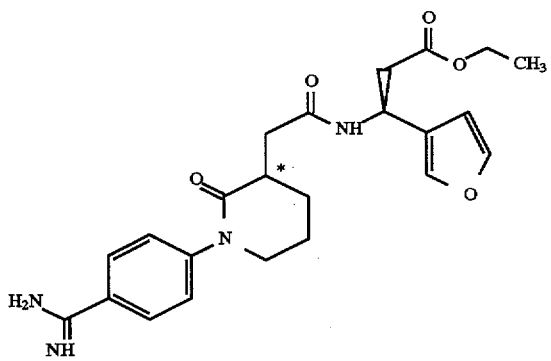

The title compound was prepared in the manner of Example 1 substituting ethyl 3(S)-amino-3-(3-furanyl)

propanoate for ethyl-3(S)-amino-4-pentenoate and 1-(4-cyanophenyl)-2-piperidone-3-acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of Example 1 by substituting 5-bromovaleryl chloride for 4-bromobutyryl chloride in step A of Example 1. The 1-(4-cyanophenyl)-2-piperidone-3-acetic acid was resolved in the same manner as the 1-(4-cyanophenyl)-2-pyrrolidinone-3-acetic acid in Example 5. The final product was purified by reverse phase HPLC using the conditions of Example 1 to afford the title compound ($[\alpha]_D^{25}$=−2.2°, c 0.045 MeOH). The product was verified by C NMR (CD$_3$OD) δ12.8, 21.7, 26.1, 37.0, 38.9, 39.4, 42.2, 60.2, 108.6, 125.6, 126.4, 128.2, 139.0, 143.0, 148.2, 166.7, 170.7, 171.6, 173.0.

Anal. Calcd for C$_{23}$N$_{28}$N$_4$O$_5$ plus 1.2 CF$_3$CO$_2$H and 1.1 H$_2$O: C, 51.09; H, 5.30; N, 9.38. Found: C, 50.73; H, 4.89; N, 9.12.

EXAMPLE 34E

3(S)-[[[1-[4-aminoiminomethyl)phenyl]-2-oxo-3-piperidinyl]acetyl]amino]-3-(3-furanyl)propanoic acid, enantiomerically enriched isomer B

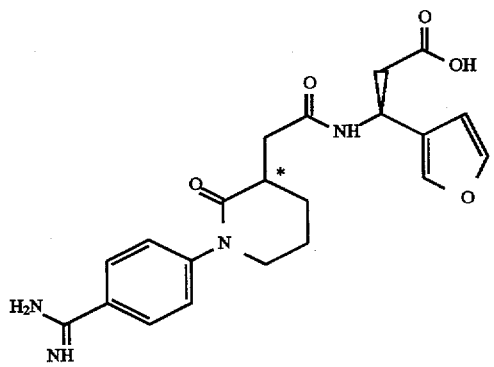

The title compound was prepared by treating the final product of the previous example with porcine liver esterase in the manner of Example 5. The product was purified by reverse phase HPLC using the conditions of Example 1 to afford the title compound ($[\alpha]_D^{25}$=+5.1°, c 0.039, MeOH). The product was verified by C NMR (CD$_3$OD) δ22.7, 26.9, 37.8, 39.7, 39.9, 43.0, 51.6, 109.4, 126.6, 127.2, 127.3, 129.0, 139.8, 143.7, 149.1, 166.7, 172.3, 173.2, 173.9.

Anal. Calcd for C$_{21}$H$_{24}$N$_4$O$_5$ plus 1.2 CF$_3$CO$_2$H and 0.1 HI: C, 50.00; H, 4.54; N, 9.97. Found: C, 50.26; H, 4.08; N, 9.99.

EXAMPLE 34F

Ethyl 3-[[[1-[4-(aminoiminomethyl)phenyl]-2-oxo-3-piperidinyl]acetyl]amino]-3-(2-furanyl)propanoate, diastereomers

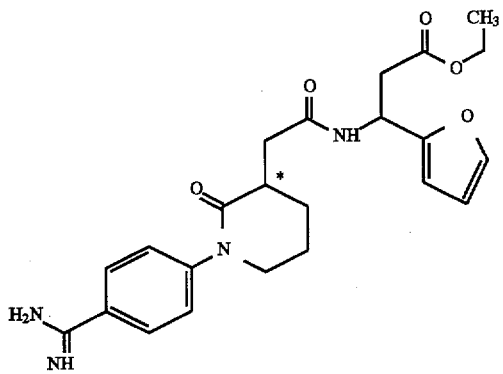

The title compound was prepared in the manner of Example 1 substituting ethyl 3-amino-3-(2-furanyl)propanoate for ethyl 3(S)-amino-4-pentenoate and 1-(4-cyanophenyl)-2-piperidone-3-acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of Example 1 by substituting 5-bromovaleryl chloride for 4-bromobutyryl chloride in step A of Example 1. The 1-(4-cyanophenyl)-2-piperidone-3-acetic acid was resolved in the same manner as the 1-(4-cyanophenyl)-2-pyrrolidinone-3-acetic acid in Example 5. The final product was purified by reverse phase HPLC using the conditions of Example 1 to afford the title compound. The product was verified by C NMR (CD$_3$OD) δ12.7, 21.6, 25.8, 36.8, 37.5, 38.7, 50.6, 60.1, 105.5, 109.5, 126.1, 126.3, 128.0, 141.5, 148.0, 166.7, 170.1, 171.5, 172.8.

Anal. Calcd for C$_{23}$H$_{28}$N$_4$O$_5$ plus 1.0 CF$_3$CO$_2$H and 0.5 H$_2$O: C, 53.28; H, 5.37; N, 9.94. Found: C, 52.94; H, 4.98; N, 9.85.

EXAMPLE 34G

3-[[[1-[4-(aminoiminomethyl)phenyl]2-oxo-3-piperidinyl]acetyl]amino]-3-(2-furanyl]propanoic acid, diastereomers

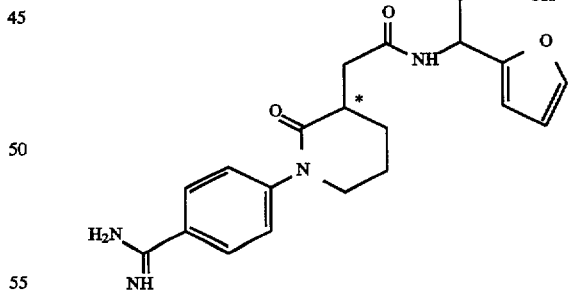

The title compound was prepared by treating the final product of the previous example with porcine liver esterase in the manner of Example 2. The product was purified by reverse phase HPLC using the conditions of Example 1 to afford the title compound. The product was verified by C NMR (CD$_3$OD) δ22.7, 26.9, 37.9, 38.3, 39.8, 44.8, 47.8, 51.8, 106.6, 110.6, 127.4, 127.5, 129.1, 142.6, 149.2, 166.7, 172.6, 173.1, 174.0.

Anal. Calcd for C$_{21}$H$_{24}$N$_4$O$_5$ plus 1.1 CF$_3$CO$_2$H and 1.0 H$_2$O: C, 50.13; H, 4.91; N, 10.08. Found: C, 49.77; H, 4.60; N, 9.99.

EXAMPLE 34H

Ethyl 3-[[[1-[4-(aminoiminomethyl)phenyl]-2-oxo-
3-piperidinyl]acetyl]amino]-3-(4-methoxyphenyl)
propanoate

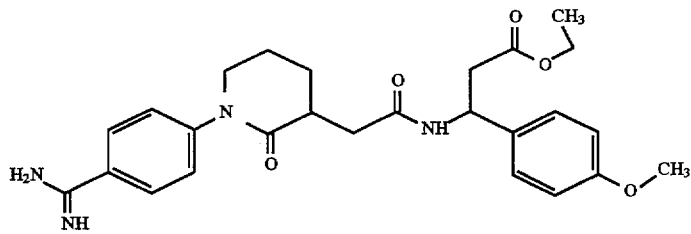

The title compound was prepared in the manner of
Example 1 substituting ethyl 3-amino-3-(4-methoxyphenyl)
-propanoate for ethyl (S)-3-amino-4-pentenoate. The product was purified by reverse phase HPLC using the conditions
of Example 1 to afford the title compound. The product was
verified by C NMR (CD$_3$OD) δ13.6, 22.6, 26.9, 37.8, 39.6,
41.1, 50.2, 51.6, 60.9, 114.1, 126.8, 127.3, 128.0, 129.0,
149.0, 159.4, 166.7, 171.5, 172.2, 173.8.

Anal. Calcd for C$_{26}$H$_{32}$N$_4$O$_5$ plus 1.8 CF$_3$CO$_2$H and 0.5
H$_2$O: C, 51.17; H, 5.05; N, 8.06. Found: C, 51.29; H, 4.68;
N, 8.46.

EXAMPLE 34I

3-[[[1-[4-(aminoiminomethyl)phenyl]-2-oxo-3-
piperidinyl]acetyl]amino]-3-(4-methoxyphenyl)
propanoic acid

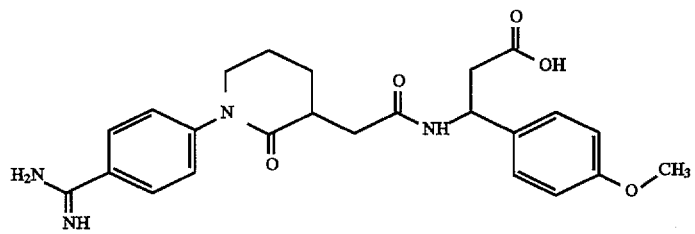

The title compound was prepared by treating the final
product of the previous example with porcine liver esterase
in the manner of Example 2. The product was purified by
reverse phase HPLC using the conditions of Example 1 to
afford the title compound. The product was verified by C
NMR (CD$_3$OD) δ1.57–2.07 (m, 2 CH$_2$), 2.54–2.92 (m,
2-CH$_2$), 3.62–3.83 (m, CH$_2$), 5.28–5.38 (m, CHN),
6.83–6.91 (m, 2H, ArH), 1 (m, 2H, ArH), 7.23–7.33 (m, 2H,
ArH), 7.46–7.58 (m, 2H, ArH), 7.78–7.84 (m, 2H, ArH).

Anal. Calcd for C$_{24}$H$_{28}$N$_4$O$_5$ plus 1.0 CF$_3$CO$_2$H and 1.5
H$_2$O: C, 52.61; H, 5.43; N, 9.44. Found: C, 52.69; H, 5.02;
N, 9.43.

EXAMPLE 34J

3(S)-[[[1-[4-(aminoiminomethyl)phenyl]-2-oxo-3-
piperidinyl]acetyl]amino]-4-pentenoic,
enantiomerically enriched isomer A

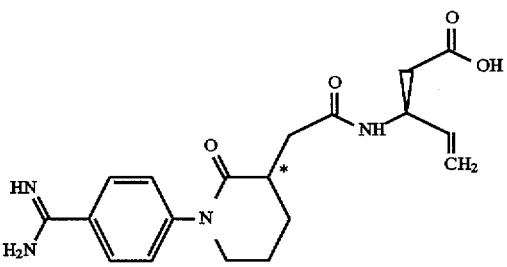

The title compound was prepared in the manner of
Example 1 substituting 1-(4-cyanophenyl)-2-piperidone-3-
acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of Example 1 by substituting 5-bromovaleryl chloride for 4-bromobutyryl chloride in step A of Example 1. The 1-(4-cyanophenyl)-2-piperidone-3-acetic acid was resolved in the same manner as the 1-(4-cyanophenyl)-2-pyrrolidinone-3-acetic acid in Example 5, except ethyl acetate was substituted for acetonitrile. The title compound was prepared by treating the final product of the above step with porcine liver esterase in the manner of Example 2. The final product was purified by reverse phase HPLC using the conditions of Example 1 to afford the title compound ($[\alpha]_D^{25}$=−109.8°, c 0.051 MeOH). The product was verified by C NMR (CD$_3$OD) δ21.9, 26.1, 37.1, 38.5, 38.9, 48.0, 50.9, 114.1, 126.6, 128.2, 136.8, 166.7, 172.1, 172.5, 173.2.

EXAMPLE 34K

Ethyl 3(S)-[[[-[4-(aminoiminomethyl)phenyl]-2-oxo-3-piperidinyl]amino]-4-pentenoate, enantiomerically enriched isomer B

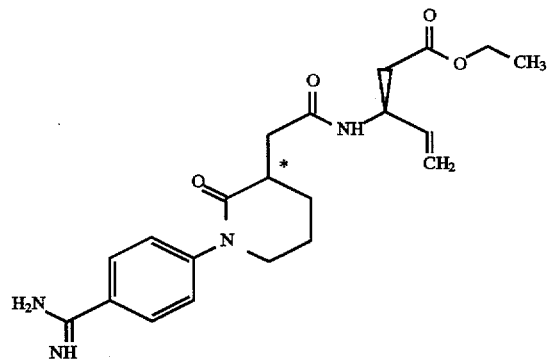

The title compound was prepared in the manner of Example 1 substituting 1-(4-cyanophenyl)-2-piperidone-3-acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of Example 1 by substituting 5-bromovaleryl chloride for 4-bromobutyryl chloride in step A of Example 1. The 1-(4-cyanophenyl)-2-piperidone-3-acetic acid was resolved in the same manner as the 1-(4-cyanophenyl)-2-pyrrolidinone-3-acetic acid in Example 5. The final product was purified by reverse phase HPLC using the conditions of Example 1 to afford the title compound. The product was verified by C NMR (CD$_3$OD) δ13.6, 22.5, 26.8, 37.8, 39.3, 39.6, 48.0, 51.5, 60.9, 114.9, 126.3, 127.2, 128.9, 137.2, 166.7, 172.5, 172.4, 173.8.

EXAMPLE 34L

3(S)-[[[1-[4-(aminoiminomethyl)phenyl]-2-oxo-3-piperidinyl]acetyl]amino]4-pentenoic, enantiomerically enriched isomer B

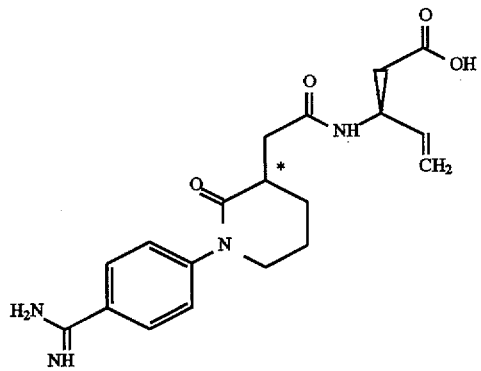

The title compound was prepared by treating the final product of the previous example with porcine liver esterase in the manner of Example 2. The product was purified by reverse phase HPLC using the conditions of Example 1 to afford the title compound. The product was verified by C NMR (CD$_3$OD) δ22.5, 26.8, 37.8, 39.1, 39.6, 51.6, 112.0, 114.9, 117.3, 127.2, 128.9, 129.9, 137.4, 149.0, 166.7, 172.4, 173.3, 173.8.

EXAMPLE 34M

Ethyl 3(S)-[[[1-[4-(aminoiminomethyl)phenyl]-2-oxo-3-piperidinyl]acetyl]amino]-4-pentynoate, enantiomerically enriched isomer B

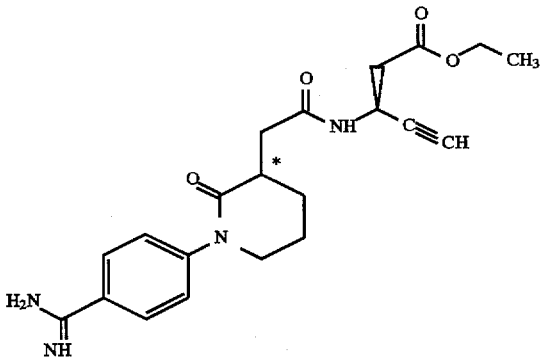

The title compound was prepared in the manner of Example 1 substituting ethyl 3(S)-amino-4-pentynoate for ethyl 3(S)-amino-4-pentenoate and 1-(4-cyanophenyl)-2-piperidone-3-acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of Example 1 by substituting 5-bromovaleryl chloride for 4-bromobutyryl chloride in step A of Example 1. The 1-(4-cyanophenyl)-2-piperidone-3-acetic acid was resolved in the same manner as the 1-(4-cyanophenyl)-2-pyrrolidinone-3-acetic acid in Example 5. The final product was purified by reverse phase HPLC using the conditions of Example 1 to afford the title compound.

The product was verified by C NMR (CD$_3$OD) δ13.3, 22.1, 26.4, 37.5, 37.9, 39.3, 51.4, 60.9, 71.6, 81.6, 114.7, 127.0, 128.8, 148.6, 166.7, 170.4, 172.1, 173.5.

EXAMPLE 34N

3(S)-[[[1-[4-(aminoiminomethyl)phenyl]-2-oxo-3-piperidinyl]acetyl]amino-4-pentynoic acid, enantiomerically enriched isomer B

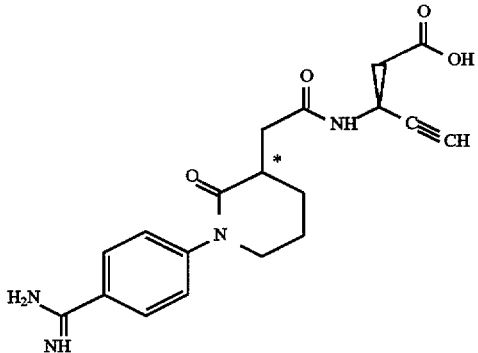

The title compound was prepared by treating the final product of the previous example with porcine liver esterase in the manner of Example 2. The product was purified by reverse phase HPLC using the conditions of Example 1 to afford the title compound. The product was verified by H NMR (CD$_3$OD) δ1.72–2.14 (m, 2 CH$_2$), 2.54–2.92 (m, 2 CH$_2$), 3.37 (d, J=1.5 Hz, CC-H), 3.54–3.83 (m, CH$_2$), 4.97–5.07 (m, CHN), 7.57 (d, 2H, J=8 Hz, ArH), 7.83 (d, 2H, J=8 Hz, ArH).

EXAMPLE 34P

Ethyl 3(S)-[[[1-[4-(aminoiminomethyl)phenyl]-2-oxo-3-piperidinyl]acetyl]amino]butyrate

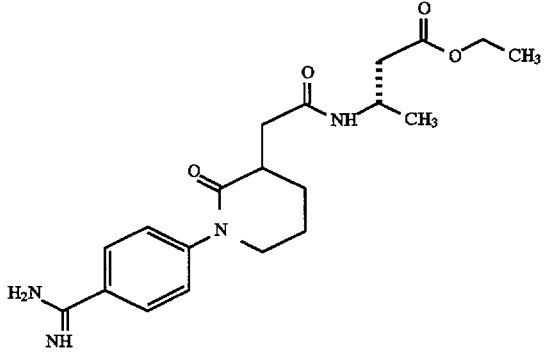

The title compound was prepared in the manner of Example 1 substituting ethyl-3(S)-amino-butyrate for ethyl-3(S)-amino-4-pentenoate. The product was purified by reverse phase HPLC using the conditions of Example 1 to afford the title compound. The product was verified by C NMR (CD$_3$OD) 13.7, 19.6, 22.6, 26.9, 27.6, 37.9, 39.6, 40.9, 43.0, 51.7, 60.8, 126.6, 127.3, 129.0, 149.1, 172.3, 172.4, 173.9.

EXAMPLE 34O

3S-[[[1-[4-(aminoiminomethyl)phenyl]-2-oxo-3-piperidinyl]acetyl]amino]butyric acid

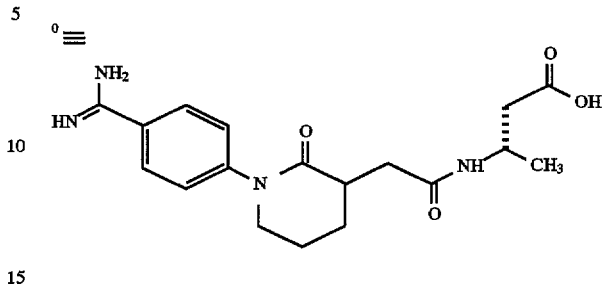

The title compound was prepared by treating the final product of the previous Example with porcine liver esterase in the manner of Example 2. The product was purified by reverse phase HPLC using the conditions of Example 1 to afford the title compound. The product was verified by C NMR (CD$_3$OD) 19.7, 22.8, 26.9, 37.8, 39.7, 40.74, 42.9, 51.7, 105.5, 126.5, 127.4, 129.1, 174.0.

EXAMPLE 34R

Ethyl 3S-[[[1-[4-(aminoiminomethyl)phenyl]-2-oxo-3-piperidinyl]acetyl]amino]-3-phenyl-propionate

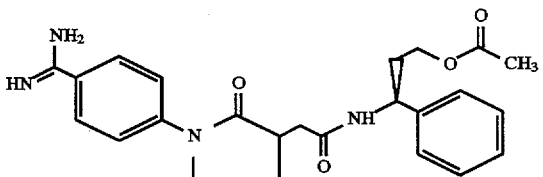

The title compound was prepared in the manner of Example 1 substituting ethyl-3(S)-amino-3-phenylpropionate for ethyl-3-(S)-amino-4-pentenoate. The product was purified by reverse phase HPLC using the conditions of Example 1 to afford the title compound. The product was verified by H NMR (CD$_3$OD) 1.2 (t, 3-CH$_3$), 1.8–2.05 (m, CH$_2$), 2.7 (m, CH$_2$) 2.8–2.9 (m, C$_H$), 3.6–3.9 (m, CH$_2$), 4.1 (q, 2-CH$_2$), 5.4 (t, NH), 7.2–7.85 (m, PhH).

EXAMPLE 34S

3S-[[[1-[4-(aminoiminomethyl)phenyl]-2-oxo-3-piperidinyl]acetyl]amino]-3-phenyl-propionic acid

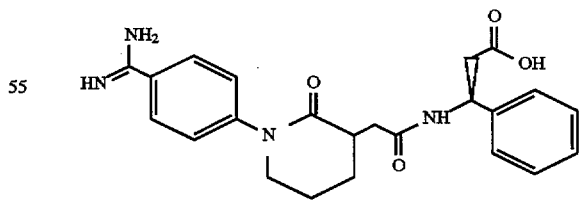

The title compound was prepared treating the final product of the previous Example with porcine liver esterase in the manner of Example 2. The product was purified by reverse phase HPLC using the conditions of Example 1 to afford the title compound. The product was verified by C NMR (CD$_3$OD) 22.0, 26.1, 37.0, 39.0, 40.2, 50.0, 50.9, 96.8, 125.9, 126.1, 126.6, 126.9, 128.1, 128.3, 141.4, 148.4, 171.6, 172.6, 173.2.

EXAMPLE 34T

Ethyl 3-[[[1-[4-(aminoiminomethyl]phenyl]-2-oxo-3-piperidinyl]acetyl]amino]-3-(3-thienyl)propanoate, enantiomerically enriched isomer B

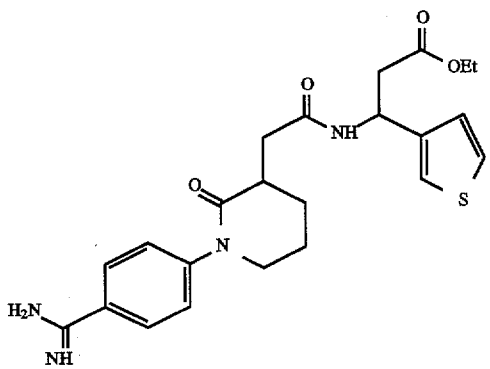

The title compound was prepared in the manner of Example 1 substituting ethyl 3-amino-3-(3-thienyl) propanoic for ethyl-3(S)-amino-4-pentenoate and 1-(4-cyanophenyl)-2-piperidone-3-acetic acid for 1-(4-cyanophenyl)-2-pyrrolidinone-3-acetic acid in step E of Example 1. The 1-(4-cyanophenyl)-2-piperidone-3-acetic acid was prepared in the same manner as the 1-(4-cyanophenyl)-2-pyrrolidinone-3-acetic acid of Example 1 by substituting 5-bromovaleryl chloride for 4-bromobutyryl chloride in step A of Example 1. The 1-(4-cyanophenyl)-2-piperidone-3-acetic acid was resolved in the same manner as the 1-(4-cyanophenyl)-2-pyrrolidinone-3-acetic acid in Example 5. The final product was purified by reverse phase HPLC using the conditions of Example 1 to afford the title compound. The product was verified by H NMR (diastereomers-$CD_3OD$) $\delta$1.20, 1.21 (2t, $CH_3$), 1.72–1.83 (m, 2-$CH_2$), 2.55–2.93 (m, 2-$CH_2$), 3.63–3.87 (m, $CH_2$), 4.06–4.15 (2q, $CH_2$), 5.46–5.53 (m, CHN), 7.07–7.83 (m, 7H, ArH).

EXAMPLE 35

Ethyl 3-[[[1-[4-(aminoiminomethyl)phenyl]-2-oxo-3-pyrrolidinyl]acetyl]amino]propionate, trifluoroacetate, enantiomerically enriched isomer B.

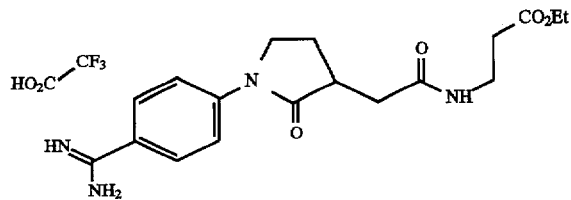

A. Preparation of Ethyl 3-[[[[1-(4-cyanophenyl)]-2-oxo-3-pyrrolidinyl]acetyl]amino]propionate, enantiomerically enriched isomer B.

The title compound was prepared from the product of example 5, step A (550 mg, 2.25 mmol) and β-alanine ethyl ester hydrochloride (380 mg, 2.47 mmol) in a manner similar to example 1, step E affording 690 mg (89%) of product. $^1$H-NMR ($CDCl_3$) $\delta$1.27 (t, J=7 Hz, 3H), 1.97 (m, 1H), 2.40–2.58 (m, 4H), 2.77 (dd, J=5 Hz, J=15 Hz, 1H), 3.08 (m, 1H), 3.53 (q, J=7 Hz, 2H), 3.83 (m, 2H), 4.15 (q, J=7 Hz, 2H), 7.66 (d, J=8 Hz, 2H), 7.80 (d, J=8 Hz, 2H).

B. Preparation of Ethyl 3-[[[1-(4-aminoiminomethyl) phenyl]-2-oxo-3-pyrrolidinyl]acetyl]amino]propionate, enantiomerically enriched isomer B.

The title compound was prepared from the product of Step A (680 mg, 1.98 mmol) in a manner similar to example 1, step F affording 630 mg (67%) of product as the TFA salt following reverse phase chromatography. $^1$H-NMR ($d_6$-DMSO) $\delta$1.19 (t, J=7 Hz, 3H), 1.81 (m, 1H), 2.29 (m, 2H), 2.46 (t, J=7 Hz, 2H), 2.58 (m, 1H) 2.98 (m, 1H), 3.28 (m, 2H), 3.83 (m, 2H), 4.07 (q, J=7 Hz, 2H), 7.87 (d, J=8 Hz, 2H), 7.93 (d, J=8 Hz, 2H).

Anal. Calc'd for $C_{22}H_{25}N_4O_6F_3$: C, 50.63; H, 5.31; N, 11.81. Found: C, 50.64; H, 5.31; N, 11.77.

EXAMPLE 36

3-[[[1-[4-(aminoiminomethyl)phenyl]-2-oxo-3-pyrrolidinyl]acetyl]amino]propionic acid, trifluoroacetate, enantiomerically enriched isomer B.

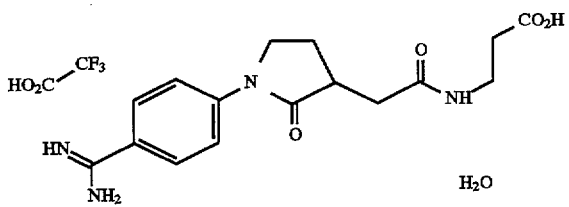

The title compound was prepared from the product of example 35, step B (150 mg, 0.316 mmol) in a manner similar to example 2 affording 78 mg (55%) of product as the TFA salt following reverse phase chromatography. $^1$H-NMR ($d_6$-DMSO) $\delta$1.81 (m, 1H), 2.28 (m, 2H), 2.39 (t, J=7 Hz, 2H), 2.58 (m, 1H), 2.96 (m, 1H), 3.25 (m, 2H), 3.83 (m, 2H), 7.85 (d, J=8 Hz, 2H), 7.92 (d, J=8 Hz, 2H).

Anal. Calc'd for $C_{18}H_{21}N_4O_6F_3 \cdot 1H_2O$: C, 46.55; H, 4.99; N, 12.06. Found: C, 46.42; H, 4.69; N, 12.23.

EXAMPLE 37

Ethyl 3-[[[[1-[4-(aminoiminomethyl)phenyl]-2-oxo-3-pyrrolidinyl]amino]carbonyl]amino]propionate, trifluoroacetate.

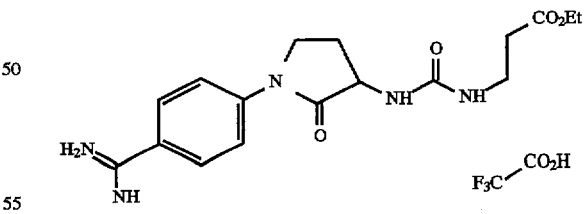

A. Preparation of Ethyl 3-[[[[1-[4-(cyanophenyl)-2-oxo-3-pyrrolidinyl]amino]carbonyl]amino]propionate.

The title compound was prepared from the product of example 17, step C (322 mg, 1.60 mmol) in a manner similar to example 17, step D substituting ethyl β-alanine hydrochloride for (3S)-vinyl-β-alanine hydrochloride affording 340 mg (62%) of product after trituration with $Et_2O$, $^1$H-NMR ($CDCl_3$) $\delta$1.27 (t, J=7 Hz, 3H), 2.06 (m, 1H), 2.54 (t, J=6 Hz, 2H), 2.82 (m, 1H), 3.49 (m, 2H), 3.76–3.88 (m, 2H), 4.14 (q, J=7 Hz, 2H), 4.48 (m, 1H), 7.67 (d, J=8 Hz, 2H), 7.81 (d, J=8 Hz, 2H).

Anal. Calc'd for $C_{17}H_{20}N_4O_4 \cdot 0.25\ H_2O$: C, 58.52; H, 5.92; N, 16.06. Found: C, 58.59; H, 6.08; N, 15.92.

B. Preparation of Ethyl 3-[[[[1-[4-(aminoiminomethyl)phenyl]-2-oxo-3-pyrrolidinyl]amino]carbonyl]amino]propionate, trifluoroacetate.

The title compound was prepared from the product of step A (210 mg, 0.52 mmol) in a manner similar to example 1, step F affording 187 mg (76%) of product as the TFA salt following reverse phase chromatography. $^1$H-NMR (d$_6$-DMSO) δ1.20 (t, J=7 Hz, 3H), 1.95 (m, 1H), 2.35–2.48 (m, 3H), 3.24 (m, 2H), 3.75–3.87 (m, 2H), 4.07 (q, J=7 Hz, 2H), 4.45 (m, 1H), 7.87 (d, J=8 Hz, 2H), 7.93 (d, J=8 Hz, 2H).

Anal. Calc'd for $C_{19}H_{24}N_5O_6F_3$: C, 48.00; H, 5.09; N, 14.73. Found: C, 47.81; H, 5.23; N, 14.59.

EXAMPLE 38

3-[[[[1-[4-(aminoiminomethyl)phenyl]-2-oxo-3-pyrrolidinyl]amino]carbonyl]amino]propionic acid, trifluoroacetate.

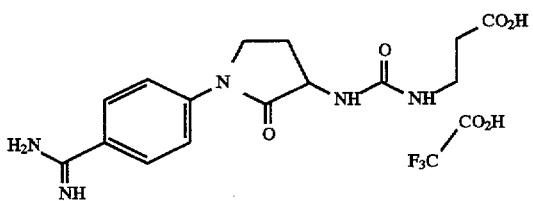

The title compound was prepared from the product of example 37, step B (100 mg, 0.21 mmol) in a manner similar to example 2 affording 33 mg (35%) of product as the TFA salt following reverse phase chromatography. $^1$H-NMR (d$_6$-DMSO) δ1.95 (m, 2H), 2.32–2.48 (m, 3H), 3.22 (m, 2H), 3.75–3.87 (m, 2H), 4.55 (m, 1H), 7.86 (d, J=8 Hz, 2H), 7.93 (d, J=8 Hz, 2H).

Anal. Calc'd for $C_{17}H_{20}N_5O_6F_3 \cdot 0.75\ H_2O$: C, 44.30; H, 4.70; N, 15.20. Found: C, 44.67; H, 4.54; N, 14.65.

EXAMPLE 39

Ethyl 3-[[[1-[4-(aminoiminomethyl)phenyl]-2-oxo-3-azetidinyl]acetyl]amino]-4-pentenoate

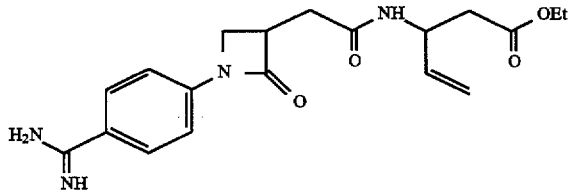

A. Preparation of N-(4-cyanophenyl)-3-bromopropanamide.

A solution of 4-aminobenzonitrile (12.5 g, 106 mmol) and dimethylaniline (14.3 g, 121 mmol) in 600 mL of $CH_2Cl_2$, is cooled in an ice bath under argon, and 3-bromopropionyl chloride (18.1 g, 106 mmol) is added dropwise over 20 min. The reaction mixture is allowed to warm to room temperature. After 2 hours, the mixture is diluted with $CH_2Cl_2$ and washed with 1N HCl, sat'd. NaCl, dried (MgSO$_4$) and concentrated. The title compound is verified by C NMR (CD$_3$OD) δ25.6, 38.9, 117.8, 118.9, 132.2, 141.7, 168.

B. 1-(4-cyanophenyl)-2-azetidinone.

To a stirring solution of NaH (0.264 g, 11.0 mmol)(60% w/w dispersion on mineral oil) in DMF/CH$_2$Cl$_2$ (20 mL/80 mL) is added the product of step A (2.52 g, 10.0 mmol) in DMF/CH$_2$Cl$_2$ (20 mL/80 mL) over a 3.5 hour period. The reaction is stirred at ambient temperature for 3.5 hours, and diluted with EtOAc (300 mL) and washed with 1N KHSO$_4$. The organic phase is further washed with saturated NaCl, dried (MgSO$_4$) and concentrated. C NMR (CDCl$_3$) δ35.9, 38.0, 116.1, 118.5, 133.0, 141.8, 168.5.

Ethyl 3-[[[1-[4-(aminoiminomethyl)phenyl]-2-oxo-3-azetidinyl]acetyl]amino]-4-pentenoate.

The title compound can be prepared following the procedures C–F of example 1 substituting the 1-(4-cyanophenyl)-2-azetidinone for 1-(4-cyanophenyl)-2-pyrrolidinone in step C. The final compound can be verified by H NMR.

EXAMPLE 40

Ethyl 3-[[[[1-[4-(aminoiminomethyl)phenyl]-2-oxo-3-pyrrolidinyl]amino]carbonyl]amino]propionate trifluoroacetate. Enantiomerically Enriched Isomer A.

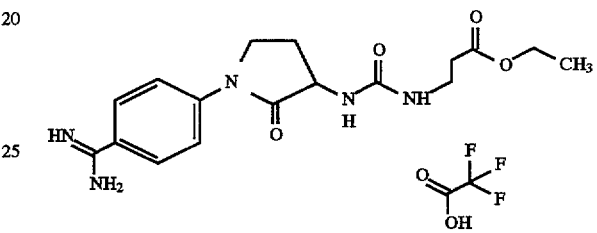

A. Preparation of 1-(4-cyanophenyl)-3-amino-pyrrolidin-2-one. Enantiomerically Enriched Isomer A.

To a suspension of the product of example 17, step C (4.75 g, 20 mmol) in saturated NaCl (20 mL) was added 1N NaOH (20 mL, 20 mmol). The mixture was extracted 3× with EtOAc, washed (saturated NaCl), dried (MgSO$_4$). To this filtrate (approximately 250 mL) was added a solution of (S)-(−)-mandelic acid in EtOAc (50 mL). The white precipitate was filtered, washed with EtOAc and dried. The product was recrystallized 7× from EtOH affording 940 mg of product [m.p 172°–173° C. $[\alpha]_D^{25}$=+38.6 (MeOH, c=9.58 mg/mL)]. This material was converted to the free base as described above affording 480 mg of product (m.p. 106°–107° C., $[\alpha]_D^{25}$=+19.5 (MeOH, c=10.25 mg/mL) 94% e.e.). Enantiomeric purity was determined by chiral HPLC analysis using a Crownpak CR(−) column (15 cm×4.0 mm) and isocratic elution with 1% aqueous HClO$_4$ at 1.2 mL/min. The detector was set at 254 nm.

B. Preparation of ethyl 3-[[[[1-(4-cyanophenyl)-2-oxo-3-pyrrolidinyl]amino]carbonyl]amino]propionate. Enantiomerically Enriched Isomer A.

To a suspension of 1,1'-carbonyldiimidazole (572 mg, 3.55 mmol) in pyridine (2.5 mL) at 5° C. under nitrogen was added solid ethyl 3-amino-propionate hydrochloride (545 mg, 3.55 mmol). The resulting solution was stirred at 5° C. for 15 minutes, diluted with 2.5 mL of DMF and removed from the ice bath. The product of step A (700 mg, 2.96 mmol) was added all at once and the reaction mixture was stirred at 75°–80° C. for 2 hours. After cooling to room temperature, the resulting solution was diluted with 15 mL of 1N HCl. The white precipitate was filtered, washed with H$_2$O and dried. Trituration and filtration from methyl t-butyl ether afforded 844 mg of product (m.p. 168.5°–169° C.). Extractive work up of the filtrate with EtOAc afforded an additional 110 mg of product (94% overall). $^1$H-NMR (CDCl$_3$) δ1.27 (t, J=7 Hz, 3H), 2.06 (m, 1H), 2.54 (t, J=6 Hz, 2H), 2.82 (m, 1H), 3.49 (m, 2H), 3.76–3.88 (m, 2H), 4.14 (q, J=7 Hz, 2H), 4.48 (m, 1H), 7.67 (d, J=8 Hz, 2H), 7.81 (d, J=8 Hz, 2H).

Anal. calc'd. for $C_{17}H_{20}N_4O_4$: C, 59.29; H, 5.85; N, 16.27. Found: C, 58.94; H, 5.71; N, 16.13.

C. Preparation of ethyl 3-[[[[1-[4-(aminoiminomethyl)phenyl]-2-oxo-3-pyrrolidinyl]amino]carbonyl]amino]propionate trifluoroacetate. Enantiomerically Enriched Isomer A The title compound was prepared from the product of step B (600 mg, 1.74 mmol) in a manner similar to Example 1, step F affording 600 mg (73%) of product as the TFA salt following reverse phase chromatography [m.p. 229–229.5 (dec.)]. $^1$H-NMR ($d_6$-DMSO) δ1.20 (t, J=7 HZ, 3H), 1.95 (m, 1H), 2.35–2.48 (m, 3H), 3.24 (m, 2H), 3.75–3.87 (m, 2H), 4.07 (q, J=7 Hz, 2H), 4.45 (m, 1H), 7.87 (d, J=8 Hz, 2H), 7.93 (d, J=8 Hz, 2H).

Anal. calc'd. for $C_{19}N_{24}N_5O_6F_3$: C, 48.00; H, 5.09; N, 14.73. Found: C, 47.86; H, 4.71; N, 14.56.

EXAMPLE 41

3-[[[[1-[4-(aminoiminomethyl)phenyl]-2-oxo-3-pyrrolidinyl]amino]carbonyl]amino]propanoic acid trifluoroacetate. Enantiomerically Enriched Isomer A.

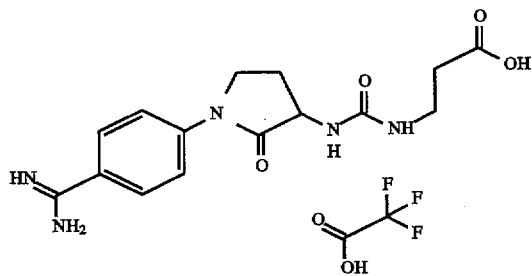

The title compound was prepared from the product of example 40, step C (0.50 g, 1.25 mmol) in a manner similar to Example 2 affording 400 mg (71%) of product as the TFA salt following reverse phase chromatography [m.p. 222°–223° C. (dec.)]. $^1$H-NMR ($d_6$-DMSO) δ1.95 (m, 2H), 2.32–2.48 (m, 3H), 3.22 (m, 2H), 3.75–3.87 (m, 2H), 4.55 (m, 1H), 7.86 (d, J=8 Hz, 2H), 7.93 (d, J=8 Hz, 2H).

Anal. calc'd. for $C_{17}H_{20}N_5O_6F_3 \cdot 1/4\ H_2O$: C, 45.18; H, 4.57; N, 15.50. Found: C, 45.05; H, 4.22; N, 15.29.

EXAMPLE 42

Ethyl 3-[[[[1-[4(aminoiminomethyl)phenyl]-2-oxo-3-pyrrolidinyl]amino]carbonyl]amino]propionate trifluoroacetate. Enantiomerically Enriched Isomer B

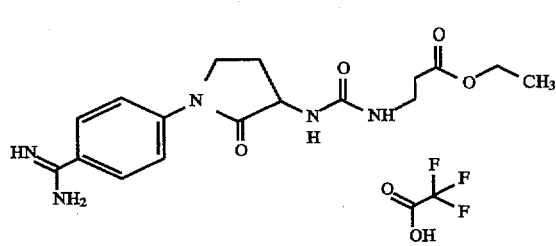

A. Preparation of 1-(4-cyanophenyl)-3-amino-pyrrolidin-2-one. Enantiomerically Enriched Isomer B The title compound was prepared from the product of example 17, step C (1.42 g, 7.08 mmol) in a manner similar to example 40, step A, substituting (S)-(−)-mandelic acid with (R)-(+)-mandelic acid. The product was recrystallized 3× from MeOH affording 800 mg of product [m.p. 172°–175° C., $[\alpha]_D^{25}$=−63.7 (MeOH, c=9.26 mg/mL)]. This material was suspended in $H_2O$ (5 mL) and neutralized with 1 equivalent of 1N NaOH (2.23 mL). The precipitated free base was filtered, washed with water and dried, affording 410 mg of product (m.p. 104.5°–105.5° C., $[\alpha]_D^{25}$=−18.9 (MeOH, c=10.59 mg/mL), >99% e.e.). Enantiomeric purity was determined by chiral HPLC analysis using a Crownpak CR(−) column (15 cm×4.0 mm) and isocratic elution with 1% aq. $HClO_4$ at 1.2 mL/min. The detector was set at 254 nm.

B. Preparation of ethyl 3-[[[[1-(4-cyanophenyl)-2-oxo-3-pyrrolidinyl]amino]carbonyl]amino]propionate. Enantiomerically Enriched Isomer B The title compound was prepared from the product of step A (400 mg, 1.99 mmol) in a manner similar to Example 40, step B affording 560 mg (82%) of product [m.p. 170.5°–171° C., $[\alpha]_D^{25}$=+16.9 ($CHCl_3$, c=14.46 mg/mL)]. $^1$H-NMR ($CDCl_3$) δ1.27 (t, J=7 Hz, 3H), 2.06 (m, 1H), 2.54 (t, J=6 Hz, 2H), 2.82 (m, 1H), 3.49 (m, 2H), 3.76–3.88 (m, 2H), 4.14 (q, J=7 Hz, 2H), 4.48 (m, 1H), 7.67 (d, J=8 Hz, 2H), 7.81 (d, J=8 Hz, 2H).

Anal. calc'd. for $C_{17}H_{20}N_4O_4$: C, 59.29; H, 5.85; N, 16.27. Found: C, 59.09; H, 5.79; N, 16.20.

C. Preparation of ethyl 3-[[[[1-[4-(aminoiminomethyl)phenyl]-2-oxo-3-pyrrolidinyl]amino]carbonyl]amino]propionate trifluoroacetate. Enantiomerically Enriched Isomer B.

The title compound was prepared from the product of step B (560 mg, 1.63 mmol) in a manner similar to Example 1, step F affording 590 mg (76%) of product as the TFA salt following reverse phase chromatography [m.p. 223°–224° C. (dec.)]. $^1$H-NMR ($d_6$-DMSO) δ1.20 (t, J=7 Hz, 3H), 1.95 (m, 1H), 2.35–2.48 (m, 3H), 3.24 (m, 2H), 3.75–3.87 (m, 2H), 4.07 (q, J=7 Hz, 2H), 4.45 (m, 1H), 7.87 (d, J=8 Hz, 2H), 7.93 (d, J=8 Hz, 2H).

Anal. calc'd. for $C_{19}H_{24}N_5O_6F_3$: C, 48.00; H, 5.09; N, 14.73. Found: C, 47.64; H, 4.72; N, 14.55.

EXAMPLE 43

3-[[[[1-[4-(aminoiminomethyl)phenyl]-2-oxo-3-pyrrolidinyl]amino]carbonyl]amino]propanoic acid trifluoroacetate. Enantiomerically Enriched Isomer B.

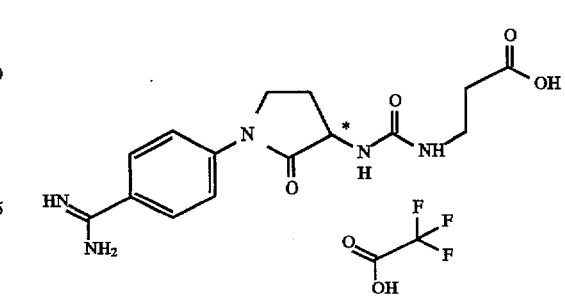

The title compound was prepared from the product of example 42, step C (0.10 g, 0.21 mmol) in a manner similar to Example 2 affording 55 mg (56%) of product as the TFA salt following reverse phase chromatography [m.p. 222°–223° C. (dec.)]. $^1$H-NMR ($d_6$-DMSO) δ1.95 (m, 2H), 2.32–2.48 (m, 3H), 3.22 (m, 2H), 3.75–3.87 (m, 2H), 4.55 (m, 1H), 7.86 (d, J=8 Hz, 2H), 7.93 (d, J=8 Hz, 2H).

Anal. calc'd. for $C_{17}H_{20}N_5O_6F_3$: C, 45.64; H, 4.51; N, 15.66. Found: C, 45.51; H, 4.36; N, 15.78.

EXAMPLE 44

Ethyl 3(R)-[[[[1-[4-(aminoiminomethyl)phenyl]-2-oxo-3-pyrrolidinyl]amino]carbonyl]amino]butanoate trifluoroacetate. Enantiomerically Enriched Isomer B

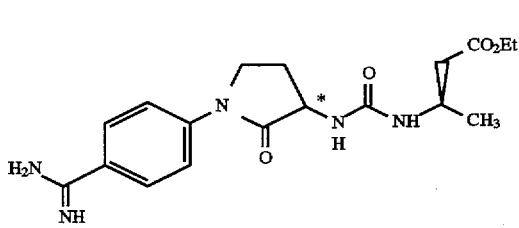

A. Preparation of Ethyl 3(R)-aminobutanoate (R)-mandelate

A solution of ethyl 3-aminobutyrate hydrochloride (4.5 g, 26.8 mmol) in 27 mL of 1N NaOH was extracted 2× with EtOAc. The organic fraction was dried ($Na_2SO_4$) and concentrated under reduced pressure. Recrystallization of the residue 3× from EtOAc afforded 1.93 g (51%) of product as a single chiral diastereomer as determined by NMR spectroscopy (m.p. 125°–125° C.). $^1$H-NMR (300 MHz, $CDCl_3$) δ1.00 (d, J=7 Hz, 3H), 1.27 (t, J=7 Hz, 3H), 2.23–2.45 (m, 2H), 3.13 (m, 1H), 4.13 (q, J=7 Hz, 2H), 4.85 (s, 1H), 7.17–7.33 (m, 3H), 7.41 (d, J=8 Hz, 2H).

Anal. calc'd. for $C_{14}H_{21}NO_5$: C, 59.35; H, 7.47; N, 4.94. Found: C, 59.03, H, 7.51; N, 4.83.

B. Preparation of Ethyl 3(R)-[[[[1-(4-cyanophenyl)-2-oxo-3-pyrrolidinyl]amino]carbonyl]amino]butanoate. Enantiomerically Enriched Isomer B The title compound was prepared from the product of step A (375 mg, 1.32 mmol) and the product of example 42, step A (260 mg, 1.1 mmol) in a manner similar to example 40, step E affording 295 mg (73%) of product (m.p. 177.5°–179° C.). $^1$H-NMR (300 MHz, $CDCl_3$) δ1.20–1.30 (m, 6H), 2.05 (m, 1H), 2.53 (m, 2H), 2.83 (m, 1H), 3.83 (m, 2H), 4.15 (q, J=7 Hz, 2H), 4.19 (m, 1H), 4.48 (m, 1H), 7.68 (d, J=8 Hz, 2H), 7.82 (d, J=8 Hz, 2H).

Anal. calc'd. for $C_{18}H_{22}N_4O_4 \cdot 0.1 H_2O$: C, 60.02; H, 6.21; N, 15.56. Found: C, 60.29; H, 6.21; N, 15.06.

C. Preparation of Ethyl 3(R)-[[[[1-[4-(aminoiminomethyl)phenyl]-2-oxo-3-pyrrolidinyl]amino]carbonyl]amino]butanoate trifluoroacetate. Enantiomerically Enriched Isomer B The title compound was prepared from the product of step B (600 mg, 1.68 mmol) in a manner similar to example 1, step F affording 440 mg (55%) as the TFA salt following reverse phase chromatography [m.p. 220°–221° C. (dec.)]. $^1$H-NMR ($d_6$-DMSO) δ1.08 (d, J=7 Hz, 3H), 1.98 (t, J=7 Hz, 3H), 1.95 (m, 1H), 2.32 (dd, J=7 Hz, J=15 Hz, 1H), 2.45–2.50 (m, 2H), 3.75–3.87 (m, 2H), 3.95 (m, 1H), 4.06 (q, J=7 Hz, 2H), 4.41 (m, 1H), 7.87 (d, J=8 Hz, 2H), 7.93 (d, J=8 Hz, 2H).

Anal. calc'd. for $C_2H_{26}N_5O_6F_3$: C, 49.08; H, 5.35; N, 14.31. Found: C, 48.83; H, 5.54; N, 13.97.

EXAMPLE 45

3(R)-[[[[1-[4-(aminoiminomethyl)phenyl]-2-oxo-3-pyrrolidinyl]amino]carbonyl]amino]butanoic acid trifluoroacetate. Enantiomerically Enriched Isomer B

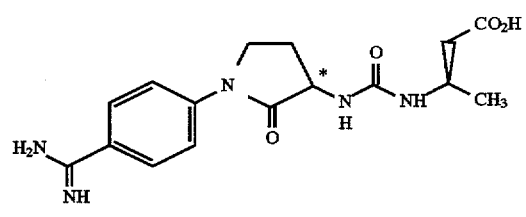

The title Compound was prepared from the product of example 44, step C (70 mg, 0.14 mmol) in a manner similar to example 2 affording 48 mg (73%) of product as the TFA salt following reverse phase chromatography [m.p. 179°–181° C. (dec.)]. $^1$H-NMR ($d_6$-DMSO) δ1.08 (d, J=7 Hz, 3H), 2.94 (m, 1H), 2.27 (dd, J=7 Hz, J=15 Hz, 1H), 2.35–2.50 (m, 2H), 3.75–3.87 (m, 2H), 3.93 (m, 1H), 4.43 (m, 1H), 7.86 (d, J=8 Hz, 2H), 7.93 (d, J=8 Hz, 2H).

Anal. calc'd. for $C_{18}H_{22}N_5O_6F_3 \cdot 1.5 H_2O$: C, 44.26; H, 5.16; N, 14.34. Found: C, 44.00; H, 4.69; N, 14.06.

EXAMPLE 46

Ethyl 3(S)-[[[[1-[4-(aminoiminomethyl) phenyl]-2-oxo-3-pyrrolidinyl]amino]carbonyl]amino] benzenepropanoate trifluoroacetate. Enantiomerically Enriched Isomer B

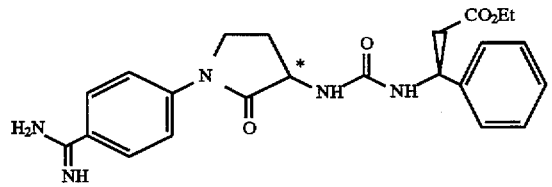

A. Preparation of Ethyl 3(S)-[[(1,1-dimethylethoxy)carbonyl]amino]benzenepropanoate To a stirred solution of N-Boc-D-phenylglycine (5.02 g, 20 mmol), N-methylmorpholine (2.02 g, 20 mmol) in EtOAc (100 mL) at 0° C. was added isobutyl chloroformate (2.73 g, 20 mmol). After 15 minutes the reaction mixture was filtered to remove the amine salts then an ethereal solution of diazomethane (60 mL, 30 mmol) was added. The cooling bath was removed and the reaction stirred at ambient temperature for 2 hours. The reaction was purged with nitrogen for 15 minutes to remove the excess diazomethane. The reaction was diluted with EtOAc, washed with 1N HCl, saturated $NaHCO_3$, and dried ($MgSO_4$). Evaporation of the solvent afforded the crude diazoketone which was dissolved in EtOH (100 mL) and then treated sequentially with $AgO_2CPh$ (1.6 g, 7 mmol) and triethylamine (6.06 g, 60 mmol). After 20 hours the reaction mixture was concentrated and chromatographed (silica gel, 15% EtOAc/hexanes) affording 4.90 g (85%) of product as a colorless oil. $^1$H-NMR (300 MHz, $CDCl_3$) δ1.17 (t, J=7 Hz, 3H), 1.43 (s, 9H), 2.73–2.92 (m, 2H), 4.07 (q, J=7 Hz, 2H), 5.10 (m, 1H), 5.48 (m, 1H), 7.22–7.39 (m, 5H).

B. Preparation of Ethyl 3(S)-aminobenzenepropanoate hydrochloride

Dry HCl gas was bubbled through a solution of the product of step A (3.0 g, 10.2 mmol) in EtOAc (50 mL) at ambient temperature for 15 minutes. After stirring for an additional 30 minutes, the solvent was removed under reduced pressure affording 2.30 g (98%) of product as a yellow oil. $^1$H-NMR (300 MHz, d$_6$-DMSO) δ1.03 (t, J=7 Hz, 3H), 3.02 (dd, J=10 Hz, J=15 Hz, 1H), 3.25 (dd, J=6 Hz, J=15 Hz, 1H), 3.96 (m, 2H), 4.55 (m, 1H), 7.3–7.6 (m, 5H), 8.93 (s, 3H).

C. Preparation of Ethyl 3(S)-[[[[1-(4-cyanophenyl)-2-oxo-3-pyrrolidinyl]-amino]carbonyl]amino]benzene-propanoate trifluoroacetate. Enantiomerically Enriched Isomer B The title compound was prepared from the product of step B (685 mg, 2.9 mmol) and the product of Example 42, step A (600 mg, 2.9 mmol) in a manner similar to Example 40, step B affording 564 mg (47%) of product (m.p. 108°–109° C.). $^1$H-NMR (300 MHz, CDCl$_3$) δ1.16 (t, J=7 Hz, 3H), 2.00 (m, 1H), 2.77–2.93 (m, 3H), 3.81 (m, 2H), 4.05 (q, J=7 Hz, 2H), 4.50 (m, 1H), 5.26 (m, 1H), 7.20–7.35 (m, 5H), 7.66 (d, J=8 Hz, 2H), 7.80 (d, J=8 Hz, 2H).

Anal. calc'd. for C$_{23}$H$_{24}$N$_4$O$_4$.1/3 H$_2$O: C, 64.79; H, 5.83; N, 13.14 Found: C, 64.65; H, 5.58; N, 13.18.

D. Preparation of Ethyl 3(S)-[[[[1-[4-(aminoiminomethyl)phenyl]-2-oxo-3-pyrrolidinyl]amino]carbonyl]amino]benzenepropanoate trifluoroacetate. Enantiomerically Enriched Isomer B The title compound was prepared from the product of step C (450 mg, 1.07 mmol) in a manner similar to Example 1, step F affording 430 mg (73%) of product as the TFA salt following reverse phase chromatography [m.p. 223°–224° C. (dec.)]. $^1$H-NMR (d$_6$-DMSO) δ1.14 (t, J=7 Hz, 3H), 2.03 (m, 1H), 2.47 (m, 1H), 2.80 (m, 2H), 3.84 (m, 2H), 4.04 (m, 2H), 4.50 (m, 1H), 5.05 (t, J=7 Hz, 1H), 7.23–7.44 (m, 5H), 7.92 (d, J=8 Hz, 2H), 7.97 (d, J=8 Hz, 2H).

EXAMPLE 47

3[S]-[[[[1-[4-(aminoiminomethyl)phenyl]-2-oxo-3-pyrrolidinyl]amino]carbonyl]amino] benzenepropanoic acid trifluoroacetate. Enantiomerically Enriched Isomer B

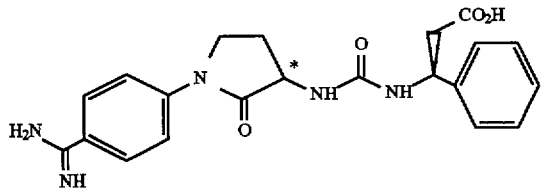

The title compound was prepared from the product of Example 46, step D (105 mg, 0.18 mmol) in a manner similar to Example 2 affording 46 mg (46%) of product as the TFA salt following reverse phase chromatography [m.p. 198°–199° C. (dec.)]. $^1$H-NMR (d$_6$-DMSO) δ1.94 (m, 1H), 2.40 (m, 1H), 2.68 (m, 2H), 3.80 (m, 2H), 4.44 (m, 1H), 5.05 (q, J=7 Hz, 1H), 7.20–7.44 (m, 5H), 7.92 (d, J=8 Hz, 2H), 7.97 (d, J=8 Hz, 2H).

Anal. calc'd. for C$_{21}$H$_{23}$N$_5$O$_4$F$_3$.2 H$_2$O: C, 49.37; H, 5.04; N, 12.52. Found: C, 49.07; H, 5.62; N, 12.43.

EXAMPLE 48

Ethyl 3-[[[[1-[4-(aminoiminomethyl)phenyl]-2-oxo-3-pyrrolidinyl]amino]carbonyl]amino]-2(S)-[[(phenylmethoxy) carbonyl]amino]propanoate trifluoroacetate. Enantiomerically Enriched Isomer B

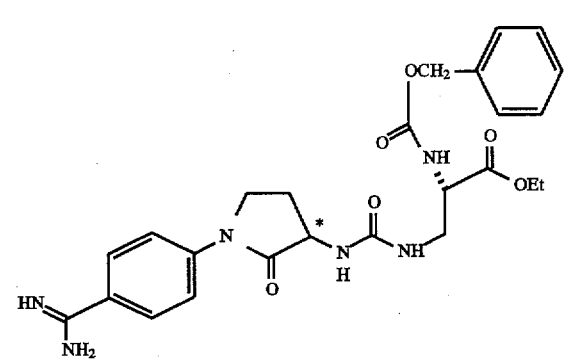

A. Preparation of Ethyl 3-amino-2(S)-[[(phenylmethoxy) carbonyl]amino]propanoate Hydrochloride To a stirred suspension of N$_α$-Z-L-2,3-diaminopropionic acid (0.50 g, 2.10 mmol) in EtOH (20 mL) was added thionyl chloride (310 μL, 4.2 mmol). The resulting solution was stirred at ambient temperature for 5 hours, the solvent was removed and the solid residue was triturated with Et$_2$O affording 573 mg (90%) of product (m.p. 134°–136° C.).

Anal. Calc'd. for C$_{13}$H$_{19}$N$_2$O$_4$Cl.1/4 H$_2$O: C, 50.82; H, 6.40; N, 9.12. Found: C, 50.87; H, 6.57; N, 8.95.

B. Preparation of Ethyl 3-[[[[1-(4-cyanophenyl)-2-oxo-3-pyrrolidinyl]amino]carbonyl]amino]-2(S)-[[(phenylmethoxy)carbonyl]amino]propanoate. Enantiomerically Enriched Isomer B The title compound was prepared from the product of step A (300 mg, 0.99 mmol) and the product of Example 42, step A (280 mg, 1.19 mmol) in a manner similar to Example 40, step E affording 341 mg (70%) of product (m.p. 177°–178° C.). $^1$H-NMR (300 MHz, DMSO) δ1.18 (t, J=7 Hz, 3H), 1.92 (m, 1H), 2.39 (m, 1H), 3.24 (m, 1H), 3.48 (m, 1H), 3.78 (m, 2H), 4.09 (m, 3H), 4.47 (m, 1H), 5.04 (s, 2H), 7.25–7.40 (m, 5H), 7.83–7.93 (m, 4H).

Anal. calc'd. for C$_{18}$H$_{27}$N$_5$O$_6$.1/4 H$_2$O: C, 60.29; H, 5.57; N, 14.06. Found: C, 60.34; H, 5.77; N, 14.04.

C. Preparation of Ethyl 3-[[[[1-[4-(aminoiminomethyl)phenyl]-2-oxo-3-pyrrolidinyl]amino]carbonyl]amino]-2(S)-[[(phenylmethoxy)-carbonyl]amino]propanoate trifluoroacetate. Enantiomerically Enriched Isomer B The title compound was prepared from the product of step B (625 mg, 1.25 mmol) in a manner similar to Example 1, step F affording 487 mg (62%) of product as the TFA salt following reverse phase chromatography [m.p. 197°–198° C., (dec.)]. $^1$H-NMR (300 MHz, DMSO) δ1.19 (t, J=7 Hz, 3H), 1.95 (m, 1H), 2.40 (m, 1H), 3.25 (m, 1H), 3.45 (m, 1H), 3.80 (m, 2H), 4.09 (m, 3H), 4.47 (m, 1H), 5.05 (s, 2H), 7.25–7.40 (m, 5H), 7.87 (d, J=8 Hz, 2H), 7.93 (d, J=8 Hz, 2H).

Anal. calc'd. for C$_{27}$N$_{31}$N$_6$O$_8$F$_3$.3/4 H$_2$O: C, 50.82; H, 5.13; N, 13.17. Found: C, 50.82; H, 5.03; N, 13.10.

EXAMPLE 49

3-[[[[1-[4-(aminoiminomethyl)phenyl]-2-oxo-3-pyrrolidinyl]amino]carbonyl]amino]-2(S)-[[(phenylmethoxy)carbonyl]amino]propanoic acid trifluoroacetate. Enantiomerically Enriched Isomer B

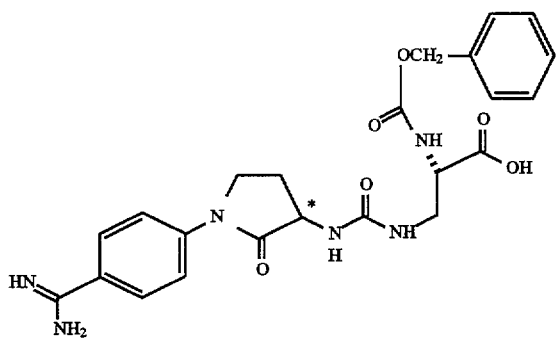

The title compound was prepared from the product of Example 48, step C (100 mg, 0.16 mmol) in a manner similar to Example 2 affording 52 mg (55%) of product as the TFA salt following reverse phase chromatography [m.p. 169°–170.5° C. (dec.)]. $^1$H-NMR (d$_6$-DMSO) δ1.94 (m, 1H), 2.42 (m, 1H), 3.21 (m, 1H), 3.49 (m, 1H), 3.82 (m, 2H), 4.03 (m, 1H), 4.48 (m, 1H), 5.04 (s, 2H), 7.28–7.40 (m, 5H), 7.87 (d, J=8 Hz, 2H), 7.93 (d, J=8 Hz, 2H).

Anal. calc'd. for $C_{25}H_{27}N_6O_8F_3 \cdot 1 \, H_2O$: C, 48.86; H, 4.76; N, 13.68. Found: C, 48.70; H, 4.54; N, 13.46.

EXAMPLE 50

Ethyl 3(S)-[[[-[4-(aminoiminomethyl)phenyl]-2-oxo-3-pyrrolidinyl]acetyl]amino]-3-(3-furanyl) propanonate Trifluoroacetate. Enantiomerically enriched isomer B

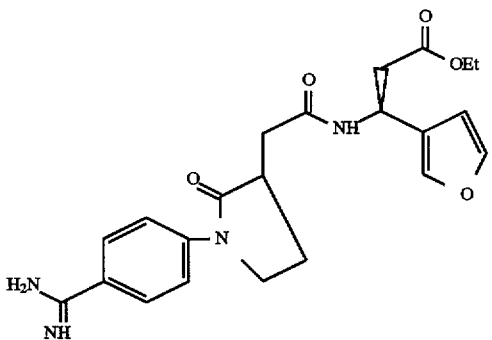

A. Preparation of Ethyl 3(S)-[[[1-(4-cyanophenyl)-2-oxo-3-pyrrolidinyl]acetyl]amino]-3-(3-furanyl) propanonate. Enantiomerically enriched isomer B.

The title compound was prepared from the product of Example 5 (550 mg, 2.25 mmol) and ethyl 3(S)-amino-3-(3-furanyl) propanoate trifluoroacetate (740 mg, 2.50 mmol) in a manner similar to Example 1, step E affording 900 mg (98%) of product used directly in the next reaction. $^1$H-NMR (300 MHz, CDCl$_3$) δ1.20 (t, J=7 Hz, 3H), 1.94 (m, 1H), 2.37–2.50 (m, 3H), 2.72–2.88 (m, 2H), 3.08 (m, 1H), 3.80 (m, 2H), 4.08 (q, J=7 Hz, 2H), 5.42 (m, 1H), 6.39 (m, 1H), 7.34 (m, 1H), 7.40 (m, 1H), 7.61 (d, J=8 Hz, 2H), 7.80 (d, J=8 Hz, 2H).

B. Preparation of Ethyl 3(S)-[[[1-[4-(aminoiminomethyl)phenyl]-2-oxo-3-pyrrolidinylacetyl]amino]-3-(3-furanyl) propanonate Trifluroacetate. Enantiomerically enriched isomer B The title compound was prepared from the product of step A (900 mg, 2.20 mmol) in a manner similar to Example 1, step F affording 200 mg (17%) of product as the TFA salt following reverse phase chromatography [m.p. 207°–208° C. (dec.)]. $^1$H-NMR (300 MHz, d$_6$-DMSO) δ1.16 (t, J=7 Hz, 3H), 1.83 (m, 1H), 2.20–2.40 (m, 2H), 2.60 (m, 1H), 2.74 (m, 2H), 2.98 (m, 1H), 3.83 (m, 2H), 4.05 (t, J=7 Hz, 2H), 5.22 (m, 1H), 6.46 (m, 1H), 7.55 (m, 1H), 7.60 (m, 1H), 7.87 (d, J=8 Hz, 2H), 7.92 (d, J=8 Hz, 2H).

Anal. calc'd. for $C_{24}H_{27}N_4O_7F_3 \cdot 3/4 \, H_2O$: C, 52.03; H, 5.18; N, 10.11. Found: C, 51.96; H, 4.96; N, 9.94.

EXAMPLE 51

3(S) -[[[1-[4-(aminoiminomethyl)phenyl]-2-oxo-3-pyrrolidinyl]acetyl]amino]-3-(3-furanyl)propanoic acid Trifluoroacetate. Enantiomerically enriched B

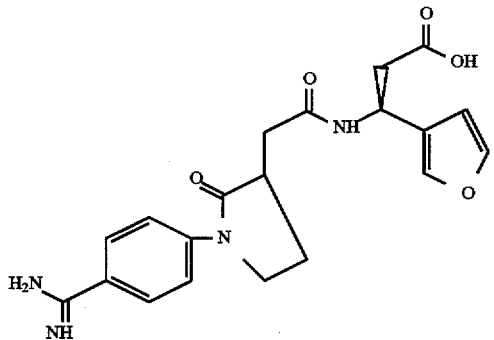

The title compound was prepared from the product of Example 50, step B (150 mg, 0.28 mmol) in a manner similar to Example 2 affording 62 mg (45%) of product as the TFA salt following reverse phase chromatography [m.p. 200–201 (dec.)]. $^1$H-HMR (300 MHz, d$_6$-DMSO) δ1.85 (m, 1H), 2.20–2.38 (m, 2H), 2.55–2.73 (m, 3H), 2.98 (m, 1H), 3.83 (m, 2H), 5.18 (m, 1H), 6.45 (m, 1H), 7.53 (m, 1H), 7.58 (m, 1H), 7.87 (d, J=8 Hz, 2H), 7.92 (d, J=8 Hz, 2H).

Anal. calc'd. for $C_{22}H_{23}N_4O_7F_3 \cdot 1H_2O$: C, 49.81; H, 4.75; N, 10.56. Found: C, 49.59; H, 4.53; N, 10.29.

The platelet-binding inhibitor activity of the compounds of the present invention can be demonstrated by the assays presented below.

Inhibition of Human Platelet Aggregation (PRP)

Platelet rich plasma was prepared from citrated whole blood (3.8% Na citrate, 1:10 in 30 ml blood) withdrawn from the antecubital vein (n=1). PRP was prepared by centrifugation (Sorvall RC3C, DuPont, Wilmington, Del.) of the whole blood at 1000×g for 3 min, allowing the centrifuge to stop without braking. Platelet poor plasma (PPP) was prepared by centrifugation of PRP at 2000×g for 10 min. Blood was obtained from donors who were selected to exhibit platelet counts in the range of 2.5 to $3.5 \times 10^8$/ml with aggregation responses of ~70–80 units. Aggregation was measured in a 4 channel aggregometer (model PAP-4C, Bio/Data Corp., Hatboro, Pa.). Aliquots of PPP were used to standardize the aggregometer for measurement of maximum light transmission. Platelet aggregation was measured as an increase in light transmission.

PRP (430 μl aliquot) was preincubated with 50 μl of various concentrations of compound (dissolved in 10% ETOH/water at a concentration of $10^{-3}$M. Compounds were diluted to desired concentration with 0.9% NaCl) for 2 min at 37° C., with stirring at 900 rpm, in the aggregometer. The stock collagen (Chronolog, Havertown, Pa., equine tendon) was diluted 1:10 with a 5% dextrose and water solution. The vehicle control response was obtained by adding 20 μl diluted collagen to the untreated aliquot of PRP+50 μl saline. Final collagen concentration was 4 μg/ml. Aggregation was recorded for 3 min following the addition of collagen. (Maximum aggregation was achieved in 2 min.). Percent inhibition was calculated by comparing treated and control collagen. Percent inhibition was calculated by comparing treated and control samples. $IC_{50}$'s were calculated graphically from dose-response curves. Average values and standard errors were calculated using the $IC_{50}$'s of the individual experiments. Statistical analyses were done by an unequal variance, unpaired Student's t-test [Minitab Reference Manual, Minitab Inc., State College, Pa. (1988)]. Statistical significance was assumed when p<0.05 was found.

In-Vitro Platelet Aggregation in PRP—(Dog)

Healthy male or female dogs were fasted for 8 hours prior to drawing blood; then 60 ml whole blood was collected using a butterfly needle and 30 cc plastic syringe with 6 ml of 0.129M buffered sodium citrate (3.8%) (drawn from a minimum of 3 dogs and blood was pooled). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The platelet count in the PRP was routinely $2-4\times10^8$ platelets per ml. 400 μl of the PRP preparation and 50 μl of the compound to be tested or saline were preincubated for 2 minutes at 37° C. in a BioData aggregometer (BioData, Horsham, Pa.). 50 μl of collagen (diluted 1:3 with 5% dextrose and water solution, 33 μg/ml final concentration, equine tendon, Chronolog, Havertown, Pa.) was added to the cuvettes and the aggregation was monitored for 3 minutes. All compounds are tested in duplicate.

Results are calculated as follows:

Percent of control=[(maximal OD minus initial OD of compound) divided by (maximal OD minus initial OD of control saline)]×100. The % inhibition=100-(percent of control).

The assay results for the compounds of the present invention and their median inhibitory concentrations ($IC_{50}$) are recorded in Table I. $IC_{50}$'s (if a compound showed 50% inhibition) were calculated graphically from the dose response curve. (NT in the following table indicates not tested.)

TABLE I

| Example | Dog PRP $IC_{50}$ (μM) | Human PRP $IC_{50}$ (μM) |
|---|---|---|
| 2 | 0.072 | NT |
| 4 | 0.052 | 0.055 |

TABLE I-continued

| Example | Dog PRP $IC_{50}$ (μM) | Human PRP $IC_{50}$ (μM) |
|---|---|---|
| 6 | 1.6 | 0.85 |
| 8 | 0.18 | 0.18 |
| 10 | 0.17 | 0.26 |
| 12 | 0.39 | 0.29 |
| 14 | 0.12 | NT |
| 16 | 0.10 | 0.31 |
| 18 | 0.17 | 0.10 |
| 19 | 0.15 | 0.09 |
| 22 | 0.18 | NT |
| 24 | 0.19 | NT |
| 26 | 0.59 | NT |
| 28 | 0.17 | 0.19 |
| 30 | 0.38 | 0.28 |
| 32 | 0.25 | 0.16 |
| 34 | 0.12 | NT |
| 34B | 0.24 | NT |
| 34C | 0.16 | NT |
| 34E | 0.070 | NT |
| 34G | 0.19 | NT |
| 34I | 0.18 | NT |
| 34J | 13% @ 1 μM | NT |
| 34L | 0.059 | NT |
| 34N | 0.059 | NT |
| 36 | 0.091 | 0.11 |
| 38 | 0.125 | NT |
| 41 | 30% @ 1 μM | 0.15 |
| 43 | 0.090 | NT |
| 45 | 0.039 | NT |
| 47 | 0.062 | NT |
| 49 | 0.054 | NT |
| 51 | 0.050 | NT |

What is claimed is:

1. A compound of the formula

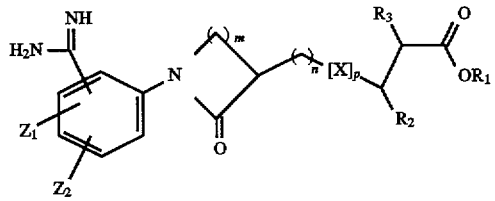

or a pharmaceutically acceptable salt thereof wherein $Z_1$ and $Z_2$ are independently selected from the group consisting of hydrogen, alkyl of 1 to 6 carbon atoms, hydroxy, halo and alkoxy of 1 to 6 carbon atoms;

$R_1$ is selected from the group consisting of hydrogen, lower alkyl of 1 to 6 carbon atoms, lower alkenyl of 2 to 6 carbon atoms, lower alkynyl of 2 to 6 carbon atoms, alkyloxycarbonyloxyalkyl, cycloalkyl of 3 to 6 carbon atoms and aryl optionally substituted by hydroxy, lower alkoxy of 1 to 6 carbon atoms, lower alkyl of 1 to 6 carbon atoms, halo, nitro, amino, acyloxy, phenyl or naphthyl;

$R_2$ is a substituent selected from the group consisting of hydrogen, lower alkyl of 1 to 6 carbon atoms, lower alkenyl of 2 to 6 carbon atoms, lower alkynyl of 2 to 6 carbon atoms, cycloalkyl and aryl, wherein said substituents are optionally substituted by one or more substituents selected from the group consisting of hydroxy, lower alkoxy of 1 to 6 carbon atoms, lower alkyl of 1 to 6 carbon atoms, halo, nitro, cyano, azido, ureido, ureylene, carboxyl, carbonyl derivatives, trifluoromethyl, acyloxy, alkylthio, arylthio, alkylsulfinyl, arylsulfinyl, alkylsulfonyl, arylsulfonyl, amino, alkylamino, trialkylsilyl, aminosulfonyl, dialkylamino, alkanoylamino, aroylamino, phenyl and naphthyl;

R₃ is selected from the group consisting of hydrogen, alkyl of 1 to 6 carbon atoms, alkoxy of 1 to 6 carbon atoms, halo, amino, monoalkylamino, dialkylamino, acylamino, alkylsulfonylamino, arylsulfonylamino, hydroxyl, alkoxycarbonyl and alkoxycarbonylalkyl;

X is selected from the group consisting of

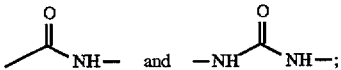

m is an integer from 2 to 3;
n is an integer from 0 to 4; and
p is 1.

2. A compound according to claim 1 wherein X is

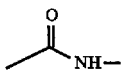

and p=1.

3. A compound according to claim 2 wherein m is 2.
4. A compound according to claim 3 wherein n is 1.
5. A compound according to claim 4 selected from the group consisting of
ethyl 3(S)-[[[1-[4-(aminoiminomethyl)phenyl]-2-oxo-3-pyrrolidinyl]acetyl]amino]-4-pentanoate;
3(S)-[[[1-[4-(aminoiminomethyl)phenyl]-2-oxo-3-pyrrolidinyl]acetyl]amino]-4-pentenoic acid, monohydrochloride;
ethyl 3(S)-[[[1-[4-(aminoiminomethyl)phenyl]-2-oxo-3-pyrrolidinyl]acetyl]amine]-4-pentenenoate, enantiomerically enriched isomer A;
ethyl 3(S)-[[[1-[4-(aminoiminomethyl)phenyl]-2-oxo-3-pyrrolidinyl]acetyl]amino]-4-pentenoic acid, monohydrochloride,
ethyl 3(S)-[[[1-[4-(aminoiminomethyl)phenyl]-2-oxo-3-pyrrolidinyl]acetyl]amino]-4-pentenoate,
3(S)-[[[1-[4-(aminoiminomethyl)phenyl]-2-oxo-3-pyrrolidinyl]acetyl]amino]-4-pentenoic acid,
ethyl 3-[[[1-[4-(aminoiminomethyl)phenyl]-2-oxo-3-pyrrolidinyl]acetyl]amino]propionate;
3-[[[1-[4-(aminoiminomethyl)phenyl]-2-oxo-3-pyrrolidinyl]acetyl]amino]propionic acid;
ethyl 3-[[[1-[4-(aminoiminomethyl)phenyl]-2-oxo-3-pyrrolidinyl]acetyl]amino]butanoate;
3-[[[1-[4-(aminoiminomethyl)phenyl]-2-oxo-3-pyrrolidinyl]acetyl]amino]butanoic acid;
ethyl 3-[[[1-[4-(aminoiminomethyl)phenyl]-2-oxo-3-pyrrolidinyl]acetyl]amino]-3-phenylpropionate;
3-[[[1-[4-(aminoiminomethyl)phenyl]-2-oxo-3-pyrrolidinyl]acetyl]amino]-3-phenylpropionic acid;
ethyl 3(S)-[[[1-[4-(aminoiminomethyl)phenyl]-2-oxo-3-pyrrolidinyl]acetyl]amino]-4-pentynoate;
3(S)-[[[1-[4-(aminoiminomethyl)phenyl]-2-oxo-3-pyrrolidinyl]acetyl]amino]-4-pentynoic acid;
3-[[[1-[4-(aminoiminomethyl)phenyl]-2-oxo-3-pyrrolidinyl]acetyl]amino]-N-[(phenylmethoxy)carbonyl]-L-alanine, ethyl ester;
3-[[[1-[4-(aminoiminomethyl)phenyl]-2-oxo-3-pyrrolidinyl]acetyl]amino]-N-[(phenylmethoxy)carbonyl]-L-alanine;
ethyl 3-[[[1-[4-(aminoiminomethyl)phenyl]-2-oxo-3-pyrrolidinyl]acetyl]amino]propanoate, trifluoroacetate;
3-[[[1-[4-(aminoiminomethyl)phenyl]-2-oxo-3-pyrrolidinyl]acetyl]amino]propanoic acid, trifluoroacetate;
Ethyl 3(S)-[[[1-[4-(aminoiminomethyl)phenyl]-2-oxo-3-pyrrolidinyl]acetyl]amino]-3-(3-furanyl)propanonate Trifluoroacetate;
and
3(S)-[[[1-[4-(aminoiminomethyl) phenyl]-2-oxo-3-pyrrolidinyl]acetyl]amino]-3-(3-furanyl) propanoic acid Trifluoroacetate.

6. A compound according to claim 2 wherein m is 3.
7. A compound according to claim 6 wherein n is 1.
8. A compound according to claim 7 selected from the group consisting of
ethyl 3(S)-[[[1-[4-(aminoiminomethyl) phenyl]-2-oxo-3-piperidinyl]acetyl]amino ]-5-(trimethylsilyl)-4-pentynoate;
3(S)-[[[1-[4-(aminoiminomethyl)phenyl]-2-oxo-3-piperidinyl]acetyl]amino]-5-(trimethylsilyl)-4-pentynoic acid;
ethyl 3-[[[1-[4-(aminoiminomethyl)phenyl]-2-oxo-3-piperidinyl]acetyl]amino]-4-pentynoate;
3-[[[1-[4-(aminoiminomethyl)phenyl]-2-oxo-3-piperidinyl]acetyl]amino]-4-pentynoic acid;
ethyl 3-[[[1-[4-(aminoiminomethyl)phenyl]-2-oxo-3-piperidinyl]acetyl]amino]-6,6-dimethyl-4-heptynoate;
3-[[[1-[4-(aminoiminomethyl)phenyl]-2-oxo-3-piperidinyl]acetyl]amino]-6,6 dimethyl-4-heptynoic acid;
ethyl 3-[[[1-[4-(aminoiminomethyl)phenyl]-2-oxo-3-piperidinyl]acetyl]amino]-5-phenyl-4-pentynoate;
3-[[[1-[4-(aminoiminomethyl)phenyl]-2-oxo-3-piperidinyl]acetyl]amino]-5-phenyl-4-pentynoic acid;
ethyl 3-[[[1-[4-(aminoiminomethyl)phenyl]-2-oxo-3-piperidinyl]acetyl]amino]-butanoate;
3-[[[1-[4-(aminoiminomethyl)phenyl]-2-oxo-3-piperidinyl]acetyl]amino]butanoic acid;
ethyl 3-[[[1-[4-(aminoiminomethyl)phenyl]-2-oxo-3-piperidinyl]acetyl]amino]-3-phenylpropanoate;
3-[[[1-[4-(aminoiminomethyl)phenyl]-2-oxo-3-piperidinyl]acetyl]amino]-3-phenylpropanoic acid;
ethyl 3(S) -[[[1-[4-(aminoiminomethyl) phenyl]-2-oxo-3-piperidinyl]acetyl]amino]-4-pentenoate;
3(S) -[[[1-[4-(aminoiminomethyl)phenyl]-2-oxo-3-piperidinyl]acetyl]amino]-4-pentenoic acid;
ethyl 3-[[[1-[4-(aminoiminomethyl)phenyl]-2-oxo-3-piperidinyl]acetyl]amino]propanoate;
3-[[[1-[4-(aminoiminomethyl)phenyl]-2-oxo-3-piperidinyl]acetyl]amino]propanoic acid;
ethyl 3-[[[1-[4-(aminoiminomethyl)phenyl]-2-oxo-3-piperidinyl]acetyl]amino]-3-(4-methoxyphenyl)propanoate;
3-[[[1-[4-(aminoiminomethyl]phenyl]-2-oxo-3-piperidinyl]acetyl]amino]-3-(4-methoxyphenyl)propanoic acid;
3(S)-[[[1-[4-(aminoiminomethyl)phenyl]-2-oxo-3-piperidinyl]acetyl]amino]-4-pentenoic;
ethyl 3(S)-[[[-[4-(aminoiminomethyl)phenyl]-2-oxo-3-piperidinyl]acetyl]amino]-4-pentenoate;
3(S)-[[[1-[4-(aminoiminomethyl)phenyl]-2-oxo-3-piperidinyl]acetyl]amino]4-pentenoic;
ethyl 3(S)-[[[1-[4-(aminoiminomethyl)phenyl]-2-oxo-Z-piperidinyl]acetyl]amino]-4-pentynoate;
3(S)-[[[1-[4-(aminoiminomethyl)phenyl]-2-oxo-3-piperidinyl]acetyl]amino-4-pentynoic acid;
ethyl 3(S)-[[[1-[4-(aminoiminomethyl)phenyl]-2-oxo-3-piperidinyl]acetyl]amino]butyrate;
3S-[[[1-[4-(aminoiminomethyl)phenyl]-2-oxo-3-piperidinyl]acetyl]amino]butyric acid;
ethyl 3S-[[[1-[4-(aminoiminomethyl)phenyl]-2-oxo-3-piperidinyl]acetyl]amino]-3-phenyl-propionate;
3S-[[[1-[4-(aminoiminomethyl)phenyl]-2-oxo-3-piperidinyl]acetyl]amino]-3-phenyl-propionic acid.

9. A compound according to claim 1 wherein X is

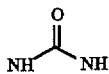

and p is 1.

10. A compound according to claim 9 wherein n is 0.

11. A compound according to claim 10 wherein m is 2.

12. A compound according to claim 11 selected from the group consisting of ethyl 3(S) -[[[[1-[4-(aminoiminomethyl)phenyl]-2-oxo-3-pyrrolidinyl]amino]carbonyl]amino]-4-pentenoate;

3S-[[[[1-[4-(aminoiminomethyl)phenyl]-2-oxo-3-pyrrolidinyl]amino]carbonyl]amino]-4-pentenoic acid;

ethyl 3-[[[[1-[4-(aminoiminomethyl)phenyl]-2-oxo-3-pyrrolidinyl]amino]carbonyl]amino]propanoate, trifluoroacetate;

3-[[[[1-[4-(aminoiminomethyl)phenyl]-2-oxo-3-pyrrolidinyl]amino]carbonyl]amino]propanoic acid, trifluoroacetate;

ethyl 3-[[[[1-[4-(aminoiminomethyl)phenyl]-2-oxo-3-pyrrolidinyl]amino]carbonyl]amino]propionate trifluoroacetate, Enantiomerically Enriched Isomer A;

3-[[[[1-[4-(aminoiminomethyl)phenyl]-2-oxo-3-pyrrolidinyl]amino]carbonyl]amino]propanoic acid trifluoroacetate;

ethyl 3-[[[[1-[4(aminoiminomethyl)phenyl]-2-oxo-3-pyrrolidinyl]amino]carbonyl]amino]propionate trifluoroacetate;

3-[[[[1-[4-(aminoiminomethyl)phenyl]-2-oxo-3-pyrrolidinyl]amino]carbonyl]amino]propanoic acid trifluoroacetate;

ethyl 3(R) -[[[[1-[4-(aminoiminomethyl)phenyl]-2-oxo-3-pyrrolidinyl]amino]carbonyl]amino]butanoate trifluoroacetate;

3(R)-[[[[1-[4-(aminoiminomethyl)phenyl]-2-oxo-3-pyrrolidinyl]amino]carbonyl]amino]butanoic acid trifluoroacetate;

ethyl 3(S)-[[[[1-[4-(aminoiminomethyl)phenyl]-2-oxo-3-pyrrolidinyl]amino]carbonyl]amino]benzenepropanoate trifluoroacetate;

3[S)-[[[[1-[4-(aminoiminomethyl)phenyl]-2-oxo-3-pyrrolidinyl]amino]carbonyl]amino]benzenepropanoic acid trifluoroacetate;

ethyl 3-[[[[1-[4-(aminoiminomethyl)phenyl]-2-oxo-3-pyrrolidinyl]amino]carbonyl]amino]-2(S)-[[(phenylmethoxy)carbonyl]amino]propanoate trifluoroacetate;

and

3-[[[[1-[4-(aminoiminomethyl)phenyl]-2-oxo-3-pyrrolidinyl]amino]carbonyl]amino]-2(S)-[[(phenylmethoxy)carbonyl]amino]propanoic acid trifluoroacetate.

13. A pharmaceutical composition comprising a therapeutically effective amount of compound of the formula according to claim 1.

14. A pharmaceutical composition according to claim 13 wherein the compound is selected from the group consisting of ethyl 3(S)-[[[1-[4-(aminoiminomethyl)phenyl]-2-oxo-3-pyrrolidinyl]acetyl ]amino ]-4-pentenoate;

3(S)-[[[1-[4-(aminoiminomethyl)phenyl]-2-oxo-3-pyrrolidinyl]acetyl]amino]-4-pentenoic acid, monohydrochloride;

ethyl 3(S)-[[[1-[4-(aminoiminomethyl)phenyl]-2-oxo-3-pyrrolidinyl]acetyl]amino]-4-pentenoate, 3(S)-[[[1-[4-(aminoiminomethyl)phenyl]-2-oxo-3-pyrrolidinyl]acetyl]amino]-4-pentenoic acid, monohydrochloride;

ethyl 3(S)-[[[1-[4-(aminoiminomethyl)phenyl]-2-oxo-3-pyrrolidinyl]acetyl]amino]-4-pentenoate;

3(S)-[[[1-[4-(aminoiminomethyl)phenyl]-2-oxo-3-pyrrolidinyl]acetyl]amino]-4-pentenoic acid;

ethyl 3-[[[1-[4-(aminoiminomethyl)phenyl]-2-oxo-3-pyrrolidinyl]acetyl]amino]propionate;

3-[[[1-[4-(aminoiminomethyl)phenyl]-2-oxo-3-pyrrolidinyl]acetyl]amino]propionic acid;

ethyl 3-[[[1-[4-(aminoiminomethyl)phenyl]-2-oxo-3-pyrrolidinyl]acetyl]amino]butanoate;

3-[[[1-[4-(aminoiminomethyl)phenyl]-2-oxo-3-pyrrolidinyl]acetyl]amino]butanoic acid;

ethyl 3-[[[1-[4-(aminoiminomethyl)phenyl]-2-oxo-3-pyrrolidinyl]acetyl]amino]-3-phenylpropionate;

3-[[[1-[4-(aminoiminomethyl)phenyl]-2-oxo-3-pyrrolidinyl]acetyl]amino]-3-phenylpropionic acid;

ethyl 3(S)-[[[1-[4-(aminoiminomethyl)phenyl]-2-oxo-3-pyrrolidinyl]acetyl]amino]-4-pentynoate;

3(S)-[[[1-[4-(aminoiminomethyl)phenyl]-2-oxo-3-pyrrolidinyl]acetyl]amino]-4-pentynoic acid;

3-[[[1-[4-(aminoiminomethyl)phenyl]-2-oxo-3-pyrrolidinyl]acetyl]amino]-N-[(phenylmethoxy)carbonyl]-L-alanine, ethyl ester;

3-[[[1-[4-(aminoiminomethyl)phenyl]-2-oxo-3-pyrrolidinyl]acetyl]amino]-N-[(phenylmethoxy)carbonyl]-L-alanine;

ethyl 3-[[[1-[4-(aminoiminomethyl)phenyl]-2-oxo-3-pyrrolidinyl]acetyl]amino]propanoate, trifluoroacetate;

3-[[[1-[4-(aminoiminomethyl)phenyl]-2-oxo-3-pyrrolidinyl]acetyl]amino]propanoic acid, trifluoroacetate;

ethyl 3(S)-[[[1-[4-(aminoiminomethyl)phenyl]-2-oxo-3-pyrrolidinyl]amino]carbonyl]amino]-4-pentenoate;

3(S)-[[[1-[4-(aminoiminomethyl)phenyl]-2-oxo-3-pyrrolidinyl]amino]carbonyl]amino]-4-pentenoic acid;

ethyl 3-[[[1-[4-(aminoiminomethyl)phenyl]-2-oxo-3-pyrrolidinyl]amino]carbonyl]amino]propanoate, trifluoroacetate;

3-[[[1-[4-(aminoiminomethyl)phenyl]-2-oxo-3-pyrrolidinyl]amino]carbonyl]amino]propanoic acid, trifluoroacetate;

ethyl 3(S)-[[[1-[4-(aminoiminomethyl)phenyl]-2-oxo-3-piperidinyl]acetyl]amino]-5-(trimethylsilyl)-4-pentynoate;

3(S)-[[[1-[4-(aminoiminomethyl)phenyl]-2-oxo-3-piperidinyl]acetyl]amino]-5-(trimethylsilyl)-4-pentynoic acid;

ethyl 3(S)-[[[1-[4-(aminoiminomethyl)phenyl]-2-oxo-3-piperidinyl]acetyl]amino]-4-pentynoate;

3-[[[1-[4-(aminoiminomethyl)phenyl]-2-oxo-3-piperidinyl]acetyl]amino]-4-pentynoic acid;

ethyl 3-[[[1-[4-(aminoiminomethyl) phenyl]-2-oxo-3-piperidinyl]acetyl]amino ]-6,6-dimethyl-4-heptynoate;

3-[[[1-[4-(aminoiminomethyl)phenyl]-2-oxo-3-piperidinyl]acetyl]amino]-6,6-dimethyl-4-heptynoic acid;

ethyl 3-[[[1-[4-(aminoiminomethyl)phenyl]-2-oxo-3-piperidinyl]acetyl]amino]-5-phenyl-4-pentynoate;

3-[[[1-[4-(aminoiminomethyl)phenyl]-2-oxo-3-piperidinyl]acetyl]amino]-5-phenyl-4-pentynoic acid;

ethyl 3-[[[1-[4-(aminoiminomethyl)phenyl]-2-oxo-3-piperidinyl]acetyl]amino]-butanoate;

-[[[1-[4-(aminoiminomethyl) phenyl]-2-oxo-3-piperidinyl]acetyl]amino]butanoic acid ethyl 3-[[[1-[4-(aminoiminomethyl)phenyl]-2-oxo-3-piperidinyl]acetyl]amino]-3-phenylpropanoate;

3-[[[1-[4-(aminoiminomethyl)phenyl]-2-oxo-3-piperidinyl]
  acetyl]amino]-3-phenylpropanoic acid;
ethyl 3(S)-[[[1-[4-(aminoiminomethyl)phenyl]-2-oxo-3-
  piperidinyl]acetyl]amino]-4-pentenoate;
3(S)-[[[1-[4-(aminoiminomethyl)phenyl]-2-oxo-3-
  piperidinyl]acetyl]amino]-4-pentenoic acid;
ethyl 3-[[[1-[4-(aminoiminomethyl)phenyl]-2-oxo-3-
  piperidinyl]acetyl]amino]propanoate;
ethyl 3-[[[1-[4-(aminoiminomethyl)phenyl]-2-oxo-3-
  piperidinyl]acetyl]amino]-3-(4-methoxyphenyl)
  propanoate:
3-[[[1-[4-(aminoiminomethyl]phenyl]-2-oxo-3-piperidinyl]
  acetyl]amino]-3-(4-methoxyphenyl)propanoic acid;
3(S)-[[[1-[4-(aminoiminomethyl)phenyl]-2-oxo-3-
  piperidinyl]acetyl]amino]-4-pentenoic;
ethyl 3(S)-[[[-[4-(aminoiminomethyl)phenyl]-2-oxo-3-
  piperidinyl]acetyl]amino]-4-pentenoate;
3(S)-[[[1-[4-(aminoiminomethyl)phenyl]-2-oxo-3-
  piperidinyl]acetyl]amino]4-pentenoic;
ethyl 3(S) -[[[1-[4-(aminoiminomethyl)phenyl]-2-oxo-3-
  piperidinyl]acetyl]amino]-4-pentynoate;
3(S)-[[[1-[4-(aminoiminomethyl)phenyl]-2-oxo-3-
  piperidinyl]acetyl]amino-4-pentynoic acid;
ethyl 3(S)-[[[1-[4-(aminoiminomethyl)phenyl]-2-oxo-3-
  piperidinyl]acetyl]amino]butyrate;
3S-[[[1-[4-(aminoiminomethyl)phenyl]-2-oxo-3-
  piperidinyl]acetyl]amino]butyric acid;
ethyl 3S-[[[1–4-(aminoiminomethyl)phenyl]-2-oxo-3-
  piperidinyl]acetyl]amino]-3-phenyl-propionate;
3S-[[[1-[4-(aminoiminomethyl)phenyl]-2-oxo-3-
  piperidinyl]acetyl]amino]-3-phenyl-propionic acid;
ethyl 3-[[[[1-[4-(aminoiminomethyl)phenyl]-2-oxo-3-
  pyrrolidinyl]amino]carbonyl]amino]propionate trifluoro-
  acetate;
3-[[[[1-[4-(aminoiminomethyl)phenyl]-2-oxo-3-
  pyrrolidinyl]amino]carbonyl]amino]propanoic acid trif-
  luoroacetate;
ethyl 3-[[[[1-[4(aminoiminomethyl)phenyl]-2-oxo-3-
  pyrrolidinyl]amino]carbonyl]amino]propionate
  trifluoroacetate, Enantiomerically Enriched Isomer B;
3-[[[[1-[4-(aminoiminomethyl)phenyl]-2-oxo-3-
  pyrrolidinyl]amino]carbonyl]amino]propanoic acid trif-
  luoroacetate;
ethyl 3(R)-[[[[1-[4-(aminoiminomethyl)phenyl]-2-oxo-3-
  pyrrolidinyl]amino]carbonyl]amino]butanoate trifluoro-
  acetate;
3(R)-[[[[1-[4-(aminoiminomethyl)phenyl]-2-oxo-3-
  pyrrolidinyl]amino]carbonyl]amino]butanoic acid trifluo-
  roacetate;
ethyl 3(S)-[[[[1-[4-(aminoiminomethyl)phenyl]-2-oxo-3-
  pyrrolidinyl]amino]carbonyl]amino]benzenepropanoate
  trifluoroacetate;
3[S]-[[[[1-[4-(aminoiminomethyl)phenyl]-2-oxo-3-
  pyrrolidinyl]amino]carbonyl]amino]benzenepropanoic
  acid trifluoroacetate;
ethyl 3-[[[[1-[4-(aminoiminomethyl)phenyl]-2-oxo-3-
  pyrrolidinyl]amino]carbonyl]amino](S)-[[
  (phenylmethoxy)carbonyl]amino]propanoate trifluoroac-
  etate;
and
3-[[[[1-[4-(aminoiminomethyl)phenyl]-2-oxo-3-
  pyrrolidinyl]amino]carbonyl]amino](S) -[[
  (phenylmethoxy)carbonyl]amino]propanoic acid trifluo-
  roacetate.

15. A method of treatment a mammal to inhibit platelet aggregation comprising administering a therapeutically effective amount of a compound of the formula according to claim 1.

16. A method according to claim 1 wherein the compound is selected from the group consisting of
ethyl 3(S)-[[[1-[4-(aminoiminomethyl)phenyl]-2-oxo-3-
  pyrrolidinyl]acetyl]amino]-4-pentenoate;
3(S)-[[[1-[4-(aminoiminomethyl)phenyl]-2-oxo-3-
  pyrrolidinyl]acetyl]amino]-4-pentenoic acid, monohydro-
  chloride;
ethyl 3(S)-[[[1-[4-(aminoiminomethyl)phenyl]-2-oxo-3-
  pyrrolidinyl]acetyl]amino]-4-pentenoate;
3(S)-[[[1-[4-(aminoiminomethyl)phenyl]-2-oxo-3-
  pyrrolidinyl]acetyl]amino]-4-pentenoic acid, monohydro-
  chloride;
ethyl 3(S)-[[[1-[4-(aminoiminomethyl)phenyl]-2-oxo-3-
  pyrrolidinyl]acetyl]amino]-4-pentenoate;
3(S)-[[[1-[4-(aminoiminomethyl)phenyl]-2-oxo-3-
  pyrrolidinyl]acetyl]amino]-4-pentenoic acid;
ethyl 3-[[[1-[4-(aminoiminomethyl)phenyl]-2-oxo-3-
  pyrrolidinyl]acetyl]amino]propionate;
3-[[[1-[4-(aminoiminomethyl)phenyl]-2-oxo-3-
  pyrrolidinyl]acetyl]amino]propionic acid;
ethyl 3-[[[1-[4-(aminoiminomethyl)phenyl]-2-oxo-3-
  pyrrolidinyl]acetyl]amino]butanoate;
3-[[[1-[4-(aminoiminomethyl)phenyl]-2-oxo-3-
  pyrrolidinyl]acetyl]amino]butanoic acid;
ethyl 3-[[[1-[4-(aminoiminomethyl)phenyl]-2-oxo-3-
  pyrrolidinyl]acetyl]amino]-3-phenylpropionate;
3-[[[1-[4-(aminoiminomethyl)phenyl]-2-oxo-3-
  pyrrolidinyl]acetyl]amino]-3-phenylpropionic acid;
ethyl 3(S)-[[[1-[4-(aminoiminomethyl)phenyl]-2-oxo-3-
  pyrrolidinyl]acetyl]amino]-4-pentynoate;
3(S)-[[[1-[4-(aminoiminomethyl)phenyl]-2-oxo-3-
  pyrrolidinyl]acetyl]amino]-4-pentynoic acid;
3-[[[1-[4-(aminoiminomethyl)phenyl]-2-oxo-3-
  pyrrolidinyl]acetyl]amino]-N-[(phenylmethoxy)
  carbonyl]-L-alanine, ethyl ester;
3-[[[1-[4-(aminoiminomethyl) phenyl]-2-oxo-3-
  pyrrolidinyl]acetyl]amino]-N-[(phenylmethoxy)
  carbonyl]-L-alanine;
ethyl 3-[[[1-[4-(aminoiminomethyl)phenyl]-2-oxo-3-
  pyrrolidinyl]acetyl]amino]propanoate, trifluoroacetate;
3-[[[1-[4-(aminoiminomethyl)phenyl]-2-oxo-3-
  pyrrolidinyl]acetyl]amino]propanoic acid, trifluoroac-
  etate;
3(S)-[[[[1-[4-(aminoiminomethyl)phenyl]-2-oxo-3-
  pyrrolidinyl]amino]carbonyl]amino]-4-pentenoic acid;
ethyl 3(S)-[[[[1-[4-(aminoiminomethyl)phenyl]-2-oxo-3-
  pyrrolidinyl]amino]carbonyl]amino]-4-pentenoate;
ethyl 3-[[[[1-[4-(aminoiminomethyl)phenyl]-2-oxo-3-
  pyrrolidinyl]amino]carbonyl]amino]propanoate, trifluo-
  roacetate;
3-[[[[1-[4-(aminoiminomethyl)phenyl]-2-oxo-3-
  pyrrolidinyl]amino]carbonyl]amino]propanoic acid, trif-
  luoroacetate;
ethyl 3(S)-[[[1-[4-(aminoiminomethyl)phenyl]-2-oxo-3-
  piperidinyl]acetyl]amino]-5-(trimethylsilyl)-4-
  pentynoate;
3(S)-[[[1-[4-(aminoiminomethyl)phenyl]-2-oxo-3-
  piperidinyl]acetyl]-amino]-5-(trimethylsilyl)-4-pentynoic
  acid;
ethyl 3(S)-[[[1-[4-(aminoiminomethyl)phenyl]-2-oxo-3-
  piperidinyl]acetyl]amino]-4-pentynoate;
3-[[[1-[4-(aminoiminomethyl)phenyl]-2-oxo-3-piperidinyl]
  acetyl]amino]-4-pentynoic acid;
ethyl 3-[[[1-[4-(aminoiminomethyl)phenyl]-2-oxo-3-
  piperidinyl]acetyl]amino]-6,6-dimethyl-4-heptynoate;
3-[[[1-[4-(aminoiminomethyl)phenyl]-2-oxo-3-piperidinyl]
  acetyl]amino]-6,6-dimethyl-4-heptynoic acid;

ethyl 3-[[[1-[4-(aminoiminomethyl)phenyl]-2-oxo-3-piperidinyl]acetyl]amino]-5-phenyl-4-pentynoate;
3-[[[1-[4-(aminoiminomethyl)phenyl]-2-oxo-3-piperidinyl]acetyl]amino]-5-phenyl-4-pentynoic acid;
ethyl 3-[[[1-[4-(aminoiminomethyl)phenyl]-2-oxo-3-piperidinyl]acetyl]amino]-butanoate;
3-[[[1-[4-(aminoiminomethyl)phenyl]-2-oxo-3-piperidinyl]acetyl]amino]butanoic acid;
ethyl 3-[[[1-[4-(aminoiminomethyl)phenyl]-2-oxo-3-piperidinyl]acetyl]amino]-3-phenylpropanoate;
3-[[[1-[4-(aminoiminomethyl)phenyl]-2-oxo-3-piperidinyl]acetyl]amino]-3-phenylpropanoic acid;
ethyl 3(S)-[[[1-[4-(aminoiminomethyl)phenyl]-2-oxo-3-piperidinyl]acetyl]amino]-4-pentenoate;
ethyl 3-[[[1-[4-(aminoiminomethyl)phenyl]-2-oxo-3-piperidinyl]acetyl]amino]propanoate;
3(S)-[[[1-[4-(aminoiminomethyl)phenyl]-2-oxo-3-piperidinyl]acetyl]amino]-4-pentenoic acid;
ethyl 3-[[[1-[4-(aminoiminomethyl)phenyl]-2-oxo-3-piperidinyl]acetyl]amino]-3-(4-methoxyphenyl)propanoate:
3-[[[1-[4-(aminoiminomethyl]phenyl]-2-oxo-3-piperidinyl]acetyl]amino]-3-(4-methoxyphenyl)propanoic acid;
3(S)-[[[1-[4-(aminoiminomethyl) phenyl]-2-oxo-3-piperidinyl]acetyl]amino]-4-pentenoic;
ethyl 3(S)-[[[-[4-(aminoiminomethyl)phenyl]-2-oxo-3-piperidinyl]acetyl]amino]-4-pentenoate;
3(S)-[[[1-[4-(aminoiminomethyl)phenyl]-2-oxo-3-piperidinyl]acetyl]amino]4-pentenoic;
ethyl 3(S)-[[[1-[4-(aminoiminomethyl)phenyl]-2-oxo-3-piperidinyl]acetyl]amino]-4-pentynoate;
3(S) -[[[1-[4-(aminoiminomethyl) phenyl]-2-oxo-3-piperidinyl]acetyl]amino-4-pentynoic acid;
ethyl 3(S) -[[[1-[4-(aminoiminomethyl)phenyl]-2-oxo-3-piperidinyl]acetyl]amino]butyrate;
3S-[[[1-[4-(aminoiminomethyl)phenyl]-2-oxo-3-piperidinyl]acetyl]amino]butyric acid;
ethyl 3S-[[[1-4-(aminoiminomethyl)phenyl]-2-oxo-3-piperidinyl]acetyl]amino]-3-phenyl-propionate;
3S-[[[1-[4-(aminoiminomethyl)phenyl]-2-oxo-3-piperidinyl]acetyl]amino]-3-phenyl-propionic acid;

ethyl 3-[[[[1-[4-(aminoiminomethyl)phenyl]-2-oxo-3-pyrrolidinyl]amino]carbonyl]amino]propionate trifluoroacetate;
3-[[[[1-[4-(aminoiminomethyl)phenyl]-2-oxo-3-pyrrolidinyl]amino]carbonyl]amino]propanoic acid trifluoroacetate;
ethyl 3-[[[[1-[4(aminoiminomethyl)phenyl]-2-oxo-3-pyrrolidinyl]amino]carbonyl]amino]propionate trifluoroacetate;
3-[[[[1-[4-(aminoiminomethyl)phenyl]2-oxo-3-pyrrolidinyl]amino]carbonyl]amino]propanoic acid trifluoroacetate;
ethyl 3(R)-[[[[1-[4-(aminoiminomethyl)phenyl]-2-oxo-3-pyrrolidinyl]amino]carbonyl]amino]butanoate trifluoroacetate;
3(R)-[[[[1-[4-(aminoiminomethyl)phenyl]-2-oxo-3-pyrrolidinyl]amino]carbonyl]amino]butanoic acid trifluoroacetate;
ethyl 3(S)-[[[[1-[4-(aminoiminomethyl)phenyl]-2-oxo-3-pyrrolidinyl]amino]carbonyl]amino]benzenepropanoate trifluoroacetate;
3(S)-[[[[1-[4-(aminoiminomethyl)phenyl]-2-oxo-3-pyrrolidinyl]amino]carbonyl]amino]benzenepropanoic acid trifluoroacetate;
ethyl 3-[[[[1-[4-(aminoiminomethyl)phenyl]-2-oxo-3-pyrrolidinyl]amino]carbonyl]amino]-2(S)-[[(phenylmethoxy)carbonyl]amino]propanoate trifluoroacetate;
and
3-[[[[1-[4-(aminoiminomethyl)phenyl]-2-oxo-3-pyrrolidinyl]amino]carbonyl]amino]-2(S)-[[(phenylmethoxy)carbonyl]amino]propanoic acid trifluoroacetate.

17. A compound according to claim 1 wherein the pharmaceutically acceptable salt is the acetate salt.

18. A compound according to claim 17 wherein the compound is ethyl 3-[[[[1-[4-(aminoiminomethyl)phenyl]-2-oxo-3S-pyrrolidinyl]amino]carbonyl]amino]propionate, acetate.

* * * * *